US 9,376,380 B2

(12) United States Patent
Xie et al.

(10) Patent No.: US 9,376,380 B2
(45) Date of Patent: Jun. 28, 2016

(54) CANNABINOID RECEPTOR 2 (CB2) INVERSE AGONISTS AND THERAPEUTIC POTENTIAL FOR MULTIPLE MYELOMA AND OSTEOPOROSIS BONE DISEASES

(71) Applicant: University of Pittsburgh—Of the Commonwealth System of Higher Education, Pittsburgh, PA (US)

(72) Inventors: Xiang-qun Xie, Sewickley, PA (US); Peng Yang, Pittsburgh, PA (US); Rentian Feng, Pittsburgh, PA (US)

(73) Assignee: University of Pittsburgh—Of the Commonwealth System of Higher Education, Pittsburgh, PA (US)

( * ) Notice: Subject to any disclaimer, the term of this patent is extended or adjusted under 35 U.S.C. 154(b) by 0 days.

(21) Appl. No.: 14/305,941

(22) Filed: Jun. 16, 2014

(65) Prior Publication Data
US 2014/0296294 A1    Oct. 2, 2014

Related U.S. Application Data

(62) Division of application No. 13/715,603, filed on Dec. 14, 2012, now Pat. No. 8,772,541.

(60) Provisional application No. 61/576,041, filed on Dec. 15, 2011.

(51) Int. Cl.
*C07C 233/40*    (2006.01)
*C07C 311/20*    (2006.01)
(Continued)

(52) U.S. Cl.
CPC .............. *C07C 311/05* (2013.01); *C07C 69/78* (2013.01); *C07C 233/11* (2013.01);
(Continued)

(58) Field of Classification Search
CPC ....... A01N 41/06; A01N 37/18; A01N 33/02; C07C 307/00; C07C 311/00; C07C 321/00; C07C 309/00; C07C 303/00; C07C 239/00; A61K 31/135; A61K 31/165; A61K 31/18
USPC ............ 564/92; 514/604, 331, 613, 616, 625, 514/605, 617
See application file for complete search history.

(56) References Cited

U.S. PATENT DOCUMENTS 6,221,222 B1    4/2001   Kipp et al.
6,288,120 B1 *  9/2001   Cameron et al. ............. 514/605
(Continued)

FOREIGN PATENT DOCUMENTS

EP          2065370         6/2009
WO      WO 2007/055374   *  5/2007
WO      WO 2008/063625   *  5/2008

OTHER PUBLICATIONS

Zindell; Bioorganic and Medicinal Chemistry Letters, 2009, 19, 1604-1609.*

(Continued)

*Primary Examiner* — Janet L Andres
*Assistant Examiner* — Daniel Carcanague
(74) *Attorney, Agent, or Firm* — Foley & Lardner LLP

(57) ABSTRACT

Cannabionid receptor-2 inverse antagonists include compounds represented by Formula IV, or a pharmaceutically acceptable salt thereof:

IV wherein: $R^1$ and $R^2$ are independently H, alkyl, or alkenyl; $R^3$ is alkyl, alkenyl, aryl, aralkyl, aralkenyl, heterocyclyl, heterocyclylalkyl, heteroaryl, heteroarylalkyl; $R^4$ and $R^5$ are independently a bond, alkylenyl, or alkenylenyl; each $R^6$ and $R^7$ is independently selected from the group consisting of OH, F, Cl, Br, I, ($C_1$-$C_6$)alkyl, alkoxy, amino, COOH, $CONH_2$, $SO_3H$, $PO_3H_2$, CN, SH, $NO_2$ and $CF_3$; and p and q are independently 0, 1, 2, 3, 4, or 5. Such compounds may be used to treat osteoporosis or multiple myeloma.

17 Claims, 5 Drawing Sheets

(51) Int. Cl.

| | |
|---|---|
| C07C 311/05 | (2006.01) |
| C07D 211/06 | (2006.01) |
| C07C 311/48 | (2006.01) |
| C07D 235/12 | (2006.01) |
| C07D 203/08 | (2006.01) |
| C07C 69/78 | (2006.01) |
| C07C 233/36 | (2006.01) |
| C07C 311/29 | (2006.01) |
| C07D 295/135 | (2006.01) |
| C07D 213/56 | (2006.01) |
| C07C 311/18 | (2006.01) |
| C07C 233/11 | (2006.01) |
| C07C 233/13 | (2006.01) |
| C07C 233/22 | (2006.01) |
| C07C 233/63 | (2006.01) |
| C07C 233/78 | (2006.01) |

(52) U.S. Cl.
CPC ............ *C07C 233/13* (2013.01); *C07C 233/22* (2013.01); *C07C 233/36* (2013.01); *C07C 233/40* (2013.01); *C07C 233/63* (2013.01); *C07C 233/78* (2013.01); *C07C 311/18* (2013.01); *C07C 311/20* (2013.01); *C07C 311/29* (2013.01); *C07C 311/48* (2013.01); *C07D 203/08* (2013.01); *C07D 211/06* (2013.01); *C07D 213/56* (2013.01); *C07D 235/12* (2013.01); *C07D 295/135* (2013.01); C07C 2101/14 (2013.01); C07C 2103/74 (2013.01)

(56) References Cited

U.S. PATENT DOCUMENTS

| 6,498,172 | B1 * | 12/2002 | Cameron et al. ............... 514/347 |
|---|---|---|---|
| 7,030,173 | B2 | 4/2006 | Sarma et al. |
| 8,772,541 | B2 * | 7/2014 | Xie et al. ........................ 564/90 |
| 2006/0052315 | A1 * | 3/2006 | Leung et al. .................... 514/19 |
| 2007/0287706 | A1 * | 12/2007 | Dickson et al. ............. 514/230.5 |
| 2008/0132505 | A1 * | 6/2008 | Brown et al. ............... 514/235.8 |
| 2009/0275611 | A1 * | 11/2009 | Riether et al. ................ 514/311 |

OTHER PUBLICATIONS

Yang; J. Med. Chem. 2013, 56, 2045-2058.*
Wermuth, "Strategies in the Search for New Lead Compounds or Original Working Hypotheses," Practice of Medicinal Chemistry 3$^{rd}$ Ed. Elsevier, Chapter 6, pp. 125-143 (2008).
Masters, et al., "Secondary Disulfonamides and Secondary Tetrasulfondiamides as Proposed New Biological Alkylating Agents," Journal of Pharmaceutical Sciences, vol. 67, pp. 857-859 (1978).
El-Ayache, et al., Novel bis-arylsulfonamines and aryl sulfonimides as inactivators of plasminogen activator inhibitor-1 (PAI-1), Bioorganic & Medicinal Chemistry Letters 20, pp. 966-970 (2010).
Carosati, et al., "Calcium Channel Antagonists Discovered by a Multidisciplinary Approach," J. Med. Chem. vol. 49, pp. 5206-5216 (2006).
Khan, et al., "N-Benzyl-N-ethyl-4-methylbenzene-sulfonamide," Acta Cryst., E66, o2507 (2010).
Khan, et al., "N-Benzyl-N-cyclohexyl-4-methyl-benzenesulfonamide," Acta Cryst., E65, o3109, 9 pages, (2009).
Aikawa, et al., "Gold-catalyzed substitution reaction with ortho-alkynylbenzoic acid alkyl ester as an efficient alkylating agent," Tetrahedron, vol. 65, pp. 1774-1784 (2009).
Raju; Tetrahedron Letters 45, pp. 7487-7489 (2004).
Stauffer, et al., "Acyclic Amides as Estrogen Receptor Ligands: Synthesis, Binding, Receptor Interaction," Bioorganic & Medicinal Chemistry 8, pp. 1293-1316 (2000).
Ebel et al., Synthesis and Preliminary Pharmacological Evaluation of a Series of N,N'-Arylidenebis(acid amides), Journal of Medicinal Chemistry, vol. 10, No. 5, pp. 946-949 (1967).
Bogdal, et al., "Fast Solvent-free Alkylation and Amides and Lactams under Microwave Irradiation," Molecules, vol. 4, pp. 333-337 (1999).
Notari, R.E., "Theory and Practice of Prodrug Kinetics," *Methods in Enzymology*, vol. 112, pp. 309-323 (1985).
Bodor, N., "Novel Approaches in Prodrug Design," *Drugs of the Future*, vol. 6, pp. 165-182 (1981).
Ofek O, et al., Peripheral Cannabinoid Receptor, CB2, Regulates Bone Mass, *Proc Natl Acad Sci.*, vol. 103, No. 3, pp. 696-701 (2006).
Idris, "Role of Cannabinoid Receptors in Bone Disorders: Alternatives for Treatment," *Drug News Perspect*, vol. 21, No. 10, pp. 533-540 (2008).
Bab, "Regulation of Skeletal Remodeling by the Endocannabinoid System," *Ann. N.Y. Acad. Sci.*, vol. 1116, pp. 414-422 (2007).

* cited by examiner

CANNABINOID RECEPTOR 2 (CB2) INVERSE AGONISTS AND THERAPEUTIC POTENTIAL FOR MULTIPLE MYELOMA AND OSTEOPOROSIS BONE DISEASES

This application is a divisional of U.S. patent application Ser. No. 13/715,603, filed on Dec. 14, 2012, now U.S. Pat. No. 8,772,541, which claims priority from U.S. Provisional Patent Application No. 61/576,041, filed on Dec. 15, 2011, all of which are incorporated herein by reference in their entirety.

FIELD

The present invention relates to compounds by the regulation of cannabinoid receptors. More specifically, the compounds are inverse antagonists of cannabinoid receptor subtype-2, otherwise known as CB2.

BACKGROUND

Osteoporosis is a major metabolic bone disease that affects 44 million Americans or 55% of the people 50 years of age or older, among which 10 million individuals already have this disease and the rest 34 million more at increased high risk for osteoporosis. The disease causes a significant amount of morbidity and mortality in patients and is often diagnosed after a fracture occurs.

The endocannabinoid system plays an important role in regulating skeletal remodeling and bone mass [2, 3]. These physiological processes are implicated to play a role in the development and progression of osteoporosis. In particular, CB2-deficient mice show a remarkably accelerated age-related bone loss, supported by human genetic studies that portray polymorphisms in CNR2 gene (encoding CB2) as important genetic risk factors for osteoporosis. However, CB2-mediated bone anabolic action as well as the underlying mechanisms has not been fully explored. The present application provides compounds that can be used as probes to study the mechanisms involved in CB2-mediated regulation of osteoporotic signaling.

Multiple myeloma (MM), an incurable cancer of plasma cells is the second most common hematological malignancy in the United States. The disease disproportionately affects males over females, and is more common in the African American population than in Caucasians. The etiology of MM is unknown, and at present, there is no cure available, although modern treatment regimens have been able to slow disease progression in many patients, and have extended survival rates to about 3-5 years post-diagnosis.

MM patients present various symptoms, including hypercalcemia, anemia, renal failure, and impaired production of non-pathological immunoglobulins. Many patients also endure persistent bone pain, which typically stems from small fractures in the bones. Indeed, the hallmark pathology of MM is increased bone destruction and development of osteolytic lesions, which are mediated by high osteoclast (OCL) activity and make the patient more susceptible to bone fractures.

Previous work from the present inventors revealed that compounds belonging to the chemical genus shown below modulated cannabinoid receptor-2 activity. Preliminary biological data illustrates that this class of compounds to selectively modulate the CB2 receptor.

The cannabinoid receptor subtypes CB1 (brain) and CB2 (spleen) are important G-protein coupled receptor targets for developing new therapeutic agents. Since the discovery of the cannabinoid (CB) receptors, their endogenous ligands, and enzymes implicated to play a role in cannabinoid receptor and ligand biology there has been intensive pharmacological research into the therapeutic potential of cannabinergic ligands.

Clinical data related to the therapeutic potential of CB ligands for the treatment of nausea, glaucoma, cancer, stroke, pain, neuronal disorders, osteoporosis, multiple sclerosis, and autoimmune disorders has generated active interest in cannabinoid research. While most of the research efforts have focused on the development of ligands targeted to the CB1 receptor, biological data indicates that CB 1 ligands exert undesirable psychotropic side effects. These side effects have caused public concern. However, work to design novel CB2 ligands that do not confer psychotropic side effects associated with modulation of CB 1 activity has been limited, largely due to a lack of information about the three dimensional structures of the CB receptors and ligand binding sites.

The present inventors have used structure-activity relationship (SAR), studies to explore and define the chemical space of CB2 receptor that is involved in ligand binding interactions. Early studies used to define this chemical space relied on QSAR/NMR methodologies and in-silico docking experiments to identify a library of chemically diverse scaffolds as the core pharmacophore for CB2 receptor ligand design.

SUMMARY

The present invention uses SAR information to develop a new class compounds that selectively target and modulate CB2 activity, particularly with an aim to developing small molecule therapeutics for treating multiple myeloma and osteoporosis. Compounds according to the present invention also provide alternate therapeutic candidates to current medications, such as bisphosphonates, raloxifene, calcitonin and hormone replacement therapy that are used to treat osteoporosis and are known to exhibit severe adverse effects which limits their clinical use.

According to an embodiment of this invention, therefore, is provided a compound according to Formula I or a pharmaceutically acceptable salt thereof.

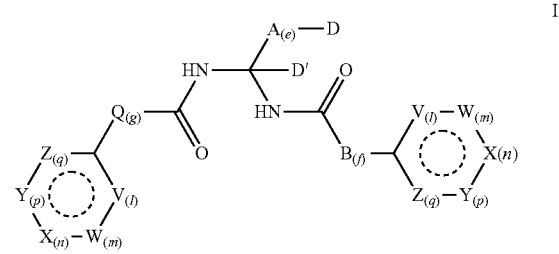

For Formula I compounds D and D' are independently —H, —OH, —OR$^a$, (C$_1$-C$_6$)alkyl or

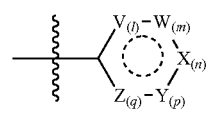

and R$^a$ is H, straight or branched chain (C$_1$-C$_6$)alkyl, (C$_3$-C$_8$) cycloalkyl, (C$_3$-C$_{14}$)aryl, (C$_3$-C$_{14}$)heterocycloalkyl-(C$_1$-C$_6$) alkylene-, (C$_3$-C$_{14}$)heteroaryl-(C$_1$-C$_6$)alkylene-, or (C$_3$-C$_{14}$) aryl(C$_1$-C$_6$)alkylene-.

In Formula I substituent groups A, B and Q are each independently $(C_1-C_6)$alkylene, $(C_2-C_6)$alkenylene or $(C_2-C_6)$alkynylene and subscripts e, f and g independently are integers between 0 and 6 inclusive.

V, W, X, Y, and Z are each independently a bond, —C(R''')$_2$—, —CR'''—, —NR'''—, —N—, —O—, —C(O)—, or —S—, with the proviso that no two adjacent members of V, W, X, Y, and Z are simultaneously —O—, —S—, or —NR'''—.

In Formula I, R''' is H, —OH, —OR$^a$, halogen, $(C_1-C_6)$alkyl, $(C_1-C_6)$alkoxy, $(C_1-C_6)$haloalkoxy, $(C_1-C_6)$haloalkyl, $(C_2-C_6)$alkenyl, $(C_2-C_6)$alkynyl, —NH$_2$, —NH$(C_1-C_6)$alkyl, —N$[(C_1-C_6)$alkyl$]_2$, —CN, $(C_3-C_8)$heteroaryl, $(C_3-C_8)$heterocycloalkyl, $(C_3-C_8)$cycloalkyl, $(C_3-C_8)$aryl, $(C_3-C_8)$heterocycloalkyl-$(C_1-C_6)$alkylene-, $(C_3-C_8)$heteroaryl-$(C_1-C_6)$alkylene-, $(C_3-C_8)$aryl$(C_1-C_6)$alkylene-, $(C_3-C_8)$aryl$(C_1-C_6)$alkenylene-, or $(C_1-C_6)$alkyl-$(C_3-C_8)$arylene and subscripts l, m, n, p and q independently are integers between 0 and 2 inclusive, with at least one of l, m, n, or p is not 0.

⊙ represents the option of having one or more double bonds. For compounds that conform to Formula I, any alkyl, alkylene, alkenylene, aryl, heteroaryl, cycloalkyl, or heterocycloalkyl is optionally substituted with halogen, oxo, —COOH, —CN, —NO$_2$, —OH, —NR$^d$R$^e$, $(C_1-C_6)$alkyl, $(C_1-C_6)$alkoxy, $(C_1-C_6)$haloalkoxy, $(C_1-C_6)$haloalkyl, $(C_3-C_8)$aryl, $(C_3-C_8)$heteroaryl, $(C_3-C_8)$heterocycloalkyl, or $(C_3-C_8)$aryloxy; with R$^d$ and R$^e$ each independently being H, straight or branched $(C_1-C_6)$alkyl, optionally substituted $(C_3-C_8)$aryl, optionally substituted $(C_3-C_{14})$aryl$(C_1-C_6)$alkylene-, and H$_2$N$(C_1-C_6)$alkylene-.

When each

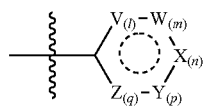

in Formula I is independently a phenyl, B$_f$ and Q$_g$ are both methylene and e is 0 then D is not 4-dimethylaminophenyl group.

Exemplary Formula I compounds are those illustrated in the table below:

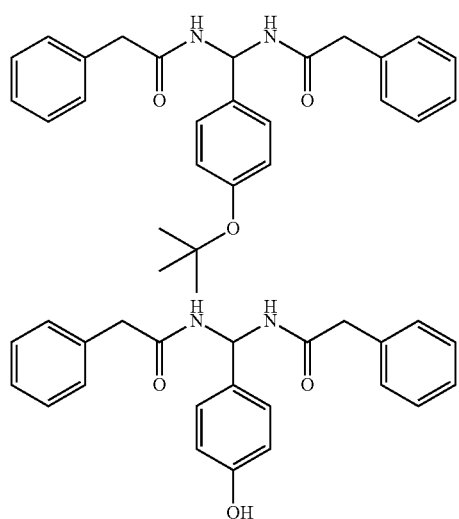

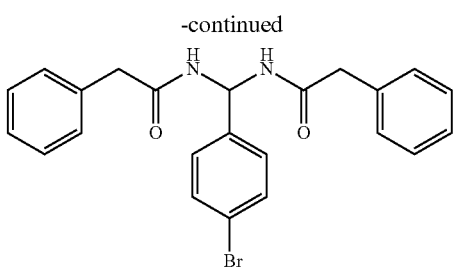

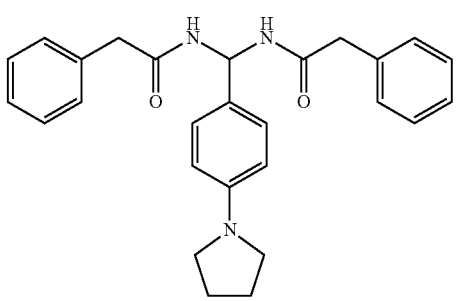

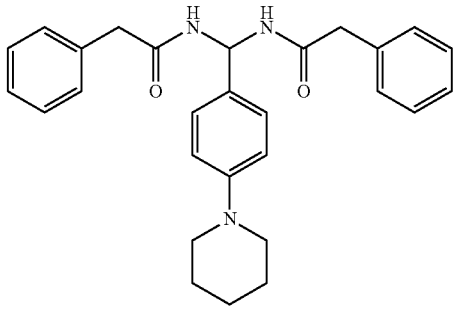

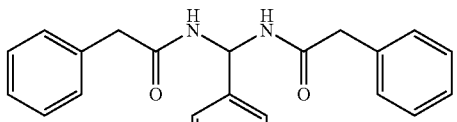

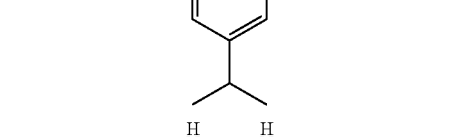

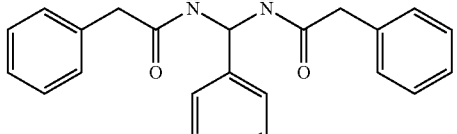

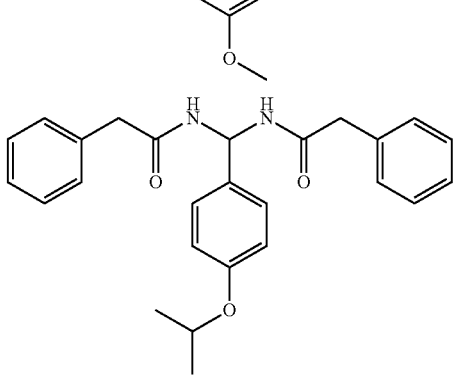

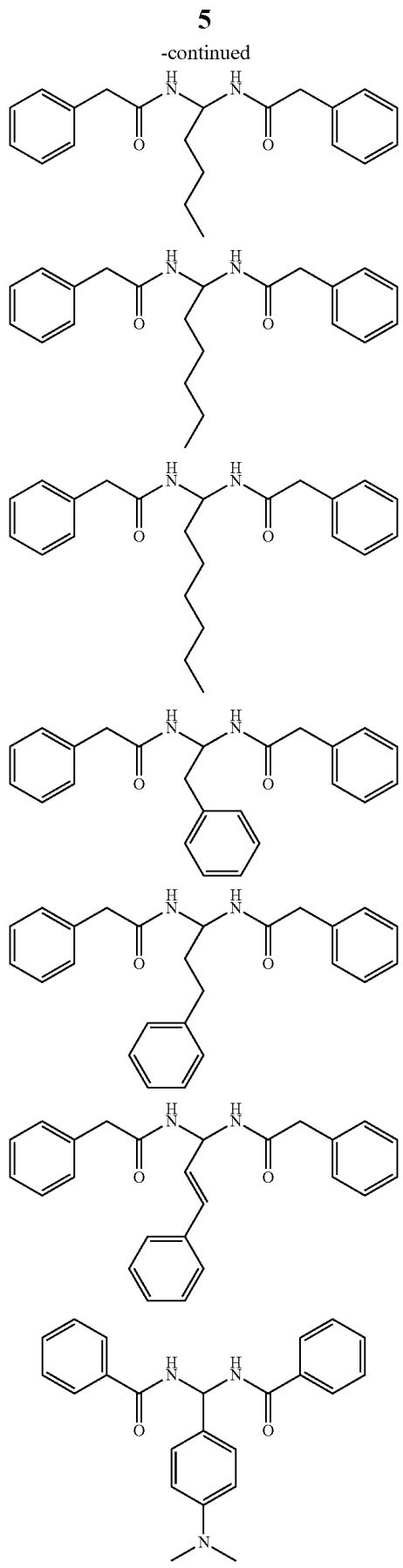
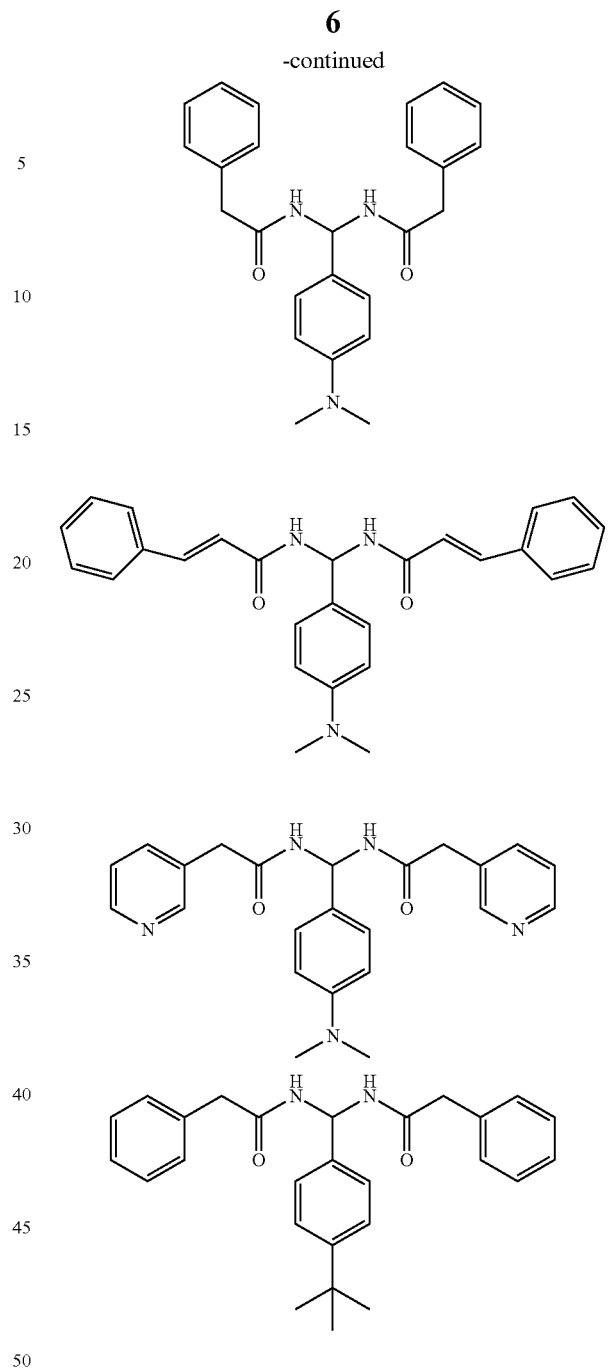
Another embodiment of the invention is a compound according to Formula I' or a pharmaceutically acceptable salt thereof:
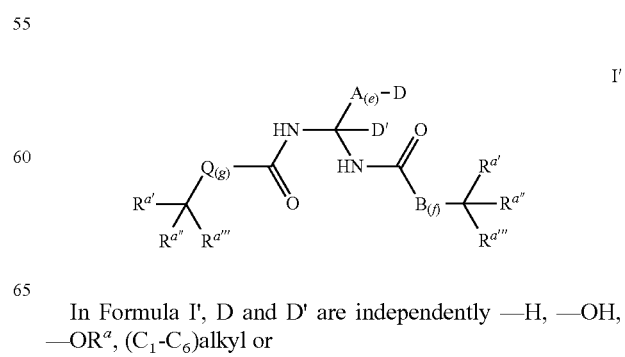
In Formula I', D and D' are independently —H, —OH, —OR$^a$, (C$_1$-C$_6$)alkyl or

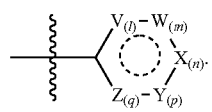

Substituents $R^{a'}$, $R^{a''}$ and $R^{a'''}$ are independently selected from the group consisting of H, straight or branched chain $(C_1-C_6)$alkyl, $(C_3-C_8)$cycloalkyl, $(C_3-C_{14})$aryl, $(C_3-C_{14})$heterocycloalkyl-$(C_1-C_6)$alkylene-, $(C_3-C_{14})$heteroaryl-$(C_1-C_6)$alkylene-, and $(C_3-C_{14})$aryl$(C_1-C_6)$alkylene-.

A, B and Q are each independently $(C_1-C_6)$alkylene, $(C_2-C_6)$alkenylene or $(C_2-C_6)$alkynylene.

Subscripts e, f and g independently are integers between 0 and 6 inclusive.

Ring members V, W, X, Y, and Z are each independently a bond, $-C(R''')_2-$, $-CR'''-$, $-NR'''-$, $-N-$, $-O-$, $-C(O)-$, or $-S-$, wherein no two adjacent members of V, W, X, Y, and Z are simultaneously $-O-$, $-S-$, or $-NR'''-$.

In Formula I', $R'''$ is H, $-OH$, $-OR^a$, halogen, $(C_1-C_6)$alkyl, $(C_1-C_6)$alkoxy, $(C_1-C_6)$haloalkoxy, $(C_1-C_6)$haloalkyl, $(C_2-C_6)$alkenyl, $(C_2-C_6)$alkynyl, $-NH_2$, $-NH(C_1-C_6)$alkyl, $-N[(C_1-C_6)$alkyl$]_2$, $-CN$, $(C_3-C_8)$heteroaryl, $(C_3-C_8)$heterocycloalkyl, $(C_3-C_8)$cycloalkyl, $(C_3-C_8)$aryl, $(C_3-C_8)$heterocycloalkyl-$(C_1-C_6)$alkylene-, $(C_3-C_8)$heteroaryl-$(C_1-C_6)$alkylene-, $(C_3-C_8)$aryl$(C_1-C_6)$alkylene-, $(C_3-C_8)$aryl$(C_1-C_6)$alkenylene-, or $(C_1-C_6)$alkyl-$(C_3-C_8)$arylene.

Subscripts l, m, n, p and q independently are integers between 0 and 2 inclusive, wherein at least one of l, m, n, or p is not 0.

Also in Formula I', the symbol

represents the option of having one or more double bonds.

In Formula I' compounds, any alkyl, alkylene, alkenylene, aryl, heteroaryl, cycloalkyl, or heterocycloalkyl is optionally substituted with halogen, oxo, $-COOH$, $-CN$, $-NO_2$, $-OH$, $-NR^dR^e$, $(C_1-C_6)$alkyl, $(C_1-C_6)$alkoxy, $(C_1-C_6)$haloalkoxy, $(C_1-C_6)$haloalkyl, $(C_3-C_8)$aryl, $(C_3-C_8)$heteroaryl, $(C_3-C_8)$heterocycloalkyl, or $(C_3-C_8)$aryloxy; and $R^d$ and $R^e$ are each independently H, straight or branched $(C_1-C_6)$alkyl, optionally substituted $(C_3-C_8)$aryl, optionally substituted $(C_3-C_{14})$aryl$(C_1-C_6)$alkylene-, and $H_2N(C_1-C_6)$alkylene-.

According to another embodiment is provided a compound according to Formula II or a pharmaceutically acceptable salt thereof.

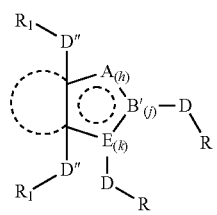

II

According to Formula II, A, B' and E are each independently a bond, $-C(R''')_2-$, $-CR'''-$, $-NR'''-$, $-N-$, $-O-$, $-C(O)-$, or $-S-$ and no two adjacent members of A, B' and E are simultaneously $-O-$, $-S-$, or $-NR'''-$. Subscripts h, j and k independently are integers between 0 and 2 inclusive, with at least one of h, j or k not being 0.

represents the option of having one or more double bonds and D and D" are each independently $-C(O)$, $-CH_2C(O)-$, $(C_1-C_6)$alkylene, $-C(O)NH-$, or $-NHC(O)-$.

For Formula II compounds,

represents the option of having a $C_5-C_6$ fused ring optionally having one or more double bonds.

R and $R_1$ are each independently OH, $-OR^a$, $(C_1-C_6)$alkyl, $(C_1-C_6)$haloalkyl, $(C_2-C_6)$alkenyl, $(C_2-C_6)$alkynyl, $(C_3-C_8)$heteroaryl, $(C_3-C_8)$heterocycloalkyl, $(C_3-C_8)$cycloalkyl, $(C_3-C_8)$aryl, $(C_3-C_8)$heterocycloalkyl-$(C_1-C_6)$alkylene-, $(C_3-C_8)$heteroaryl-$(C_1-C_6)$alkylene-, or $(C_3-C_8)$aryl$(C_1-C_6)$alkylene- and $R^a$ is H, straight or branched chain $(C_1-C_6)$alkyl, $(C_3-C_8)$cycloalkyl, $(C_3-C_{14})$aryl, $(C_3-C_{14})$heterocycloalkyl-$(C_1-C_6)$alkylene-, $(C_3-C_{14})$heteroaryl-$(C_1-C_6)$alkylene-, or $(C_3-C_{14})$aryl$(C_1-C_6)$alkylene-.

For compounds according to Formula II, any alkyl, alkylene, aryl, heteroaryl, cycloalkyl, or heterocycloalkyl is optionally substituted with one or more of halogen, oxo, $-COOH$, $-CN$, $-NO_2$, $-OH$, $-NR^dR^e$, $(C_1-C_6)$alkoxy, or $(C_3-C_8)$aryloxy; with $R^d$ and $R^e$ each independently being H, straight or branched $(C_1-C_6)$alkyl, optionally substituted $(C_3-C_{14})$aryl$(C_1-C_6)$alkylene-, and $H_2N(C_1-C_6)$alkylene-.

Exemplary Formula II compounds include

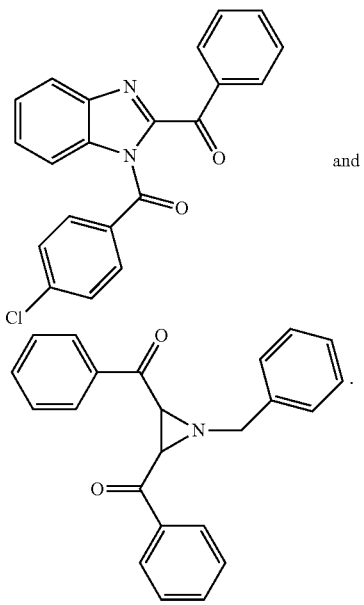

and

The invention also provides in another embodiment a compound according to Formula III' or a pharmaceutically acceptable salt thereof:

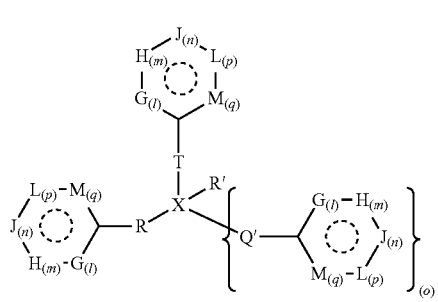

III'

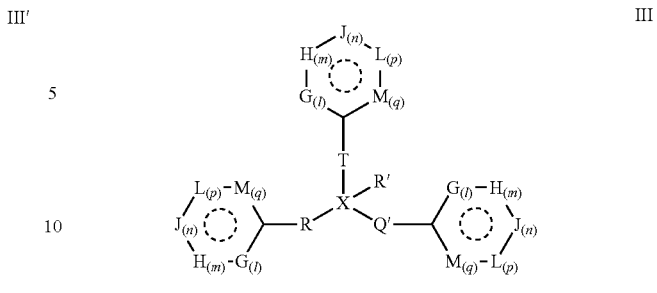

III

In Formula III', X is N,N⁺, or —CH—.

R' is H, straight or branched chain $(C_1$-$C_6)$alkyl, $(C_3$-$C_8)$cycloalkyl, $(C_3$-$C_{14})$aryl, $(C_3$-$C_{14})$heterocycloalkyl-$(C_1$-$C_6)$alkylene-, $(C_3$-$C_{14})$heteroaryl-$(C_1$-$C_6)$alkylene-, or $(C_3$-$C_{14})$aryl$(C_1$-$C_6)$alkylene-.

Q', R and T are each independently selected from a bond, —C(O)($C_1$-$C_6$)alkylene-, ($C_1$-$C_6$)alkyl, —S(O)$_2$—, —S(O)—, —S(O)$_2$NHR'', —O—($C_1$-$C_6$-alkylene)-O—, —OC(O)— and —($C_1$-$C_6$-alkylene)-OC(O)—.

G, H, J, L, and M are each independently a bond, —C(R''')$_2$—, —CR'''—, —NR'''—, —N—, —O—, —C(O)—, and —S—, wherein no two adjacent members of G, H, J, L, or M are simultaneously —O—, —S—, or —NR'''—.

R''' is H, —OH, —OR$^a$, halogen, $(C_1$-$C_6)$ alkyl, $(C_1$-$C_6)$alkoxy, $(C_1$-$C_6)$haloalkoxy, $(C_1$-$C_6)$haloalkyl, $(C_2$-$C_6)$alkenyl, $(C_2$-$C_6)$alkynyl, —NH$_2$, —NH$(C_1$-$C_6)$alkyl, —N[$(C_1$-$C_6)$alkyl]$_2$, —CN, $(C_3$-$C_8)$heteroaryl, $(C_3$-$C_8)$heterocycloalkyl, $(C_3$-$C_8)$cycloalkyl, $(C_3$-$C_8)$aryl, $(C_3$-$C_8)$heterocycloalkyl-$(C_1$-$C_6)$alkylene-, $(C_3$-$C_8)$heteroaryl-$(C_1$-$C_6)$alkylene-, $(C_3$-$C_8)$aryl$(C_1$-$C_6)$alkylene-, or $(C_1$-$C_6)$alkyl-$(C_3$-$C_8)$arylene;

Subscripts l, m, n, p and q independently are integers between 0 and 2 inclusive, wherein at least one of l, m, n, or p is not 0. Subscript o is 0 when X is N or CH, and o is 1 when X is N⁺.

The symbol

represents the option of having one or more double bonds.

R$^a$ is H, straight or branched chain $(C_1$-$C_6)$alkyl, $(C_3$-$C_8)$ cycloalkyl, $(C_3$-$C_{14})$aryl, $(C_3$-$C_{14})$heterocycloalkyl-$(C_1$-$C_6)$ alkylene-, $(C_3$-$C_{14})$heteroaryl-$(C_1$-$C_6)$alkylene-, or $(C_3$-$C_{14})$ aryl$(C_1$-$C_6)$alkylene-.

In Formula III', any alkyl, alkylene, alkenylene, aryl, heteroaryl, cycloalkyl, or heterocycloalkyl is optionally substituted with one or more of halogen, oxo, —COOH, —CN, —NO$_2$, —OH, —NR$^d$R$^e$, $(C_1$-$C_6)$alkyl, $(C_1$-$C_6)$alkoxy, $(C_1$-$C_6)$haloalkoxy, $(C_1$-$C_6)$haloalkyl, $(C_3$-$C_8)$aryl, $(C_3$-$C_8)$heteroaryl, $(C_3$-$C_8)$heterocycloalkyl, or $(C_3$-$C_8)$aryloxy; R$^d$ and R$^e$ are each independently H, straight or branched $(C_1$-$C_6)$ alkyl, optionally substituted $(C_3$-$C_8)$aryl, optionally substituted $(C_3$-$C_{14})$aryl$(C_1$-$C_6)$alkylene-, or H$_2$N$(C_1$-$C_6)$alkylene-.

The present invention also provides a compound according to Formula III or a pharmaceutically acceptable salt thereof For Formula III compounds X is N, N⁺, or —CH—. R' is H, straight or branched chain $(C_1$-$C_6)$alkyl, $(C_3$-$C_8)$cycloalkyl, $(C_3$-$C_{14})$aryl, $(C_3$-$C_{14})$heterocycloalkyl-$(C_1$-$C_6)$alkylene-, $(C_3$-$C_{14})$heteroaryl-$(C_1$-$C_6)$alkylene-, or $(C_3$-$C_{14})$aryl$(C_1$-$C_6)$alkylene-.

Substituent groups Q', R and T are each independently $(C_1$-$C_6)$alkyl, —S(O)$_2$—, —S(O)—, —S(O)$_2$NHR'', —O—(CH$_2$)$_x$—O—, —OC(O)— and (CH$_2$)$_x$—OC(O)—, while substituent groups G, H, J, L, and M each independently being a bond, —C(R''')$_2$—, —CR'''—, —NR'''—, —N—, —O—, —C(O)—, and —S—. For Formula III compounds no two adjacent members of G, H, J, L, or M are simultaneously —O—, —S—, or —NR'''—.

R''' in Formula III is H, —OH, —OR$^a$, halogen, $(C_1$-$C_6)$ alkyl, $(C_1$-$C_6)$alkoxy, $(C_1$-$C_6)$haloalkoxy, $(C_1$-$C_6)$haloalkyl, $(C_2$-$C_6)$alkenyl, $(C_2$-$C_6)$alkynyl, —NH$_2$, —NH$(C_1$-$C_6)$alkyl, —N[$(C_1$-$C_6)$alkyl]$_2$, —CN, $(C_3$-$C_8)$heteroaryl, $(C_3$-$C_8)$heterocycloalkyl, $(C_3$-$C_8)$cycloalkyl, $(C_3$-$C_8)$aryl, $(C_3$-$C_8)$heterocycloalkyl-$(C_1$-$C_6)$alkylene-, $(C_3$-$C_8)$heteroaryl-$(C_1$-$C_6)$ alkylene-, $(C_3$-$C_8)$aryl$(C_1$-$C_6)$alkylene-, or $(C_1$-$C_6)$alkyl-$(C_3$-$C_8)$arylene.

Subscripts l, m, n, p and q independently are integers between 0 and 2 inclusive, and at least one of l, m, n, or p is not 0.

in Formula IIII represents the option of having one or more double bonds. For Formula III compounds, R$^a$ is H, straight or branched chain $(C_1$-$C_6)$alkyl, $(C_3$-$C_8)$cycloalkyl, $(C_3$-$C_{14})$ aryl, $(C_3$-$C_{14})$heterocycloalkyl-$(C_1$-$C_6)$alkylene-, $(C_3$-$C_{14})$ heteroaryl-$(C_1$-$C_6)$alkylene-, or $(C_3$-$C_{14})$aryl$(C_1$-$C_6)$alkylene-.

Any alkyl, alkylene, alkenylene, aryl, heteroaryl, cycloalkyl, or heterocycloalkyl in a Formula IIII compound is optionally substituted with one or more of halogen, oxo, —COOH, —CN, —NO$_2$, —OH, —NR$^d$R$^e$, $(C_1$-$C_6)$alkyl, $(C_1$-$C_6)$alkoxy, $(C_1$-$C_6)$haloalkoxy, $(C_1$-$C_6)$haloalkyl, $(C_3$-$C_8)$aryl, $(C_3$-$C_8)$heteroaryl, $(C_3$-$C_8)$heterocycloalkyl, or $(C_3$-$C_8)$aryloxy; with R$^d$ and R$^e$ each independently being H, straight or branched $(C_1$-$C_6)$alkyl, optionally substituted $(C_3$-$C_8)$aryl, optionally substituted $(C_3$-$C_{14})$aryl$(C_1$-$C_6)$alkylene-, or H$_2$N$(C_1$-$C_6)$alkylene-.

According to one embodiment substituent X in Formula III is N and substituents T and R are each independently —S(O)$_2$— and Q' is $(C_1$-$C_6)$alkyl. Alternatively, substituent X is —CH— and each of Q', R and T are independently —O—(CH$_2$)$_x$—O—, —OC(O)— or (CH$_2$)$_x$—OC(O)—.

Exemplary Formula III compounds include

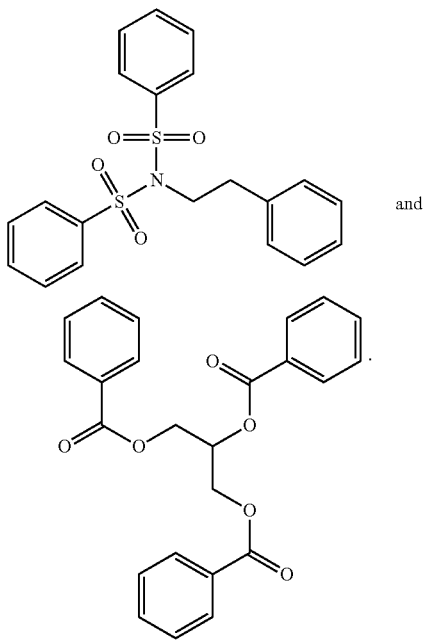

and

The present invention also provides a pharmaceutical composition comprising a therapeutically effective amount of a Formulae I, II, or III compound, or a pharmaceutically acceptable salt thereof; and a pharmaceutically acceptable carrier.

According to another embodiment is provided a method for treating multiple myeloma or osteoporosis in a subject by modulating the activity of a cannabinoid receptor-2 (CB2), comprising administering to the subject a therapeutically effective amount of a compound of Formulae I, II or III. Also provided is a method for modulating the activity of a cannabinoid receptor-2 (CB2) by contacting a CB2 receptor with a compound according to Formulae I, II, or III.

In one embodiment of the invention is provided a compound according to Formula IV or a pharmaceutically acceptable salt thereof:

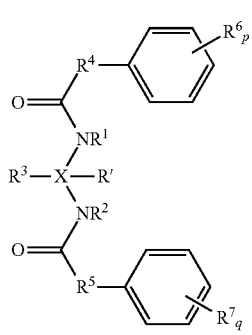

IV

According to Formula IV $R^1$ and $R^2$ are independently H, alkyl, or alkenyl. $R^3$ is alkyl, alkenyl, aryl, aralkyl, aralkenyl, heterocyclyl, heterocyclylalkyl, heteroaryl, or heteroarylalkyl.

Each of $R^4$ and $R^5$ in Formula IV are independently a bond, alkylenyl, or alkenylenyl. For Formula IV compounds each $R^6$ and $R^7$ are independently OH, F, Cl, Br, I, $(C_1-C_6)$alkyl, alkoxy, amino, COOH, $CONH_2$, $SO_3H$, $PO_3H_2$, CN, SH, $NO_2$ or $CF_3$. Subscripts p and q are independently 0, 1, 2, 3, 4, or 5. According to Formula IV, when $R^1$ and $R^2$ are both H, $R^4$ and $R^5$ are both methylene, and p and q are 0, then $R^3$ is not 4-dimethylaminophenyl.

The present invention also provides a pharmaceutical composition comprising a therapeutically effective amount of a compound of Formula IV and a pharmaceutically acceptable carrier.

DETAILED DESCRIPTION

Definitions

Figure 1:
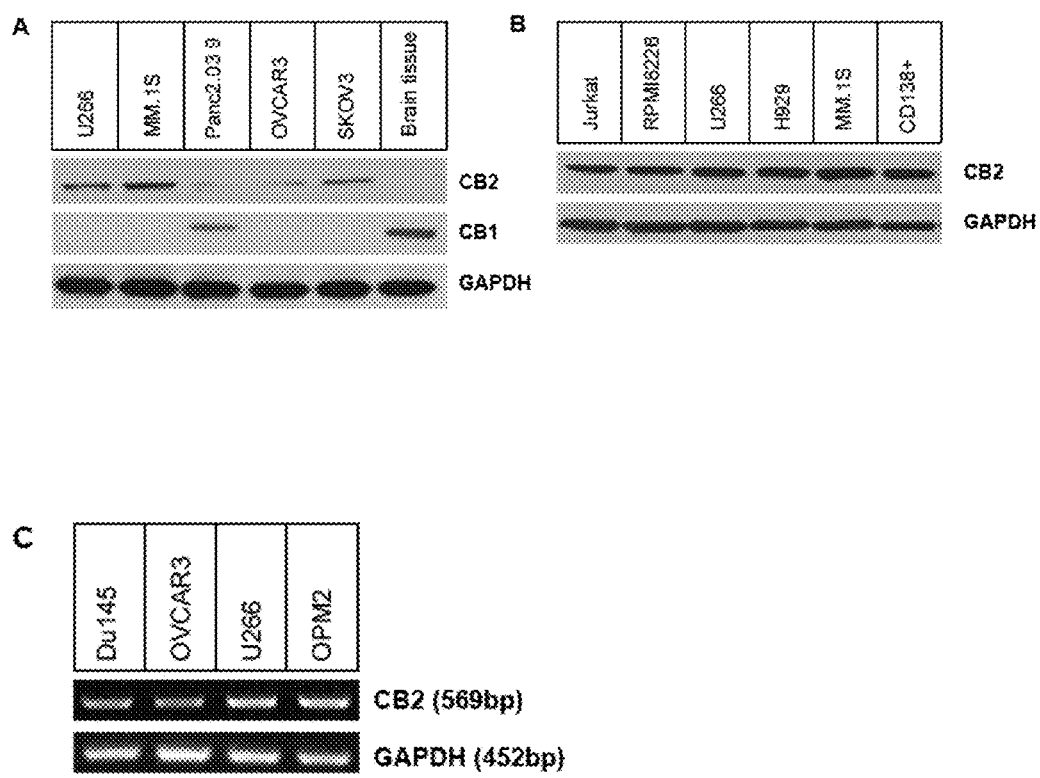
FIG. 1. Cannabinoid receptor expression in human cancer cells. (A) The protein levels of CB1 and CB2 in MM cells (U266, MM.1S) and non-MM cells (pancreatic cancer panc2.03 9, ovarian cancer OVCAR3 and SKOV3) were determined by Western blot. Cells in logarithmic phase were harvested and lysed by RIPA buffer containing protease cocktail inhibitors. To justify the expression difference of CB1 and CB2, mouse brain tissue lysate was used for the specific expression of CB 1. (B) CB2 expression in various human MM cell lines and primary CD138+ MM cells. Per the suggestion of the antibody's manufacturer, the human Jurkat cell lysate was used as the positive control for CB2 expression. (C) CB2 mRNA level was measured by RT-PCR in the indicated cell lines, using CB2 specific primers. GAPDH abundance was employed as the loading controls for immunoblot and PCR assays.

For the purposes of this disclosure and unless otherwise specified, "a" or "an" means "one or more."

"CB" is an abbreviation for "cannabinoid receptor."

"CB1" is an abbreviation for "cannabinoid receptor subtype-1."

"CB2" is an abbreviation for "cannabinoid receptor subtype-2."

Generally, reference to a certain element such as hydrogen or H is meant to include all isotopes of that element. For example, if an R group is defined to include hydrogen or H, it also includes deuterium and tritium. Hence, isotopically labeled compounds are within the scope of the invention.

In general, "substituted" refers to an organic group as defined below (e.g., an alkyl group) in which one or more bonds to a hydrogen atom contained therein are replaced by a bond to non-hydrogen or non-carbon atoms. Substituted groups also include groups in which one or more bonds to a carbon(s) or hydrogen(s) atom are replaced by one or more bonds, including double or triple bonds, to a heteroatom. Thus, a substituted group will be substituted with one or more substituents, unless otherwise specified. In some embodiments, a substituted group is substituted with 1, 2, 3, 4, 5, or 6 substituents. Examples of substituent groups include: halogens (i.e., F, Cl, Br, and I); hydroxyls; alkoxy, alkenoxy, alkynoxy, aryloxy, aralkyloxy, heterocyclyloxy, and heterocyclylalkoxy groups; carbonyls (oxo); carboxyls; esters; urethanes; oximes; hydroxylamines; alkoxyamines; aralkoxyamines; thiols; sulfides; sulfoxides; sulfones; sulfonyls; sulfonamides; amines; N-oxides; hydrazines; hydrazides; hydrazones; azides; amides; ureas; amidines; guanidines; enamines; imides; isocyanates; isothiocyanates; cyanates; thiocyanates; imines; nitro groups; nitriles (i.e., CN); and the like.

Substituted ring groups such as substituted cycloalkyl, aryl, heterocyclyl and heteroaryl groups also include rings and fused ring systems in which a bond to a hydrogen atom is replaced with a bond to a carbon atom. Therefore, substituted cycloalkyl, aryl, heterocyclyl and heteroaryl groups may also be substituted with substituted or unsubstituted alkyl, alkenyl, and alkynyl groups as defined below.

Alkyl groups include straight chain and branched alkyl groups having from 1 to about 20 carbon atoms, and typically from 1 to 12 carbons or, in some embodiments, from 1 to 8, 1 to 6, or 1 to 4 carbon atoms. Alkyl groups further include cycloalkyl groups as defined below. Examples of straight chain alkyl groups include those with from 1 to 8 carbon atoms such as methyl, ethyl, n-propyl, n-butyl, n-pentyl, n-hexyl, n-heptyl, and n-octyl groups. Examples of branched alkyl groups include, but are not limited to, isopropyl, isobutyl, sec-butyl, tert-butyl, neopentyl, isopentyl, and 2,2-dimethylpropyl groups. Representative substituted alkyl groups may be substituted one or more times with substituents such as those listed above.

Cycloalkyl groups are cyclic alkyl groups such as, but not limited to, cyclopropyl, cyclobutyl, cyclopentyl, cyclohexyl, cycloheptyl, and cyclooctyl groups. In some embodiments, the cycloalkyl group has 3 to 8 ring members, whereas in other embodiments the number of ring carbon atoms range from 3 to 5, 3 to 6, or 3 to 7. Cycloalkyl groups further include mono-, bicyclic and polycyclic ring systems, such as, for example bridged cycloalkyl groups as described below, and fused rings, such as, but not limited to, decalinyl, and the like. In some embodiments, polycyclic cycloalkyl groups have three rings. Substituted cycloalkyl groups may be substituted one or more times with, non-hydrogen and non-carbon groups as defined above. However, substituted cycloalkyl groups also include rings that are substituted with straight or branched chain alkyl groups as defined above. Representative substituted cycloalkyl groups may be mono-substituted or substituted more than once, such as, but not limited to, 2,2-, 2,3-, 2,4-2,5- or 2,6-disubstituted cyclohexyl groups, which may be substituted with substituents such as those listed above.

Bridged cycloalkyl groups are cycloalkyl groups in which two or more hydrogen atoms are replaced by an alkylene bridge, wherein the bridge can contain 2 to 6 carbon atoms if two hydrogen atoms are located on the same carbon atom, or 1 to 5 carbon atoms, if the two hydrogen atoms are located on adjacent carbon atoms, or 2 to 4 carbon atoms if the two hydrogen atoms are located on carbon atoms separated by 1 or 2 carbon atoms. Bridged cycloalkyl groups can be bicyclic, such as, for example bicyclo[2.1.1]hexane, or tricyclic, such as, for example, adamantyl. Representative bridged cycloalkyl groups include bicyclo[2.1.1]hexyl, bicyclo[2.2.1]heptyl, bicyclo[3.2.1]octyl, bicyclo[2.2.2]octyl, bicyclo[3.2.2]nonyl, bicyclo[3.3.1]nonyl, bicyclo[3.3.2]decanyl, adamantyl, noradamantyl, bornyl, or norbornyl groups. Substituted bridged cycloalkyl groups may be substituted one or more times with non-hydrogen and non-carbon groups as defined above. Representative substituted bridged cycloalkyl groups may be mono-substituted or substituted more than once, such as, but not limited to, mono-, di- or tri-substituted adamantyl groups, which may be substituted with substituents such as those listed above.

Cycloalkylalkyl groups are alkyl groups as defined above in which a hydrogen or carbon bond of an alkyl group is replaced with a bond to a cycloalkyl group as defined above. In some embodiments, cycloalkylalkyl groups have from 4 to 20 carbon atoms, 4 to 16 carbon atoms, and typically 4 to 10 carbon atoms. Substituted cycloalkylalkyl groups may be substituted at the alkyl, the cycloalkyl or both the alkyl and cycloalkyl portions of the group. Representative substituted cycloalkylalkyl groups may be mono-substituted or substituted more than once, such as, but not limited to, mono-, di- or tri-substituted with substituents such as those listed above.

Alkenyl groups include straight and branched chain and cycloalkyl groups as defined above, except that at least one double bond exists between two carbon atoms. Thus, alkenyl groups have from 2 to about 20 carbon atoms, and typically from 2 to 12 carbons or, in some embodiments, from 2 to 8, 2 to 6, or 2 to 4 carbon atoms. In some embodiments, alkenyl groups include cycloalkenyl groups having from 4 to 20 carbon atoms, 5 to 20 carbon atoms, 5 to 10 carbon atoms, or even 5, 6, 7, or 8 carbon atoms. Examples include, but are not limited to vinyl, allyl, —CH═CH(CH$_3$), —CH═C(CH$_3$)$_2$, —C(CH$_3$)═CH$_2$, —C(CH$_3$)═CH(CH$_3$), —C(CH$_2$CH$_3$)═CH$_2$, cyclohexenyl, cyclopentenyl, cyclohexadienyl, butadienyl, pentadienyl, and hexadienyl, among others. Representative substituted alkenyl groups may be mono-substituted or substituted more than once, such as, but not limited to, mono-, di- or tri-substituted with substituents such as those listed above.

Cycloalkenylalkyl groups are alkyl groups as defined above in which a hydrogen or carbon bond of the alkyl group is replaced with a bond to a cycloalkenyl group as defined above. Substituted cycloalkylalkenyl groups may be substituted at the alkyl, the cycloalkenyl or both the alkyl and cycloalkenyl portions of the group. Representative substituted cycloalkenylalkyl groups may be substituted one or more times with substituents such as those listed above.

Alkynyl groups include straight and branched chain alkyl groups, except that at least one triple bond exists between two carbon atoms. Thus, alkynyl groups have from 2 to about 20 carbon atoms, and typically from 2 to 12 carbons or, in some embodiments, from 2 to 8, 2 to 6, or 2 to 4 carbon atoms. Examples include, but are not limited to —C≡CH, —C≡C(CH$_3$), —C≡C(CH$_2$CH$_3$), —CH$_2$C≡CH, —CH$_2$C≡C(CH$_3$), and —CH$_2$C≡C(CH$_2$CH$_3$), among others. Representative substituted alkynyl groups may be mono-substituted or substituted more than once, such as, but not limited to, mono-, di- or tri-substituted with substituents such as those listed above.

Aryl groups are cyclic aromatic hydrocarbons that do not contain heteroatoms. Aryl groups include monocyclic, bicyclic and polycyclic ring systems. Thus, aryl groups include, but are not limited to, phenyl, azulenyl, heptalenyl, biphenylenyl, indacenyl, fluorenyl, phenanthrenyl, triphenylenyl, pyrenyl, naphthacenyl, chrysenyl, biphenyl, anthracenyl, indenyl, indanyl, pentalenyl, and naphthyl groups. In some embodiments, aryl groups contain 6-14 carbons, and in others from 6 to 12 or even 6-10 carbon atoms in the ring portions of the groups. Although the phrase "aryl groups" includes groups containing fused rings, such as fused aromatic-aliphatic ring systems (e.g., indanyl, tetrahydronaphthyl, and the like), it does not include aryl groups that have other groups, such as alkyl or halo groups, bonded to one of the ring members. Rather, groups such as tolyl are referred to as substituted aryl groups. Representative substituted aryl groups may be mono-substituted or substituted more than once. For example, monosubstituted aryl groups include, but are not limited to, 2-, 3-, 4-, 5-, or 6-substituted phenyl or naphthyl groups, which may be substituted with substituents such as those listed above.

Aralkyl groups are alkyl groups as defined above in which a hydrogen or carbon bond of an alkyl group is replaced with a bond to an aryl group as defined above. In some embodiments, aralkyl groups contain 7 to 20 carbon atoms, 7 to 14 carbon atoms or 7 to 10 carbon atoms. Substituted aralkyl groups may be substituted at the alkyl, the aryl or both the alkyl and aryl portions of the group. Representative aralkyl groups include but are not limited to benzyl and phenethyl groups and fused (cycloalkylaryl)alkyl groups such as 4-ethyl-indanyl. Representative substituted aralkyl groups may be substituted one or more times with substituents such as those listed above.

Heterocyclyl groups include aromatic (also referred to as heteroaryl) and non-aromatic ring compounds containing 3 or more ring members, of which one or more is a heteroatom such as, but not limited to, N, O, and S. In some embodiments, heterocyclyl groups include 3 to 20 ring members, whereas other such groups have 3 to 6, 3 to 10, 3 to 12, or 3 to 15 ring members. Heterocyclyl groups encompass unsaturated, partially saturated and saturated ring systems, such as, for example, imidazolyl, imidazolinyl and imidazolidinyl groups. The phrase "heterocyclyl group" includes fused ring species including those comprising fused aromatic and non-aromatic groups, such as, for example, benzotriazolyl, 2,3-dihydrobenzo[1,4]dioxinyl, and benzo[1,3]dioxolyl. The phrase also includes bridged polycyclic ring systems containing a heteroatom such as, but not limited to, quinuclidyl. However, the phrase does not include heterocyclyl groups that have other groups, such as alkyl, oxo or halo groups, bonded to one of the ring members. Rather, these are referred to as "substituted heterocyclyl groups". Heterocyclyl groups include, but are not limited to, aziridinyl, azetidinyl, pyrrolidinyl, imidazolidinyl, pyrazolidinyl, thiazolidinyl, tetrahydrothiophenyl, tetrahydrofuranyl, dioxolyl, furanyl, thiophenyl, pyrrolyl, pyrrolinyl, imidazolyl, imidazolinyl, pyrazolyl, pyrazolinyl, triazolyl, tetrazolyl, oxazolyl, isoxazolyl, thiazolyl, thiazolinyl, isothiazolyl, thiadiazolyl, oxadiazolyl, piperidyl, piperazinyl, morpholinyl, thiomorpholinyl, tetrahydropyranyl, tetrahydrothiopyranyl, oxathiane, dioxyl, dithianyl, pyranyl, pyridyl, pyrimidinyl, pyridazinyl, pyrazinyl, triazinyl, dihydropyridyl, dihydrodithiinyl, dihydrodithionyl, homopiperazinyl, quinuclidyl, indolyl, indolinyl, isoindolyl, azaindolyl (pyrrolopyridyl), indazolyl, indolizinyl, benzotriazolyl, benzimidazolyl, benzofuranyl, benzothiophenyl, benzthiazolyl, benzoxadiazolyl, benzoxazinyl, benzodithiinyl, benzoxathiinyl, benzothiazinyl, benzoxazolyl, benzothiazolyl, benzothiadiazolyl, benzo[1,3]dioxolyl, pyrazolopyridyl, imidazopyridyl (azabenzimidazolyl), triazolopyridyl, isoxazolopyridyl, purinyl, xanthinyl, adeninyl, guaninyl, quinolinyl, isoquinolinyl, quinolizinyl, quinoxalinyl, quinazolinyl, cinnolinyl, phthalazinyl, naphthyridinyl, pteridinyl, thianaphthalenyl, dihydrobenzothiazinyl, dihydrobenzofuranyl, dihydroindolyl, dihydrobenzodioxinyl, tetrahydroindolyl, tetrahydroindazolyl, tetrahydrobenzimidazolyl, tetrahydrobenzotriazolyl, tetrahydropyrrolopyridyl, tetrahydropyrazolopyridyl, tetrahydroimidazopyridyl, tetrahydrotriazolopyridyl, and tetrahydroquinolinyl groups. Representative substituted heterocyclyl groups may be mono-substituted or substituted more than once, such as, but not limited to, pyridyl or morpholinyl groups, which are 2-, 3-, 4-, 5-, or 6-substituted, or disubstituted with various substituents such as those listed above.

Heteroaryl groups are aromatic ring compounds containing 5 or more ring members, of which, one or more is a heteroatom such as, but not limited to, N, O, and S. Heteroaryl groups include, but are not limited to, groups such as pyrrolyl, pyrazolyl, triazolyl, tetrazolyl, oxazolyl, isoxazolyl, thiazolyl, pyridyl, pyridazinyl, pyrimidinyl, pyrazinyl, thiophenyl, benzothiophenyl, furanyl, benzofuranyl, indolyl, azaindolyl (pyrrolopyridyl), indazolyl, benzimidazolyl, imidazopyridyl (azabenzimidazolyl), pyrazolopyridyl, triazolopyridyl, benzotriazolyl, benzoxazolyl, benzothiazolyl, benzothiadiazolyl, imidazopyridyl, isoxazolopyridyl, thianaphthalenyl, purinyl, xanthinyl, adeninyl, guaninyl, quinolinyl, isoquinolinyl, tetrahydroquinolinyl, quinoxalinyl, and quinazolinyl groups. Although the phrase "heteroaryl groups" includes fused ring compounds such as indolyl and 2,3-dihydro indolyl, the phrase does not include heteroaryl groups that have other groups bonded to one of the ring members, such as alkyl groups. Rather, heteroaryl groups with such substitution are referred to as "substituted heteroaryl groups." Representative substituted heteroaryl groups may be substituted one or more times with various substituents such as those listed above.

Heterocyclylalkyl groups are alkyl groups as defined above in which a hydrogen or carbon bond of an alkyl group is replaced with a bond to a heterocyclyl group as defined above. Substituted heterocyclylalkyl groups may be substituted at the alkyl, the heterocyclyl or both the alkyl and heterocyclyl portions of the group. Representative heterocyclyl alkyl groups include, but are not limited to, 4-ethyl-morpholinyl, 4-propylmorpholinyl, furan-2-yl methyl, furan-3-yl methyl, pyridine-3-yl methyl, tetrahydrofuran-2-yl ethyl, and indol-2-yl propyl. Representative substituted heterocyclylalkyl groups may be substituted one or more times with substituents such as those listed above.

Heteroaralkyl groups are alkyl groups as defined above in which a hydrogen or carbon bond of an alkyl group is replaced with a bond to a heteroaryl group as defined above. Substituted heteroaralkyl groups may be substituted at the alkyl, the heteroaryl or both the alkyl and heteroaryl portions of the group. Representative substituted heteroaralkyl groups may be substituted one or more times with substituents such as those listed above.

Groups described herein having two or more points of attachment (i.e., divalent, trivalent, or polyvalent) within the compound of the invention are designated by use of the suffix, "ene." For example, divalent alkyl groups are alkylene groups, divalent aryl groups are arylene groups, divalent heteroaryl groups are divalent heteroarylene groups, and so forth. Substituted groups having a single point of attachment to the compound of the invention are not referred to using the "ene" designation. Thus, e.g., chloroethyl is not referred to herein as chloroethylene.

Alkoxy groups are hydroxyl groups (—OH) in which the bond to the hydrogen atom is replaced by a bond to a carbon atom of a substituted or unsubstituted alkyl group as defined above. Examples of linear alkoxy groups include but are not limited to methoxy, ethoxy, propoxy, butoxy, pentoxy, hexoxy, and the like. Examples of branched alkoxy groups include but are not limited to isopropoxy, sec-butoxy, tert-butoxy, isopentoxy, isohexoxy, and the like. Examples of cycloalkoxy groups include but are not limited to cyclopropyloxy, cyclobutyloxy, cyclopentyloxy, cyclohexyloxy, and the like. Representative substituted alkoxy groups may be substituted one or more times with substituents such as those listed above.

The terms "aryloxy" and "arylalkoxy" refer to, respectively, a substituted or unsubstituted aryl group bonded to an oxygen atom and a substituted or unsubstituted aralkyl group bonded to the oxygen atom at the alkyl. Examples include but are not limited to phenoxy, naphthyloxy, and benzyloxy. Representative substituted aryloxy and arylalkoxy groups may be substituted one or more times with substituents such as those listed above.

The term "amine" (or "amino") as used herein refers to —NHR⁴ and —NR⁵R⁶ groups, wherein R⁴, R⁵ and R⁶ are independently hydrogen, or a substituted or unsubstituted alkyl, alkenyl, alkynyl, cycloalkyl, aryl, aralkyl, heterocyclylalkyl or heterocyclyl group as defined herein. In some embodiments, the amine is NH₂, methylamino, dimethylamino, ethylamino, diethylamino, propylamino, isopropylamino, phenylamino, or benzylamino.

The term "amide" refers to a —NR'R"C(O)— group wherein R' and R" each independently refer to a hydrogen, (C₁-C₈)alkyl, or (C₃-C₆)aryl.

The term 'nitrile or cyano can be used interchangeably and refer to a —CN group which is bound to a carbon atom of a heteroaryl ring, aryl ring and a heterocycloalkyl ring.

The substituent —CO₂H, may be replaced with bioisosteric replacements such as:

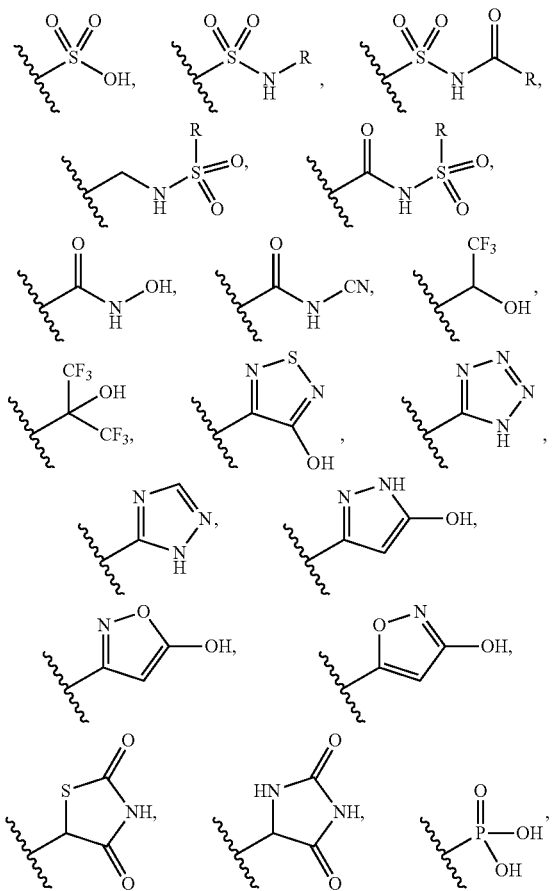

and the like, wherein R has the same definition as R' and R" as defined herein. See, e.g., THE PRACTICE OF MEDICINAL CHEMISTRY (Academic Press: New York, 1996), at page 203.

Those of skill in the art will appreciate that compounds of the invention may exhibit the phenomena of tautomerism, conformational isomerism, geometric isomerism and/or optical isomerism. As the formula drawings within the specification and claims can represent only one of the possible tautomeric, conformational isomeric, optical isomeric or geometric isomeric forms, it should be understood that the invention encompasses any tautomeric, conformational isomeric, optical isomeric and/or geometric isomeric forms of the compounds having one or more of the utilities described herein, as well as mixtures of these various different forms.

"Tautomers" refers to isomeric forms of a compound that are in equilibrium with each other. The concentrations of the isomeric forms will depend on the environment the compound is found in and may be different depending upon, for example, whether the compound is a solid or is in an organic or aqueous solution. For example, in aqueous solution, pyrazoles may exhibit the following isomeric forms, which are referred to as tautomers of each other:

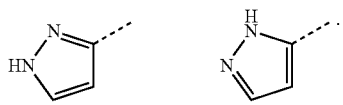

As readily understood by one skilled in the art, a wide variety of functional groups and other structures may exhibit tautomerism, and all tautomers of compounds as described herein are within the scope of the present invention.

Stereoisomers of compounds, also known as "optical isomers," include all chiral, diastereomeric, and racemic forms of a structure, unless the specific stereochemistry is expressly indicated. Thus, compounds used in the present invention include enriched or resolved optical isomers at any or all asymmetric atoms as are apparent from the depictions. Both racemic and diastereomeric mixtures, as well as the individual optical isomers can be isolated or synthesized so as to be substantially free of their enantiomeric or diastereomeric partners, and these are all within the scope of the invention.

"A pharmaceutically acceptable carrier" is a phrase that denotes a carrier such as but not limited to a diluent, an excipient, a wetting agent, a buffering agent, a suspending agent, a lubricating agent, an adjuvant, a vehicle, a delivery system, an emulsifier, a disintegrant, an absorbent, a preservative, a surfactant, a colorant, a flavorant, a sweetener, or a mixture of any two or more thereof. Pharmaceutically acceptable excipients and carriers are generally known and, hence, are included in the instant invention. Such materials are described, for example, in REMINGTON: THE SCIENCE AND PRACTICE OF PHARMACY, 21$^{st}$ ed., The University of Philadelphia (2005).

Pharmaceutical compositions and medicaments may be prepared by mixing one or more compounds of the invention, prodrugs thereof, pharmaceutically acceptable salts thereof, stereoisomers thereof, tautomers thereof, or solvates thereof, with pharmaceutically acceptable carriers, excipients, binders, diluents or the like to prevent and treat disorders associated with cannabinoid receptors. The compounds and compositions of the invention may be used to prepare formulations and medicaments that prevent or treat a variety of disorders associated with cannabinoid receptors, and described herein. For example, disorders and diseases such as obesity, smoking addiction, cardimetabolic risk factors, and other disorder and diseases associated with the central nervous system. Such compositions can be in the form of, for example, granules, powders, tablets, capsules, syrup, suppositories, injections, emulsions, elixirs, suspensions or solutions. The instant compositions can be formulated for various routes of administration, for example, by oral, parenteral, topical, rectal, nasal, vaginal administration, or via implanted reservoir. Parenteral or systemic administration includes, but is not limited to, subcutaneous, intravenous, intraperitoneally, intramuscular, intra-articular, intrasynovial, intrasternal, intrathecal, intralesional and intracranial injections. The following dosage forms are given by way of example and should not be construed as limiting the instant invention.

Pharmaceutically acceptable salts of the invention compounds are considered within the scope of the present invention. The compound of the invention has a number of basic nitrogen groups, and as such, pharmaceutically acceptable salts can be formed with inorganic acids (such as hydrochloric acid, hydroboric acid, nitric acid, sulfuric acid, and phosphoric acid), organic acids (e.g. formic acid, acetic acid, trifluoroacetic acid, fumaric acid, oxalic acid, tartaric acid, lactic acid, maleic acid, citric acid, succinic acid, malic acid, methanesulfonic acid, benzenesulfonic acid, and p-toluenesulfonic acid) or acidic amino acids (such as aspartic acid and glutamic acid). The compounds of the present invention may have acidic substituent groups, and in such cases, it can form salts with metals, such as alkali and earth alkali metals (e.g. $Na^+$, $Li^+$, $K^+$, $Ca^{2+}$, $Mg^{2+}$, $Zn^{2+}$), organic amines (e.g. ammonia, trimethylamine, triethylamine, pyridine, picoline, ethanolamine, diethanolamine, triethanolamine) or basic amino acids (e.g. arginine, lysine and ornithine).

Certain compounds within the scope of the invention are derivatives referred to as prodrugs. The expression "prodrug" denotes a derivative of a known direct acting drug, e.g. esters and amides, which derivative has enhanced delivery characteristics and therapeutic value as compared to the drug, and is transformed into the active drug by an enzymatic or chemical process; see Notari, R. E., "Theory and Practice of Prodrug Kinetics," *Methods in Enzymology* 112: 309-23 (1985); Bodor, N., "Novel Approaches in Prodrug Design," *Drugs of the Future* 6: 165-82 (1981); and Bundgaard, H., "Design of Prodrugs: Bioreversible-Derivatives for Various Functional Groups and Chemical Entities," in DESIGN OF PRODRUGS (H. Bundgaard, ed.), Elsevier (1985), Goodman and Gilmans, THE PHARMACOLOGICAL BASIS OF THERAPEUTICS, 8th ed., McGraw-Hill (1992).

For oral, buccal, and sublingual administration, powders, suspensions, granules, tablets, pills, capsules, gelcaps, and caplets are acceptable as solid dosage forms. These can be prepared, for example, by mixing one or more compounds of the instant invention, or pharmaceutically acceptable salts or tautomers thereof, with at least one additive such as a starch or other additive. Suitable additives are sucrose, lactose, cellulose sugar, mannitol, maltitol, dextran, starch, agar, alginates, chitins, chitosans, pectins, tragacanth gum, gum arabic, gelatins, collagens, casein, albumin, synthetic or semi-synthetic polymers or glycerides. Optionally, oral dosage forms can contain other ingredients to aid in administration, such as an inactive diluent, or lubricants such as magnesium stearate, or preservatives such as paraben or sorbic acid, or anti-oxidants such as ascorbic acid, tocopherol or cysteine, a disintegrating agent, binders, thickeners, buffers, sweeteners, flavoring agents or perfuming agents. Tablets and pills may be further treated with suitable coating materials known in the art.

Compounds

The compounds represented by Formulae I, I', II, III, III', and VI (below) are potent modulators of cannabinoid receptor-2 (CB2). As stated above, the endocannabinoid system, particularly CB2, plays an important role in various physiological processes, including regulation of skeletal remodeling and bone mass. These physiological processes are implicated to play a role in the development and progression of osteoporosis. While the physiological role of endocannabinoid system in multiple myeloma (MM), is not clear, cell based studies using Formulae I, I', II, III, III', and IV compounds have revealed an anti-MM activity.

In one aspect, compounds represented by Formula I, II, and III, or their pharmaceutically acceptable salts are provided:

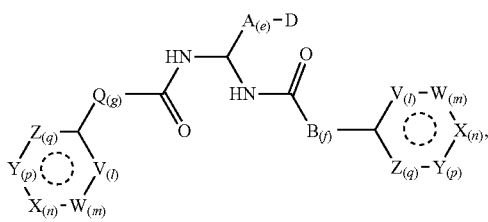

I

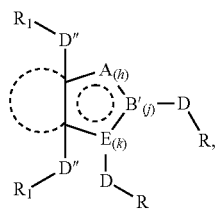

II

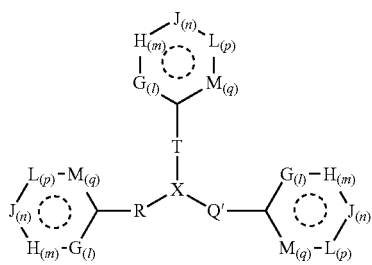

III

For Formula I compounds D is H, —OH, —OR$^a$, (C$_1$-C$_6$) alkyl or

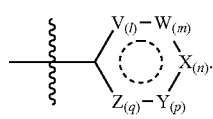

In one embodiment, D is

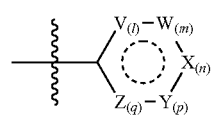

and is an aromatic phenyl group that can be optionally substituted by one, two, or three substituent groups. ⸹ represents the point of attachment of the ring to the Formula I scaffold. According to Formula I, D can be an —OR$^a$, or a (C$_1$-C$_6$)alkyl group. When D is OR$^a$, however, R$^a$ is selected from the group consisting of hydrogen, straight or branched chain (C$_1$-C$_6$) alkyl, (C$_3$-C$_8$)cycloalkyl, (C$_3$-C$_{14}$)aryl, (C$_3$-C$_{14}$)heterocycloalkyl-(C$_1$-C$_6$)alkylene-, (C$_3$-C$_{14}$)heteroaryl-(C$_1$-C$_6$)alkylene-, or (C$_3$-C$_{14}$)aryl(C$_1$-C$_6$)alkylene-. According to the above formulas, A, B and Q in Formula I are each independently (C$_1$-C$_6$)alkylene, (C$_2$-C$_6$)alkenylene and (C$_2$-C$_6$)alkynylene, while subscripts e, f and g independently are integers between 0 and 6 inclusive.

For compounds that conform to Formula I, substituent groups V, W, X, Y, or Z are each independently a bond, —C(R''')$_2$—, —CR'''—, —NR'''—, —N—, —O—, —C(O)—, and —S—. However, no two adjacent members of V, W, X, Y, or Z in Formula I are simultaneously —O—, —S—, or —NR'''—. According to Formula I compounds, V, W, X, Y, and Z are each independently a bond, —C(R''')$_2$—, —CR'''—, —NR'''—, —N—, —O—, —C(O)—, or —S—. Compounds according to Formula I encompass, therefore, species in which one, two or each of the three ring structures represents a heteroaryl group, a heterocycle group, a cycloalkyl group or an aryl ring. Exemplary of heteroaryl and heterocycle rings are oxetanyl, tetrahydrofuranyl, tetrahydropyranyl, oxepanyl, tetrahydrothiophenyl, tetrahydrothiopyranyl, 1,3-dioxanyl, oxazolidinyl, azetidinyl, pyrrolidinyl, piperidinyl, azepinyl, piperazinyl, morpholinyl, tetrahydrothiopyranyl-1-oxide, tetrahydrothiopyranyl-1,1-dioxide, pyrrolidinonyl, piperidinonyl, azepinonyl, piperazidinonyl, oxazidilinonyl, azetidinonyl, or morpholinonyl.

When any of V, W, X, Y, or Z is a —C(R''')$_2$—, —CR'''—, —NR'''— group, substituent R''' is H, OH, OR$^a$, halogen, (C$_1$-C$_6$)alkyl, (C$_1$-C$_6$)alkoxy, (C$_1$-C$_6$)haloalkoxy, (C$_1$-C$_6$)haloalkyl, (C$_2$-C$_6$)alkenyl, (C$_2$-C$_6$)alkynyl, —NH$_2$, —NH(C$_1$-C$_6$)alkyl, —N[(C$_1$-C$_6$)alkyl]$_2$, —CN, (C$_3$-C$_8$)heteroaryl, (C$_3$-C$_8$)heterocycloalkyl, (C$_3$-C$_8$)cycloalkyl, (C$_3$-C$_8$)aryl, (C$_3$-C$_8$)heterocycloalkyl-(C$_1$-C$_6$)alkylene-, (C$_3$-C$_8$)heteroaryl-(C$_1$-C$_6$)alkylene-, (C$_3$-C$_8$)aryl(C$_1$-C$_6$)alkylene-, (C$_3$-C$_8$)aryl(C$_1$-C$_6$)alkenylene-, or (C$_1$-C$_6$)alkyl-(C$_3$-C$_8$)arylene.

Subscripts l, m, n, p and q independently are integers between 0 and 2 inclusive and at least one of l, m, n, p, or q is not zero (0). To accommodate for the presence of aromatic and non-aromatic ring systems, Formula I recites

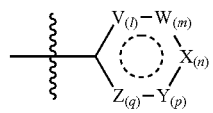

to represent the option of having one or more double bonds within a ring system. Further, for compounds that conform to Formula I, any alkyl, alkylene, alkenylene, aryl, heteroaryl, cycloalkyl, or heterocycloalkyl is optionally substituted with one or more halogen, oxo, —COOH, —CN, —NO$_2$, —OH, —NR$^d$R$^e$, (C$_1$-C$_6$)alkyl, (C$_1$-C$_6$)alkoxy, (C$_1$-C$_6$)haloalkoxy, (C$_1$-C$_6$)haloalkyl, (C$_3$-C$_8$)aryl, (C$_3$-C$_8$)heteroaryl, (C$_3$-C$_8$) heterocycloalkyl, or (C$_3$-C$_8$)aryloxy; with each of R$^d$ and R$^e$ being independently H, straight or branched (C$_1$-C$_6$)alkyl, optionally substituted (C$_3$-C$_8$)aryl, optionally substituted (C$_3$-C14)aryl(C$_1$-C$_6$)alkylene-, or H$_2$N(C$_1$-C$_6$)alkylene-. In one embodiment, the compound of Formula I is subject to the proviso that where each

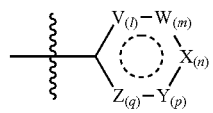

are independently phenyl, B$_f$ and Q$_g$ are both methylene, and subscript e is 0, D is a 4-dimethylaminophenyl. However, the methods of treatment described below are not necessarily subject to this proviso.

In one aspect, the compounds of Formula I also include the compounds of Formula IV:

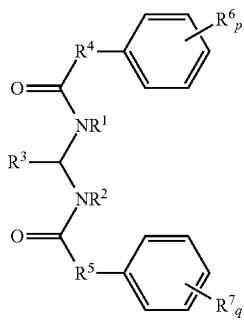

For Formula IV compounds, $R^1$ and $R^2$ are independently H, alkyl, or alkenyl and substituent $R^3$ can be alkyl, alkenyl, aryl, aralkyl, aralkenyl, heterocyclyl, heterocyclylalkyl, heteroaryl, or heteroarylalkyl. In one embodiment of Formula IV, $R^4$ and $R^5$ are independently a bond, alkylenyl, or alkenylenyl and each $R^6$ and $R^7$ is independently H, OH, F, Cl, Br, I, alkoxy, amino, —COOH, —C(O)NH$_2$, SO$_3$H, PO$_3$H$_2$, —CN, —SH, —NO$_2$, or CF$_3$ groups. For Formula IV compounds, subscripts p and q are independently 0, 1, 2, 3, 4, or 5. In some embodiments, the compounds of Formula IV are subject to the proviso that when $R^1$ and $R^2$ are both H, $R^4$ and $R^5$ are both methylene, and subscripts p and q are 0, $R^3$ in Formula IA is not 4-dimethylaminophenyl.

In some embodiments of Formula IV, $R^3$ is a substituted phenyl ring belonging to Formula B, with each $R^8$ being independently selected from OH, F, Cl, Br, I, (C$_1$-C$_6$)alkyl, alkoxy, amino, —COOH, —C(O)NH$_2$, SO$_3$H, PO$_3$H$_2$, —CN, —SH, —NO$_2$, or CF$_3$ and t is 0, 1, 2, 3, 4 or 5.

In one embodiment of Formula IV, $R^1$ and $R^2$ are independently a H or a C$_1$-C$_8$ alkyl group, substituent $R^3$ is alkyl, aryl, or aralkyl, where alkyl has from 1-8 carbons and substituent groups $R^4$ and $R^5$ are independently a bond, C$_1$-C$_8$ alkylenyl, or C$_1$-C$_8$ alkenylenyl. According to this embodiment, each $R^6$ and $R^7$ is independently OH, F, Cl, Br, I, C$_1$-C$_8$ alkoxy, or amino, subscripts p, q, and t are independently 0, 1, or 2 and each $R^8$ is independently OH, F, Cl, Br, I, alkoxy, amino.

For certain Formula IV compounds, $R^1$ and $R^2$ independently are H, $R^4$ and $R^5$ are both a bond, methylene, or ethylene and $R^3$ is

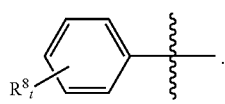

For these compounds each $R^8$ is independently OH, F, Cl, Br, I, methoxy, trifluoromethoxy, NH$_2$, dimethylamino, or diethylamino group and p, q, and t are independently 0, 1, or 2.

Exemplary Formula I compounds without limitation are those shown below in Table 1:

TABLE 1

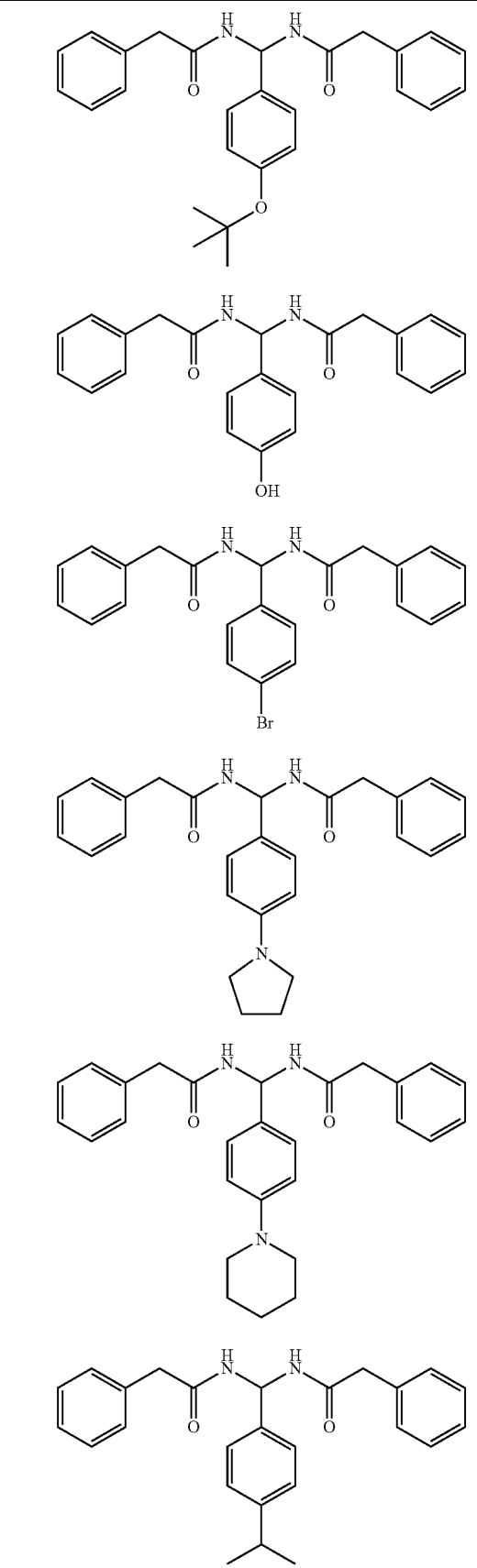

TABLE 1-continued
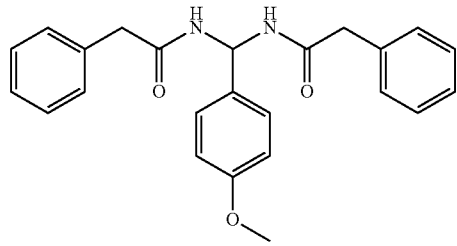 [SMILES: COc1ccc(C(NC(=O)Cc2ccccc2)NC(=O)Cc2ccccc2)cc1]
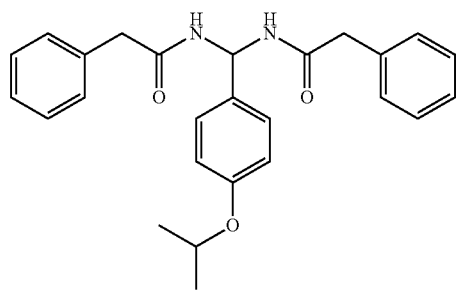 [SMILES: CC(C)Oc1ccc(C(NC(=O)Cc2ccccc2)NC(=O)Cc2ccccc2)cc1]
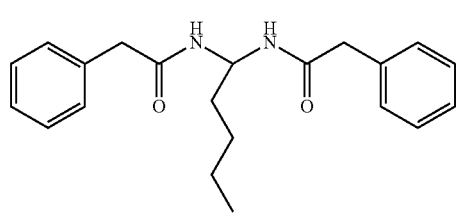 [SMILES: CCCCC(NC(=O)Cc1ccccc1)NC(=O)Cc1ccccc1]
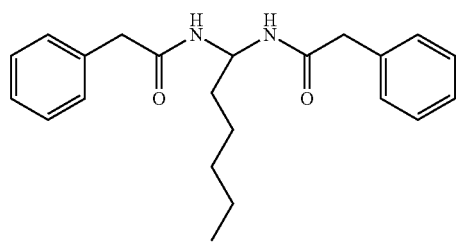 [SMILES: CCCCCC(NC(=O)Cc1ccccc1)NC(=O)Cc1ccccc1]
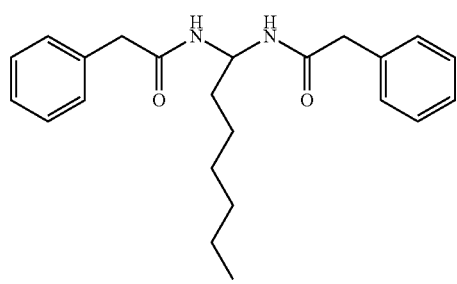 [SMILES: CCCCCCC(NC(=O)Cc1ccccc1)NC(=O)Cc1ccccc1]
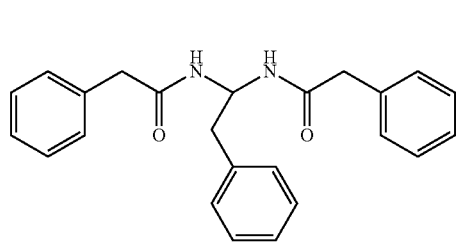 [SMILES: O=C(Cc1ccccc1)NC(Cc1ccccc1)NC(=O)Cc1ccccc1]
TABLE 1-continued
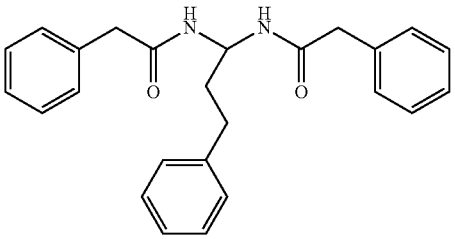 [SMILES: O=C(Cc1ccccc1)NC(CCc1ccccc1)NC(=O)Cc1ccccc1]
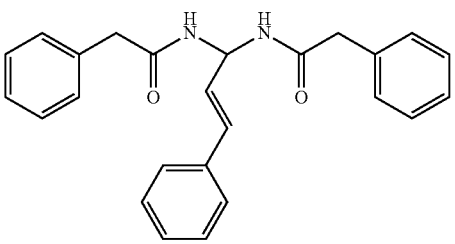 [SMILES: O=C(Cc1ccccc1)NC(/C=C/c1ccccc1)NC(=O)Cc1ccccc1]
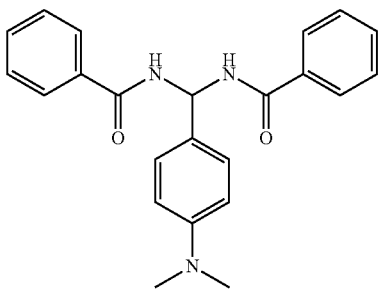 [SMILES: CN(C)c1ccc(C(NC(=O)c2ccccc2)NC(=O)c2ccccc2)cc1]
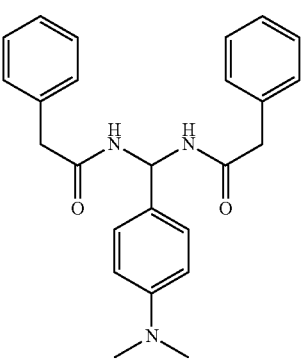 [SMILES: CN(C)c1ccc(C(NC(=O)Cc2ccccc2)NC(=O)Cc2ccccc2)cc1]
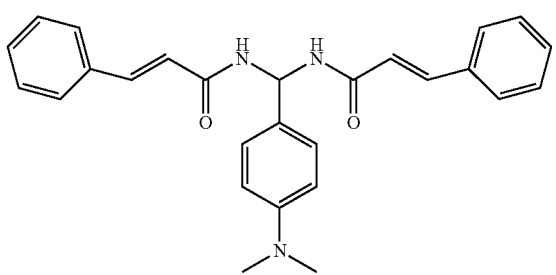 [SMILES: CN(C)c1ccc(C(NC(=O)/C=C/c2ccccc2)NC(=O)/C=C/c2ccccc2)cc1]

TABLE 1-continued

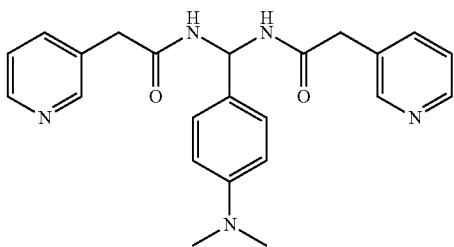 [SMILES: CN(C)c1ccc(C(NC(=O)Cc2cccnc2)NC(=O)Cc2cccnc2)cc1]

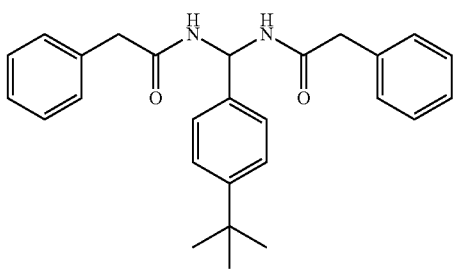 [SMILES: CC(C)(C)c1ccc(C(NC(=O)Cc2ccccc2)NC(=O)Cc2ccccc2)cc1]

As described generally above, the invention also provides compounds according to Formula I':

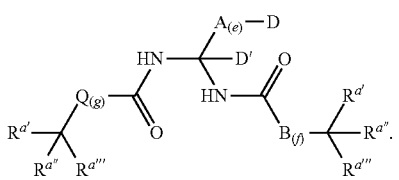

In some embodiments, the Formula I' compound is one where D is H; D' is phenyl; B and Q are independently $(C_1-C_6)$alkylene; e is 0 and each of f and g is 1; and each of $R^{a'}$, $R^{a''}$. and $R^{a'''}$ is independently selected from the group consisting of H, and straight or branched chain $(C_1-C_6)$alkyl.

Exemplary Formula I' compounds include those in the following table:

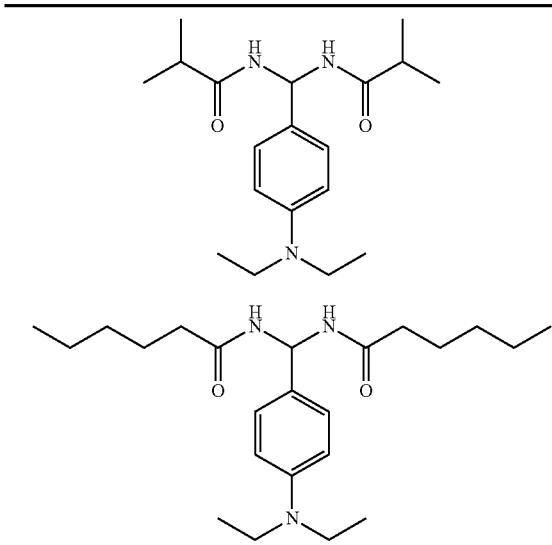

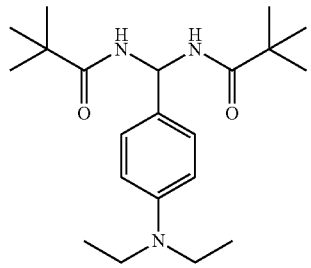 [SMILES: CCN(CC)c1ccc(C(NC(=O)C(C)(C)C)NC(=O)C(C)(C)C)cc1]

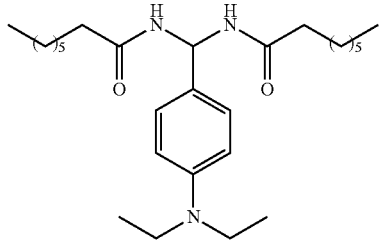

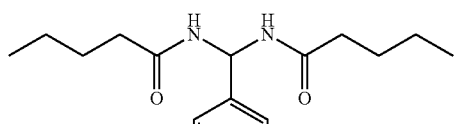

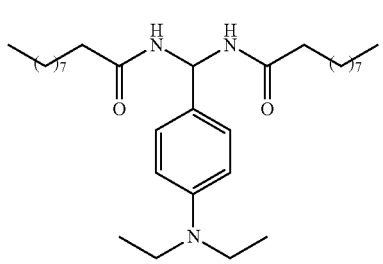

In another embodiment, is provided a CB2 ligand that conforms to Formula II.

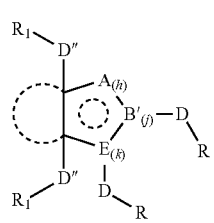

II

For Formula II compounds or their pharmaceutically acceptable salts, substituent groups A, B' and E are each independently a bond, —C(R''')$_2$—, —CR'''=, —NR'''—, —N=, —O—, —C(O)—, or —S—, however, no two adjacent members of A, B' and E can simultaneously be —O—, —S—, or —NR'''—. While subscripts h, j and k independently are integers between 0 and 2 inclusive, at least one of h, j or k is not 0 in Formula II.

In one embodiment, D and D'' are each independently —C(O), —CH$_2$C(O)—, $(C_1-C_6)$alkylene, —C(O)NH—, or —NHC(O)—. Formula II, furthermore, prescribes compounds that have a fused ring system, with

representing the option of having a $C_5$ member or a $C_6$ member fused ring that optionally has one or more double bonds.

For Formula II compounds, R and $R_1$ are each independently —OH, —$OR^a$, $(C_1-C_6)$alkyl, $(C_1-C_6)$haloalkyl, $(C_2-C_6)$alkenyl, $(C_2-C_6)$alkynyl, $(C_3-C_8)$heteroaryl, $(C_3-C_8)$heterocycloalkyl, $(C_3-C_8)$cycloalkyl, $(C_3-C_8)$aryl, $(C_3-C_8)$heterocycloalkyl-$(C_1-C_6)$alkylene-, $(C_3-C_8)$heteroaryl-$(C_1-C_6)$alkylene-, or $(C_3-C_8)$aryl$(C_1-C_6)$alkylene-.

When Group R and $R_1$ are —$OR^a$, $R^a$ is H, straight or branched chain $(C_1-C_6)$alkyl, $(C_3-C_8)$cycloalkyl, $(C_3-C_{14})$aryl, $(C_3-C_{14})$heterocycloalkyl-$(C_1-C_6)$alkylene-, $(C_3-C_{14})$heteroaryl-$(C_1-C_6)$alkylene-, or $(C_3-C_{14})$aryl$(C_1-C_6)$alkylene-.

For compounds conforming to Formula II, any alkyl, alkylene, aryl, heteroaryl, cycloalkyl, or heterocycloalkyl is optionally substituted with one or more halogen, oxo, —COOH, —CN, —$NO_2$, —OH, —$NR^dR^e$, $(C_1-C_6)$alkoxy, or $(C_3-C_8)$aryloxy; with each $R^d$ and $R^e$ independently being H, straight or branched $(C_1-C_6)$alkyl, optionally substituted $(C_3-C_{14})$aryl$(C_1-C_6)$alkylene-, or $H_2N(C_1-C_6)$alkylene-.

According to one embodiment are provided Formula II compounds in which

represents an optionally substituted phenyl group, groups A and E are independently —N—, —O—, or —S— and

represents the option of having one or more double bonds. As prescribed, therefore, compounds that conform to Formula II include without limitation analogs of phenylimidazole, 3H-indazole, indole, benz[d]oxazole, or 2,3-dihydrobenzo[d]oxazole, benzo[d]thiazole.

Exemplary of Formula II compounds without limitation are the following:

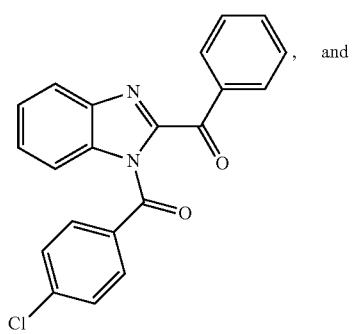, and

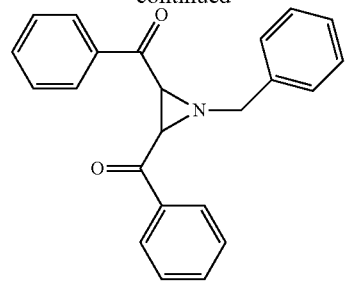

Also provided by the present invention are modulators of the CB2 receptor that conform to Formula III.

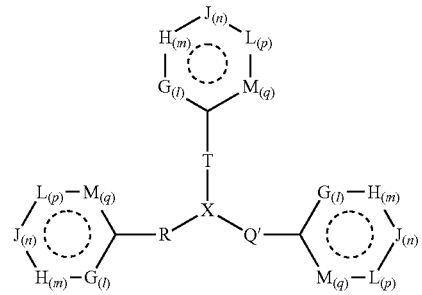

For Formula III compounds X is N, or —CH—, groups Q', R and T are each independently $(C_1-C_6)$alkyl, —$S(O)_2$—, —S(O)—, —$S(O)_2NHR''$, —O—$(CH_2)_x$—O—, —OC(O)— or $(CH_2)_x$—OC(O)—, while groups G, H, J, L, or M are each independently a bond, —$C(R''')_2$—, —CR'''—, —NR'''—, —N—, —O—, —C(O)—, or —S—.

For Formula III compounds, however, no two adjacent members of G, H, J, L, or M can simultaneously be —O—, —S—, or —NR'''—. According to one embodiment, R''' is H, OH, $OR^a$, halogen, $(C_1-C_6)$alkyl, $(C_1-C_6)$alkoxy, $(C_1-C_6)$haloalkoxy, $(C_1-C_6)$haloalkyl, $(C_2-C_6)$alkenyl, $(C_2-C_6)$alkynyl, —$NH_2$—$NH(C_1-C_6)$alkyl, —$N[(C_1-C_6)$alkyl$]_2$, —CN, $(C_3-C_8)$heteroaryl, $(C_3-C_8)$heterocycloalkyl, $(C_3-C_8)$cycloalkyl, $(C_3-C_8)$aryl, $(C_3-C_8)$heterocycloalkyl-$(C_1-C_6)$alkylene-, $(C_3-C_8)$heteroaryl-$(C_1-C_6)$alkylene-, $(C_3-C_8)$aryl$(C_1-C_6)$alkylene-, or $(C_1-C_6)$alkyl-$(C_3-C_8)$arylene. The dashed circle,

, represents the option of having one or more double bonds and for Formula III compounds, subscripts l, m, n, p and q independently are integers between 0 and 2 inclusive, with at least one of l, m, n, p, or q being a non-zero (0) integer.

When R''' is -$OR^a$, group $R^a$ is hydrogen, straight or branched chain $(C_1-C_6)$alkyl, $(C_3-C_8)$cycloalkyl, $(C_3-C_{14})$aryl, $(C_3-C_{14})$heterocycloalkyl-$(C_1-C_6)$alkylene-, $(C_3-C_{14})$heteroaryl-$(C_1-C_6)$alkylene-, or $(C_3-C_{14})$aryl$(C_1-C_6)$alkylene-.

Furthermore, for compounds conforming to Formula III, any alkyl, alkylene, alkenylene, aryl, heteroaryl, cycloalkyl, or heterocycloalkyl is optionally substituted with one or more members selected from the group consisting of halogen, oxo, —COOH, —CN, —$NO_2$, —OH, —$NR^dR^e$, $(C_1-C_6)$alkyl, ($C_1$-$C_6$)alkoxy, ($C_1$-$C_6$)haloalkoxy, ($C_1$-$C_6$)haloalkyl, ($C_3$-$C_8$)aryl, ($C_3$-$C_8$)heteroaryl, ($C_3$-$C_8$)heterocycloalkyl, or ($C_3$-$C_8$)aryloxy; with each $R^d$ and $R^e$ group being independently H, straight or branched ($C_1$-$C_6$)alkyl, optionally substituted ($C_3$-$C_8$)aryl, optionally substituted ($C_3$-$C_{14}$)aryl($C_1$-$C_6$)alkylene-, or $H_2N$($C_1$-$C_6$)alkylene-.

For certain compounds according to Formula III, substituent X is a nitrogen, substituent groups T and R are each —S(O)$_2$— and Q' is a ($C_1$-$C_6$)alkyl. For other Formula III compounds, X is —CH— and each of Q, R and T are independently —O—(CH$_2$)$_x$—O—, —OC(O)— or (CH$_2$)$_x$—OC(O)—. Illustrated below, without limitation are two compounds that conform to Formula III.

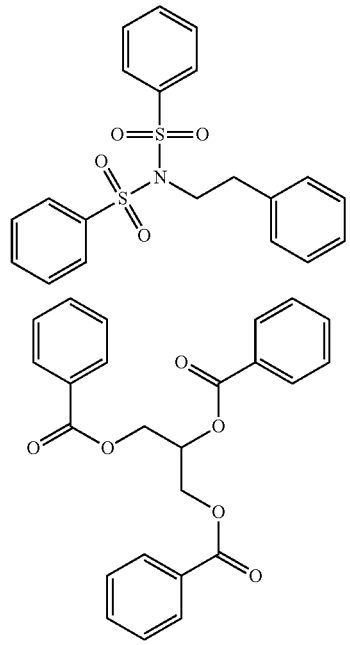

Pharmaceutical Compositions

Compounds of Formula I, II, III or IV can each be administered to a patient or subject in need of treatment either individually, or in combination with other therapeutic agents that have similar biological activities. For example, Formulae I, II, III or IV compounds and compositions can be administered as a single dose or as multiple daily doses by a practicing medical practitioner. When combination therapy is used, however, the compound and the other therapeutic agent are administered separately at different time intervals, or simultaneously.

Pharmaceutical formulations may include a compound I, II, III or IV, or a pharmaceutically acceptable salt thereof, and a pharmaceutically acceptable carrier. In some embodiments, the composition further contains, in accordance with accepted practices of pharmaceutical compounding, one or more additional therapeutic agents, pharmaceutically acceptable excipients, diluents, adjuvants, stabilizers, emulsifiers, preservatives, colorants, buffers, flavor imparting agents.

In one embodiment, the pharmaceutical composition includes a compound according to Formula I or a pharmaceutically acceptable salt thereof, and a pharmaceutically acceptable carrier.

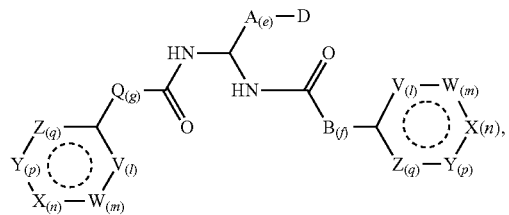

For Formula I compounds D is H, OH, $OR^a$, ($C_1$-$C_6$)alkyl and

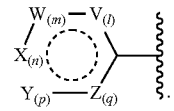

In one embodiment, D is

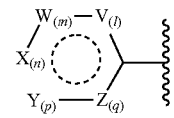

and is an aromatic phenyl group that can be optionally substituted by one, two, or three substituent groups. ⁃ represents the point of attachment of the ring to the Formula I scaffold. According to Formula I, D can be an —$OR^a$, or a ($C_1$-$C_6$)alkyl group. When D is $OR^a$, $R^a$ is H, straight or branched chain ($C_1$-$C_6$)alkyl, ($C_3$-$C_8$)cycloalkyl, ($C_3$-$C_{14}$)aryl, ($C_3$-$C_{14}$)heterocycloalkyl-($C_1$-$C_6$)alkylene-, ($C_3$-$C_{14}$)heteroaryl-($C_1$-$C_6$)alkylene-, or ($C_3$-$C_{14}$)aryl($C_1$-$C_6$)alkylene-. Groups A, B and Q in Formula I are each independently ($C_1$-$C_6$)alkylene, ($C_2$-$C_6$)alkenylene or ($C_2$-$C_6$)alkynylene, while subscripts e, f and g independently are integers between 0 and 6 inclusive. In Formula I compounds, V, W, X, Y, and Z are each independently a bond, —C(R''')$_2$—, —CR'''—, —NR'''—, —N—, —O—, —C(O)—, or —S—. However, no two adjacent members of V, W, X, Y, and Z in Formula I are simultaneously —O—, —S—, or —NR'''—. Compounds according to Formula I encompass, therefore, species in which one, two or each of the three ring structures represents a heteroaryl group, a heterocycle group, a cycloalkyl group or an aryl ring. Exemplary of heteroaryl and heterocycle rings are oxetanyl, tetrahydrofuranyl, tetrahydropyranyl, oxepanyl, tetrahydrothiophenyl, tetrahydrothiopyranyl, 1,3-dioxanyl, oxazolidinyl, azetidinyl, pyrrolidinyl, piperidinyl, azepinyl, piperazinyl, morpholinyl, tetrahydrothiopyranyl-1-oxide, tetrahydrothiopyranyl-1,1-dioxide, pyrrolidinonyl, piperidinonyl, azepinonyl, piperazidinonyl, oxazidilinonyl, azetidinonyl, and morpholinonyl.

In one embodiment, the pharmaceutical formulation includes a compound of Formula I, where any of V, W, X, Y, or Z is a —C(R''')$_2$—, —CR'''—, —NR'''— group, substituent R''' is —H, —OH, —$OR^a$, halogen, ($C_1$-$C_6$)alkyl, ($C_1$-$C_6$)alkoxy, ($C_1$-$C_6$)haloalkoxy, ($C_1$-$C_6$)haloalkyl, ($C_2$-$C_6$)alkenyl, ($C_2$-$C_6$)alkynyl, —NH$_2$, —NH($C_1$-$C_6$)alkyl, —N[($C_1$-$C_6$)alkyl]$_2$, —CN, ($C_3$-$C_8$)heteroaryl, ($C_3$-$C_8$)heterocycloalkyl, ($C_3$-$C_8$)cycloalkyl, ($C_3$-$C_8$)aryl, ($C_3$-$C_8$)heterocycloalkyl-($C_1$-$C_6$)alkylene-, ($C_3$-$C_8$)heteroaryl-($C_1$-$C_6$)alkylene-, ($C_3$-$C_8$)aryl($C_1$-$C_6$)alkylene-, ($C_3$-$C_8$)aryl($C_1$-$C_6$)

alkenylene-, or $(C_1-C_6)$alkyl-$(C_3-C_8)$arylene; l, m, n, p and q independently are integers between 0 and 2 inclusive, and at least one of l, m, n, p, or q is not zero (0). To accommodate for the presence of aromatic and non-aromatic ring systems, Formula I recites

to represent the option of having one or more double bonds within a ring system. Further, for compounds that conform to Formula I, any alkyl, alkylene, alkenylene, aryl, heteroaryl, cycloalkyl, or heterocycloalkyl is optionally substituted with halogen, oxo, —COOH, —CN, —NO$_2$, —OH, —NR$^d$R$^e$, $(C_1-C_6)$alkyl, $(C_1-C_6)$alkoxy, $(C_1-C_6)$haloalkoxy, $(C_1-C_6)$haloalkyl, $(C_3-C_8)$aryl, $(C_3-C_8)$heteroaryl, $(C_3-C_8)$heterocycloalkyl and $(C_3-C_8)$aryloxy; with each of R$^d$ and R$^e$ being H, straight or branched $(C_1-C_6)$alkyl, optionally substituted $(C_3-C_8)$aryl, optionally substituted $(C_3-C_{14})$aryl$(C_1-C_6)$alkylene-, and H$_2$N$(C_1-C_6)$alkylene-.

In one embodiment, the pharmaceutical composition comprises a compound of Formula IV, or a pharmaceutically acceptable salt thereof, and a pharmaceutically acceptable carrier:

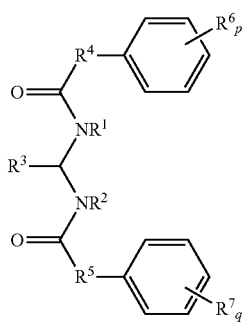

IV

In such pharmaceutical compositions including a compound of Formula IV, R$^1$ and R$^2$ are independently H, alkyl, or alkenyl; R$^3$ is alkyl, alkenyl, aryl, aralkyl, aralkenyl, heterocyclyl, heterocyclylalkyl, heteroaryl, heteroarylalkyl; R$^4$ and R$^5$ are independently a bond, alkylenyl, or alkenylenyl; each R$^6$ and R$^7$ is independently OH, F, Cl, Br, I, $(C_1-C_6)$alkyl, alkoxy, amino, —COOH, —C(O)NH$_2$, SO$_3$H, PO$_3$H$_2$, —CN, —SH, —NO$_2$, or CF$_3$; and p and q are independently 0, 1, 2, 3, 4, or 5.

In one embodiment, the pharmaceutical composition comprises a compound selected from those illustrated in Table 1 or a pharmaceutically acceptable salt, and a pharmaceutically acceptable carrier.

Multiple Myeloma and/or Osteoporosis

It has been determined that the compounds of Formulae I, I', II, III, III' and IV are CB-2 receptor inverse agonists. A link is also hereby established between CB-2 receptors and the treatment of multiple myeloma and osteoporosis. By using two distinct CB2 antibodies that are able to distinguish active and inactive CB2 receptors, the present investors found that the CB2 receptors on human MM cells are in active form. Based on the high levels of expression on MM cells and nature of the CB2 receptor on human MM cells, it is expected that CB2 ligands with antagonistic activities can be employed to inhibit MM growth. Thus, by administering a compound of Formula I, I', II, III, III' or IV to a subject, or by contacting a compound of Formula I, I', II, III, III' or IV with multiple myeloma cells or cells causing osteoporosis, the activity of the CB-2 receptors may be modulated such that the cells are inactivated, their activity is substantially altered, or the subject is treated.

In one embodiment, a method for treating multiple myeloma or osteoporosis in a subject by modulating the activity of a cannabinoid receptor-2 (CB2), includes administering to the subject a pharmaceutical composition comprising a therapeutically effective amount of a compound of Formula IV:

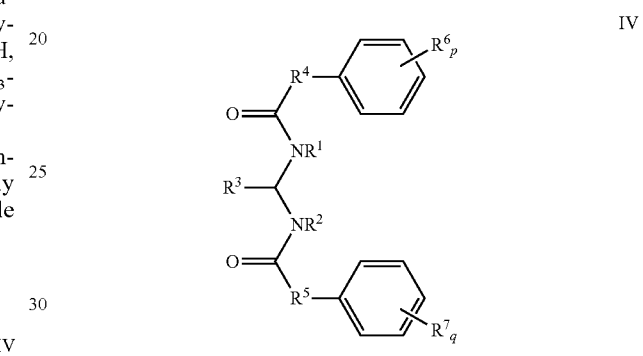

IV

In such methods utilizing Formula IV, R$^1$ and R$^2$ are independently H, alkyl, or alkenyl; R$^3$ is alkyl, alkenyl, aryl, aralkyl, aralkenyl, heterocyclyl, heterocyclylalkyl, heteroaryl, heteroarylalkyl; R$^4$ and R$^5$ are independently a bond, alkylenyl, or alkenylenyl; each R$^6$ and R$^7$ is independently OH, F, Cl, Br, I, $(C_1-C_6)$alkyl, alkoxy, amino, —COOH, —C(O)NH$_2$, SO$_3$H, PO$_3$H$_2$, —CN, —SH, —NO$_2$, CF$_3$; and p and q are independently 0, 1, 2, 3, 4, or 5. In one embodiment, the treatment is for multiple myeloma.

In another aspect, a method for modulating the activity of a cannabinoid receptor-2 (CB2) in a subject, includes contacting the CB-2 receptor with a compound of Formula IV:

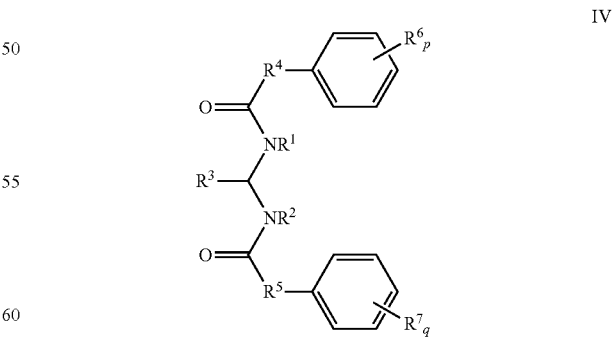

IV

In such methods utilizing Formula IV, R$^1$ and R$^2$ are independently H, alkyl, or alkenyl; R$^3$ is alkyl, alkenyl, aryl, aralkyl, aralkenyl, heterocyclyl, heterocyclylalkyl, heteroaryl, heteroarylalkyl; R$^4$ and R$^5$ are independently a bond, alkylenyl, or alkenylenyl; each R$^6$ and R$^7$ is independently OH, F, Cl, Br, I, $(C_1-C_6)$alkyl, alkoxy, amino, —COOH, —C(O)NH$_2$, SO$_3$H, PO$_3$H$_2$, —CN, —SH, —NO$_2$, CF$_3$; and p and q are independently 0, 1, 2, 3, 4, or 5.

In another aspect, a method is provided including modulating the activity of a cannabinoid receptor-2 (CB2) in a subject suffering from osteoporosis. In one embodiment, the modulating includes administering a CB-2 receptor inverse agonist to the subject. In one embodiment of the methods, the CB-2 receptor inverse agonist includes a compound of Formula IV:

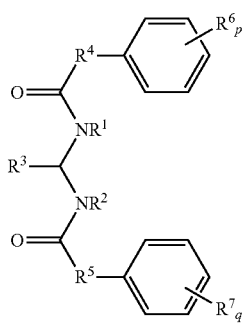

IV

In such methods utilizing Formula IV, $R^1$ and $R^2$ are independently H, alkyl, or alkenyl; $R^3$ is alkyl, alkenyl, aryl, aralkyl, aralkenyl, heterocyclyl, heterocyclylalkyl, heteroaryl, heteroarylalkyl; $R^4$ and $R^5$ are independently a bond, alkylenyl, or alkenylenyl; each $R^6$ and $R^7$ is independently OH, F, Cl, Br, I, $(C_1-C_6)$alkyl, alkoxy, amino, —COOH, —C(O)NH$_2$, SO$_3$H, PO$_3$H$_2$, —CN, —SH, —NO$_2$, CF$_3$; and p and q are independently 0, 1, 2, 3, 4, or 5.

The compositions may be administered orally, or parenterally, the term "parenteral" as used herein includes subcutaneous injections, intravenous, intramuscular, intrasternal injection or infusion techniques. Suitable oral compositions in accordance with the invention include without limitation tablets, troches, lozenges, aqueous or oily suspensions, dispersible powders or granules, emulsion, hard or soft capsules, syrups or elixirs. The dosage form may be a single unit dosage form that includes any of the compounds of Formula I, I', II, III, III' or IV, or a pharmaceutically salt thereof. Such dosage forms may include a pharmaceutically acceptable carrier.

Compositions for parenteral administrations are administered in a sterile medium. Depending on the vehicle used and concentration the concentration of the drug in the formulation, the parenteral formulation can either be a suspension or a solution containing dissolved drug. Adjuvants such as local anesthetics, preservatives and buffering agents can also be added to parenteral compositions.

The present invention, thus generally described, will be understood more readily by reference to the following examples, which are provided by way of illustration and are not intended to be limiting of the present invention.

Synthesis of Compounds

General Synthetic Methodology

The preparation of substituted amide compounds used in the coupling reactions below were prepared via hydrolysis of corresponding 2-phenylacetonitriles in concentrated H$_2$SO$_4$ (Scheme 1). The reactions were typically conducted at about 0° C. for about 12 hours.

Scheme 1:

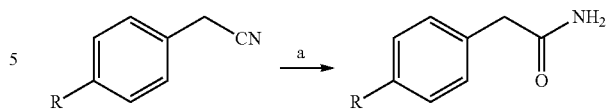

The compounds described below and shown in Table 1, were synthesized by the method a or b of Scheme. In Scheme 1a, the coupling reaction between the amide and aldehyde was performed in anhydrous dichloroethane (DCE) with the catalyst trimethylsilyl chloride (TMSCl) at about 70° C. for 3-12 hours. In Scheme 1b, the coupling reaction was performed in anhydrous dichloromethane (DCM) with the catalyst F$_3$CSO$_3$SiMe$_3$, at room temperature for about 12 hours.

Scheme 1.

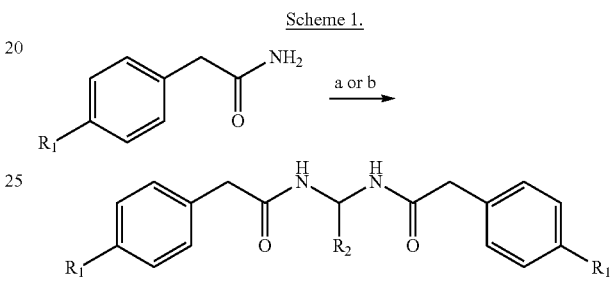

Chemistry

All reagents were purchased from commercial sources and used without further purification. Analytical thin-layer chromatography (TLC) was performed on SiO$_2$ plates on Alumina. Visualization was accomplished by UV irradiation at 254 nm. Preparative TLC was conducted using Preparative Silica gel TLC plates (1000 μm, 20 cm×20 cm). Flash column chromatography was performed using Biotage Isolera flash purification system. $^1$H NMR was recorded on a Bruker 400 MHz spectrometer. Chemical shifts are reported as δ values in parts per million (ppm) as referenced to residual solvent. $^1$H NMR spectra are tabulated as follows: chemical shift, multiplicity (s=singlet, bs=broad singlet, d=doublet, t=triplet, q=quartet, m=multiplet), coupling constant(s), and number of protons. Flash column chromatography was performed using SiO$_2$ 60 (particle size 0.040-0.055 mm, 230-400 mesh).

The chemical purity of the target compounds was >95% as determined using the following conditions: a Shimadzu HPLC-MS-MS with a HAMILTON reversed phase column (HxSil, C18, 3 μm, 2.1×50 mm (H2)); Eluent A: 5% CH$_3$CN in H$_2$O, eluent B: 90% CH$_3$CN in H$_2$O (Table 2); flow rate of 0.2 mL/min; UV detector, 254 nm.

TABLE 2

HPLC-MS-MS Eluent Compositions

| T (min) | A (%) | B (%) |
|---|---|---|
| 0.0 | 5 | 95 |
| 3.00 | 5 | 95 |
| 7.00 | 90 | 10 |
| 12.00 | 90 | 10 |
| 18.00 | 5 | 95 |
| 20.00 | stop | stop |

Preparation of 2-Phenylacetamide

Benzyl cyanide (5 g, 42.7 mmol) was added slowly to concentrated sulfuric acid (20 ml) cooled by water-ice bath.

The solution was stirred overnight. The reaction mixture was poured into ice water and neutralized with 20% NaOH. The aqueous phase was extracted by ethyl acetate (3×15 mL). The combined organic layers were washed with water (3×10 mL) and brine (3×10 mL), dried over anhydrous $MgSO_4$, filtered, and concentrated under reduced pressure. The residue was recrystallized from ethyl acetate and hexane to give the title compound (4.5 g, 78%). $^1$H NMR (400 MHz, DMSO-$d_6$) δ 7.54 (s, 1H), 7.20-7.32 (m, 5H), 6.87 (s, 1H), 3.38 (s, 2H).

2-(4-Chlorophenyl)acetamide

The same procedure was followed using 2-(4-chloro)benzyl cyanide. $^1$H NMR (400 MHz, DMSO-$d_6$) δ 7.49 (s, 1H), 7.34-7.35 (m, 2H), 7.26-7.27 (m, 2H), 6.92 (s, 1H), 3.34-3.37 (m, 2H).

(4-(Trifluoromethyl)phenyl)acetamide

The same procedure was followed using 4-trifluoromethylbenzyl cyanide. $^1$H NMR (400 MHz, DMSO-$d_6$) δ 7.65 (d, J=8.0 Hz, 2H), 7.58 (s, 1H), 7.49 (d, J=8.0 Hz, 2H), 7.00 (s, 1H), 3.51 (s, 2H).

General Protocol for the Coupling Reaction Between Amide and Aldehyde—Method 1.

N,N'-((4-(dimethylamino)phenyl)methylene)bis(2-phenylacetamide) (1). To a suspension of 4-(dimethylamino)benzaldehyde (149 mg, 1 mmol) and 2-phenylacetamide (270 mg, 2 mmol) in 2 mL anhydrous DCE, TMSCl (216 mg, 2 mmol) was added. The mixture was heated at 70° C. for 12 h, then cooled to room temperature and the crude product precipitated from the solution. The crude product was recrystallized with methanol and hexane to give the final product (140 mg, 35%). $^1$H NMR (400 MHz, DMSO-$d_6$) δ 8.89 (d, J=8.0 Hz, 2H), 7.59 (s, 2H), 7.41 (d, J=8.8 Hz, 2H), 7.21-7.32 (m, 10H), 6.54 (t, J=8.0 Hz, 1H), 3.52 (dd, J=14.0, 15.6 Hz, 4H), 3.06 (s, 6H).

N,N'-(phenylmethylene)bis(2-phenylacetamide) (2). Yield: 67%. $^1$H NMR (400 MHz, DMSO-$d_6$) δ 8.78 (d, J=7.2 Hz, 2H), 7.21-7.35 (m, 15H), 6.55 (t, J=7.8 Hz, 1H), 3.50 (dd, J=13.8, 20.4 Hz, 4H).

N,N'-((2-fluorophenyl)methylene)bis(2-phenylacetamide) (3). Yield: 64%. $^1$H NMR (400 MHz, DMSO-$d_6$) δ 8.87 (d, J=7.8 Hz, 2H), 7.44 (t, J=7.8 Hz, 1H), 7.36 (q, J=6.6 Hz, 1H), 7.17-7.29 (m, 12H), 6.74 (t, J=7.8 Hz, 1H), 3.48 (dd, J=14.4, 24.0 Hz, 4H).

N,N'-((4-fluorophenyl)methylene)bis(2-phenylacetamide) (5). Yield: 72%. $^1$H NMR (400 MHz, DMSO-$d_6$) δ 8.79 (d, J=8.0 Hz, 2H), 7.16-7.36 (m, 14H), 6.54 (t, J=8.0 Hz, 1H), 3.52 (dd, J=14.4, 15.6 Hz, 4H).

N,N'-((4-chlorophenyl)methylene)bis(2-phenylacetamide) (6). Yield: 71%. $^1$H NMR (400 MHz, DMSO-$d_6$) δ 8.83 (d, J=7.8 Hz, 2H), 7.41 (d, J=7.8 Hz, 2H), 7.21-7.32 (m, 12H), 6.51 (t, J=7.8 Hz, 1H), 3.50 (dd, J=14.4, 17.4 Hz, 4H).

N,N'-(p-tolylmethylene)bis(2-phenylacetamide) (8). Yield: 70%. $^1$H NMR (400 MHz, DMSO-$d_6$) δ 8.71 (d, J=8.0 Hz, 2H), 7.13-7.32 (m, 14H), 6.52 (t, J=8.0 Hz, 1 Hz, 1H), 3.51 (dd, J=14.4, 15.6 Hz, 4H), 2.29 (S, 3H).

N,N'-((4-methoxyphenyl)methylene)bis(2-phenylacetamide) (10). Yield: 62%. $^1$H NMR (400 MHz, DMSO-$d_6$) δ 8.70 (d, J=7.6 Hz, 2H), 7.21-7.31 (m, 12H), 6.89 (d, J=8.8 Hz, 2H), 6.51 (t, J=8.0 Hz, 1H), 3.74 (s, 3H), 3.50 (dd, J=14.0, 17.2 Hz, 4H).

N,N'-((2-(trifluoromethyl)phenyl)methylene)bis(2-phenylacetamide) (13). Yield: 70%. $^1$H NMR (400 MHz, DMSO-$d_6$) δ 8.87 (d, J=7.2 Hz, 2H), 7.78 (d, J=7.6 Hz, 1H), 7.68-7.73 (m, 2H), 7.54 (t, J=7.6 Hz, 1H), 7.19-7.30 (m, 10H), 6.83 (t, J=6.8 Hz, 1H), 3.46 (dd, J=14.0, 17.6 Hz, 4H).

N,N'-((4-(trifluoromethyl)phenyl)methylene)bis(2-phenylacetamide) (14). Yield: 75%. $^1$H NMR (400 MHz, DMSO-$d_6$) δ 8.89 (d, J=7.6 Hz, 2H), 7.72 (d, J=7.6 Hz, 2H), 7.51 (d, J=7.6 Hz, 2H), 7.25-7.30 (m, 10H), 6.58 (t, J=7.2 Hz, 1H), 3.53 (s, 4H).

N,N'-((4-nitrophenyl)methylene)bis(2-phenylacetamide) (15). Yield: 84%. $^1$H NMR (400 MHz, DMSO-$d_6$) δ 8.94 (d, J=7.8 Hz, 2H), 8.14 (d, J=8.4 Hz, 2H), 7.50 (d, J=8.4 Hz, 2H), 7.16-7.25 (m, 10H), 6.52 (t, J=7.8 Hz, 1H), 3.47 (s, 4H).

N,N'-((4-(diethylamino)phenyl)methylene)bis(2-phenylacetamide) (17). Yield: 14%. $^1$H NMR (400 MHz, DMSO-$d_6$) δ 8.60 (d, J=8.0 Hz, 2H), 7.21-7.31 (m, 10H), 7.07 (d, J=8.4 Hz, 2H), 6.60 (d, J=8.8 Hz, 2H), 6.43 (t, J=8.0 Hz, 1H), 3.44-3.52 (m, 4H), 3.29-3.34 (m, 4H), 1.06 (t, J=7.6 Hz, 6H). LC-MS (ESI): m/z 430.3 (M+H)$^+$.

N,N'-((4-(dibutylamino)phenyl)methylene)bis(2-phenylacetamide) (18). Yield: 15%. $^1$H NMR (400 MHz, DMSO-$d_6$) δ 8.58 (d, J=8.0 Hz, 2H), 7.20-7.31 (m, 10H), 7.06 (d, J=8.8 Hz, 2H), 6.57 (d, J=8.8 Hz, 2H), 6.41 (t, J=8.0 Hz, 1H), 3.47-3.48 (m, 4H), 3.22-3.26 (m, 4H), 1.43-1.50 (m, 4H), 1.26-1.35 (m, 4H), 0.91 (t, J=7.6 Hz, 6H). LC-MS (ESI): m/z 486.2 (M+H)$^+$.

N,N'-((4-(piperidin-1-yl)phenyl)methylene)bis(2-phenylacetamide) (19). Yield: 45%. $^1$H NMR (400 MHz, DMSO-$d_6$) δ 8.80 (d, J=8.0 Hz, 2H), 7.15-7.32 (m, 14H), 6.51 (t, J=8.0 Hz, 1H), 3.37-3.52 (m, 8H), 1.61-1.83 (m, 6H). LC-MS (ESI): m/z 442.3 (M+H)$^+$.

N,N'-(phenylmethylene)bis(2-(4-chlorophenyl)acetamide) (21). Yield: 52%. $^1$H NMR (400 MHz, DMSO-$d_6$) δ 8.88 (d, J=7.8 Hz, 2H), 7.25-7.41 (m, 13H), 6.52 (t, J=7.8 Hz, 1H), 3.50 (s, 4H).

N,N'-((2-fluorophenyl)methylene)bis(2-(4-chlorophenyl)acetamide) (22). Yield: 63%. $^1$H NMR (400 MHz, DMSO-$d_6$) δ 8.93 (d, J=7.2 Hz, 2H), 7.45 (t, J=7.2 Hz, 1H), 7.33-7.37 (m, 5H), 7.25-7.26 (m, 4H), 7.18-7.21 (m, 2H), 6.73 (t, J=7.2 Hz, 1H), 3.48 (s, 4H).

N,N'-((4-fluorophenyl)methylene)bis(2-(4-chlorophenyl)acetamide) (23). Yield: 67%. $^1$H NMR (400 MHz, DMSO-$d_6$) δ 8.82 (d, J=7.6 Hz, 2H), 7.34-7.37 (m, 6H), 7.27 (d, J=8.4 Hz, 4H), 7.19 (t, J=8.8 Hz, 2H), 6.51 (t, J=8.0 Hz, 1H), 3.51 (s, 4H).

N,N'-((4-chlorophenyl)methylene)bis(2-(4-chlorophenyl)acetamide) (24). Yield: 40%. $^1$H NMR (400 MHz, DMSO-$d_6$) δ 8.88 (d, J=7.8 Hz, 2H), 7.42 (d, J=8.4 Hz, 2H), 7.31-7.35 (m, 6H), 7.26 (d, J=8.4 Hz, 4H), 6.47 (t, J=7.8 Hz, 1H), 3.50 (s, 4H).

N,N'-(p-tolylmethylene)bis(2-(4-chlorophenyl)acetamide) (25). Yield: 68%. $^1$H NMR (400 MHz, DMSO-$d_6$) δ 8.76 (d, J=8.0 Hz, 2H), 7.34 (d, J=8.4 Hz, 4H), 7.28 (d, J=8.4 Hz, 4H), 7.17 (q, J=8.0 Hz, 4H), 6.50 (t, J=7.6 Hz, 1H), 3.51 (s, 4H), 2.29 (s, 3H).

N,N'-((4-methoxyphenyl)methylene)bis(2-(4-chlorophenyl)acetamide) (26). Yield: 61%. $^1$H NMR (400 MHz, DMSO-$d_6$) δ 8.73 (d, J=7.6 Hz, 2H), 7.34 (d, J=8.8 Hz, 4H), 7.26 (d, J=8.4 Hz, 4H), 7.21 (d, J=8.8 Hz, 2H), 6.90 (d, J=8.8 Hz, 2H), 6.46 (t, J=8.0 Hz, 1H), 3.74 (s, 3H), 3.49 (s, 4H).

N,N'-((2-(trifluoromethyl)phenyl)methylene)bis(2-(4-chlorophenyl)acetamide) (27). Yield: 72%. $^1$H NMR (400 MHz, DMSO-$d_6$) δ 8.04 (d, J=6.0 Hz, 2H), 7.81 (d, J=7.8 Hz, 1H), 7.72 (d, J=7.8 Hz, 1H), 7.62 (t, J=7.8 Hz, 1H), 7.52 (t, J=7.8 Hz, 1H), 7.27-7.30 (m, 8H), 7.06 (t, J=7.2 Hz, 1H), 3.52 (s, 4H).

N,N'-((4-(trifluoromethyl)phenyl)methylene)bis(2-(4-chlorophenyl)acetamide) (28). Yield: 65%. $^1$H NMR (400 MHz, DMSO-$d_6$) δ 8.96 (d, J=7.6 Hz, 2H), 7.73 (d, J=8.4 Hz, 2H), 7.54 (d, J=8.4 Hz, 2H), 7.35 (d, J=8.4 Hz, 4H), 7.28 (d, J=8.4 Hz, 4H), 6.57 (t, J=7.6 Hz, 1H), 3.54 (s, 4H).

N,N'-((4-nitrophenyl)methylene)bis(2-(4-chlorophenyl)acetamide) (29). Yield: 80%. $^1$H NMR (400 MHz, DMSO-$d_6$)

δ 9.02 (d, J=7.2 Hz, 2H), 8.21-8.23 (m, 2H), 7.57 (d, J=7.8 Hz, 2H), 7.33-7.35 (m, 4H), 7.26 (d, J=6.6 Hz, 4H), 6.55 (t, J=7.8 Hz, 1H), 3.53 (S, 4H).

N,N'-(phenylmethylene)bis(2-(4-(trifluoromethyl)phenyl)acetamide) (30). Yield: 73%. $^1$H NMR (400 MHz, DMSO-$d_6$) δ 8.94 (d, J=7.8 Hz, 2H), 7.63 (d, J=7.8 Hz, 4H), 7.48 (d, J=8.4 Hz, 4H), 7.29-7.37 (m, 5H), 6.55 (t, J=7.8 Hz, 1H), 3.63 (s, 4H).

N,N'-((2-fluorophenyl)methylene)bis(2-(4-(trifluoromethyl)phenyl)acetamide) (31). Yield: 66%. $^1$H NMR (400 MHz, DMSO-$d_6$) δ 8.99 (d, J=7.2 Hz, 2H), 7.63 (d, J=7.8 Hz, 4H), 7.46 (d, J=7.8 Hz, 5H), 7.36-7.40 (m, 1H), 7.21 (t, J=7.8 Hz, 2H), 6.74 (t, J=7.8 Hz, 1H), 3.60 (s, 4H).

N,N'-((4-fluorophenyl)methylene)bis(2-(4-(trifluoromethyl)phenyl)acetamide) (32). Yield: 70%. $^1$H NMR (400 MHz, DMSO-$d_6$) δ 8.95 (d, J=8.4 Hz, 2H), 7.63 (d, J=8.4 Hz, 4H), 7.47 d, J=8.4 Hz, 4H), 7.37 (dd, J=5.4, 8.4 Hz, 2H), 7.19 (t, J=8.4 Hz, 2H), 6.51 (t, J=7.8 Hz, 1H), 3.62 (s, 4H).

N,N'-((4-chlorophenyl)methylene)bis(2-(4-(trifluoromethyl)phenyl)acetamide) (33). Yield: 75%. $^1$H NMR (400 MHz, DMSO-$d_6$) δ 8.96 (d, J=7.8 Hz, 2H), 7.63 (d, J=7.2 Hz, 4H), 7.46 (d, J=7.8 Hz, 4H), 7.43 (dd, J=1.8, 8.4 Hz, 2H), 7.34-7.35 (m, 2H), 6.50 (t, J=7.2 Hz, 1H), 3.62 (s, 4H).

N,N'-(p-tolylmethylene)bis(2-(4-(trifluoromethyl)phenyl)acetamide) (34). Yield: 71%. $^1$H NMR (400 MHz, DMSO-$d_6$) δ 8.87 (d, J=8.4 Hz, 2H), 7.63 (d, J=7.8 Hz, 4H), 7.47 (d, J=8.4 Hz, 4H), 7.20 (d, J=8.4 Hz, 2H), 7.15 (d, J=7.8 Hz, 2H), 6.49 (t, J=7.8 Hz, 1H), 3.61 (s, 4H), 2.28 (s, 3H).

N,N'-((4-methoxyphenyl)methylene)bis(2-(4-(trifluoromethyl)phenyl)acetamide) (35). Yield: 76%. $^1$H NMR (400 MHz, DMSO-$d_6$) δ 8.85 (d, J=7.8 Hz, 2H), 7.63 (d, J=7.8 Hz, 4H), 7.47 (d, J=8.4 Hz, 4H), 7.24 (d, J=9.0 Hz, 2H), 6.91 (d, J=8.4 Hz, 2H), 6.48 (t, J=7.8 Hz, 1H), 3.74 (s, 3H), 3.61 (s, 4H).

N,N'-(4-(trifluoromethyl)phenyl)methylene)bis(2-(4-(trifluoromethyl)phenyl)acetamide) (36). Yield: 64%. $^1$H NMR (400 MHz, DMSO-$d_6$) δ 9.08 (d, J=7.2 Hz, 2H), 7.73 (d, J=7.8 Hz, 2H), 7.63 (d, J=7.8 Hz, 4H), 7.56 (d, J=7.8 Hz, 2H), 7.48 (d, J=7.8 Hz, 4H), 6.60 (t, J=7.8 Hz, 1H), 3.35-3.43 (m, 4H).

Synthetic Method 2.

N,N'-(2-phenylethane-1,1-diyl)bis(2-phenylacetamide) (37). To a well stirred suspension of 2-phenylacetamide (540 mg, 4 mmol) in dry DCM (2 mL) was added the 2-phenylacetaldehyde (240 mg, 2 mmol) and trimethylsilyltrifluoromethane sulonate (22 mg, 0.1 mmol). The mixture was vigorously stirred for 12 h at room temperature, diluted with toluene (4 mL), and filtered. The precipitate was washed several times with toluene which was recrystallized with methanol and hexane to give the final product (140 mg, 19%). $^1$H NMR (400 MHz, DMSO-$d_6$) δ 8.45 (d, J=7.6 Hz, 2H), 7.14-7.28 (m, 15H), 5.55 (t, J=7.6 Hz, 1H), 3.39 (s, 4H), 2.93 (d, J=7.2 Hz, 2H). LC-MS (ESI): m/z 373.0 (M+H)$^+$.

N,N'-(3-phenylpropane-1,1-diyl)bis(2-phenylacetamide) (38). Yield: 52%. $^1$H NMR (400 MHz, DMSO-$d_6$) δ 8.45 (d, J=7.6 Hz, 2H), 7.10-7.31 (m, 15H), 5.26 (t, J=7.6 Hz, 1H), 3.38-3.46 (m, 4H), 2.47-2.53 (m, 2H), 1.88-1.94 (m, 2H). LC-MS (ESI): m/z 387.3 (M+H)$^+$.

(E)-N,N'-(3-phenylprop-2-ene-1,1-diyl)bis(2-phenylacetamide) (39). Yield: 18%. $^1$H NMR (400 MHz, DMSO-$d_6$) δ 8.61 (d, J=7.6 Hz, 2H), 7.21-7.37 (m, 15H), 6.41-6.45 (m, 1H), 6.27-6.32 (m, 1H), 6.04-6.09 (m, 1H), 3.44-3.52 (m, 4H). LC-MS (ESI): m/z 385.1 (M+H)$^+$.

N,N'-((4-isopropoxyphenyl)methylene)bis(2-phenylacetamide) (12). Yield: 8.1%. $^1$H NMR (400 MHz, DMSO-$d_6$) δ 8.69 (d, J=7.6 Hz, 2H), 7.18-7.13 (m, 12H), 6.87 (d, J=6.8 Hz, 2H), 6.48 (t, J=8.0 Hz, 1H), 4.58-4.61 (m, 1H), 3.45-3.53 (m, 4H), 1.25 (d, J=6.0 Hz, 6H). LC-MS (ESI): m/z 417.2 (M+H)$^+$.

N,N'-((4-bromophenyl)methylene)bis(2-phenylacetamide) (7). Yield: 71%. $^1$H NMR (400 MHz, DMSO-$d_6$) δ 8.82 (d, J=7.6 Hz, 2H), 7.53-7.56 (m, 2H), 7.21-7.33 (m, 12H), 6.48 (t, J=7.6 Hz, 1H), 3.46-3.54 (m, 4H). LC-MS (ESI): m/z 437.0 (M+H)$^+$.

N,N'-((4-ethoxyphenyl)methylene)bis(2-phenylacetamide) (11). Yield: 30%. $^1$H NMR (400 MHz, DMSO-$d_6$) δ 8.69 (d, J=8.0 Hz, 2H), 7.18-7.31 (m, 10H), 6.88 (d, J=6.4 Hz, 2H), 6.48 (t, J=8.0 Hz, 1H), 3.98-4.03 (m, 2H), 3.45-3.52 (m, 4H), 1.31 (t, J=6.8 Hz, 3H). LC-MS (ESI): m/z 403.1 (M+H)$^+$.

N,N'-(pentane-1,1-diyl)bis(2-phenylacetamide) (40). Yield: 63%. $^1$H NMR (400 MHz, DMSO-$d_6$) δ 8.25 (d, J=8.0 Hz, 2H), 7.19-7.30 (m, 8H), 5.30 (t, J=7.6 Hz, 1H), 3.36-3.44 (m, 4H), 1.56-1.62 (m, 2H), 1.14-1.26 (m, 4H), 0.81 (t, J=7.2 Hz, 3H). LC-MS (ESI): m/z 339.1 (M+H)$^+$.

N,N'-(hexane-1,1-diyl)bis(2-phenylacetamide) (41). Yield: 73%. $^1$H NMR (400 MHz, DMSO-$d_6$) δ 8.25 (d, J=8.0 Hz, 2H), 7.19-7.30 (m, 8H), 5.29 (t, J=7.6 Hz, 1H), 3.39-3.44 (m, 4H), 1.57-1.59 (m, 2H), 1.18-1.23 (m, 6H), 0.82 (t, J=6.8 Hz, 3H). LC-MS (ESI): m/z 353.3 (M+H)$^+$.

N,N'-((3-fluorophenyl)methylene)bis(2-phenylacetamide) (4). Yield: 27%. $^1$H NMR (400 MHz, DMSO-$d_6$) δ 8.83 (d, J=8.0 Hz, 2H), 7.06-7.42 (m, 14H), 6.53 (t, J=7.6 Hz, 1H), 3.47-3.55 (m, 4H). LC-MS (ESI): m/z 377.2 (M+H)$^+$.

N,N'-((4-isopropylphenyl)methylene)bis(2-phenylacetamide) (9). Yield: 15%. $^1$H NMR (400 MHz, DMSO-$d_6$) δ 8.73 (d, J=8.0 Hz, 2H), 7.20-7.32 (m, 14H), 6.51 (t, J=8.0 Hz, 1H), 3.46-3.54 (m, 4H), 2.85-2.89 (m, 1H), 1.19 (d, J=6.8 Hz, 6H). LC-MS (ESI): m/z 401.2 (M+H)$^+$.

N,N'-(2-Phenylethane-1,1-diyl)bis(2-phenylacetamide) (44). To a well stirred suspension of 2-phenylacetamide (540 mg, 4 mmol) in dry dichloromethane (2 mL) was added the 2-phenylacetaldehyde (240 mg, 2 mmol) and trimethylsilyltrifluoromethanesulfonate (22 mg, 0.1 mmol). The mixture was vigorously stirred for 12 h at room temperature, diluted with toluene (4 mL), and filtered. The precipitate was washed several times with toluene which was recrystallized with methanol and hexane to give the final product (560 mg, 76%). $^1$H NMR (400 MHz, DMSO-$d_6$) δ 8.45 (d, J=7.6 Hz, 2H), 7.14-7.28 (m, 15H), 5.55 (t, J=7.6 Hz, 1H), 3.39 (s, 4H), 2.93 (d, J=7.2 Hz, 2H). HPLC-MS (ESI): m/z 373.2 (M+H)$^+$.

N,N'-(3-Phenylpropane-1,1-diyl)bis(2-phenylacetamide) (45). Compound 45 was prepared from 2-phenylacetamide and 3-phenylpropanal using the procedure for compound 44. Yield: 92%. $^1$HNMR (400 MHz, DMSO-$d_6$) δ 8.45 (d, J=7.6 Hz, 2H), 7.10-7.31 (m, 15H), 5.26 (t, J=7.6 Hz, 1H), 3.38-3.46 (m, 4H), 2.47-2.53 (m, 2H), 1.88-1.94 (m, 2H). LC-MS (ESI): m/z 387.3 (M+H)$^+$.

(E)-N,N'-(3-Phenylprop-2-ene-1,1-diyl)bis(2-phenylacetamide) (46). Compound 46 was prepared from 2-phenylacetamide and cinnamaldehyde using the procedure for compound 44. Yield: 88%. $^1$H NMR (400 MHz, DMSO-$d_6$) δ 8.61 (d, J=7.6 Hz, 2H), 7.21-7.37 (m, 15H), 6.41-6.45 (m, 1H), 6.27-6.32 (m, 1H), 6.04-6.09 (m, 1H), 3.44-3.52 (m, 4H). LC-MS (ESI): m/z 385.1 (M+H)$^+$.

N,N'-((4-(Diethylamino)phenyl)methylene)bis(3-phenylpropanamide) (47). Compound 47 was prepared from 3-phenylpropanamide and 4-(diethylamino)benzaldehyde according to the procedure for compound 1. Yield: 66%. $^1$H NMR (400 MHz, CD$_3$OD) δ 8.29-8.30 (m, 2H), 7.17-7.29 (m, 10H), 6.92 (d, J=8.4 Hz, 2H), 6.56 (d, J=8.4 Hz, 2H), 6.46 (t, J=8.0 Hz, 1H), 2.82 (t, J=7.6 Hz, 4H), 2.42-2.47 (m, 4H), 1.07

(t, J=6.8 Hz, 6H). LC-MS (ESI): m/z 458.2 (M+H)$^+$. HRMS (ESI) for $C_{29}H_{36}N_3O_2$(MH$^+$): calcd, 458.2802. found, 458.2795.

N,N'-((4-(Diethylamino)phenyl)methylene)bis(3-phenylacrylamide) (48). Compound 48 was prepared from cinnamamide and 4-(diethylamino)benzaldehyde according to the procedure for compound 1. Yield: 68%. $^1$H NMR (400 MHz, CD$_3$OD) δ 8.68-8.70 (m, 2H), 7.38-7.58 (m, 12H), 7.19 (d, J=8.8 Hz, 2H), 6.79 (d, J=16.0 Hz, 2H), 6.66-6.68 (m, 3H), 3.29-3.35 (m, 4H), 1.08 (t, J=7.2 Hz, 6H). LC-MS (ESI): m/z 454.2 (M+H)$^+$. HRMS (ESI) for $C_{29}H_{32}N_3O_2$ (MH$^+$): calcd, 454.2489. found, 454.2487.

N,N'-((4-(Diethylamino)phenyl)methylene)dibenzamide (49). Compound 49 was prepared from benzamide and 4-(diethylamino)-benzaldehyde according to the procedure for compound 1. Yield: 73%. $^1$H NMR (400 MHz, CD$_3$OD) δ 9.24 (d, J=7.6 Hz, 1H), 7.88-7.93 (m, 4H), 7.81 (d, J=8.8 Hz, 2H), 7.46-7.65 (m, 9H), 7.20 (m, 1H), 3.70-3.81 (m, 4H), 1.17 (t, J=7.2 Hz, 6H). LC-MS (ESI): m/z 402.2 (M+H)$^+$. HRMS (ESI) for $C_{25}H_{28}N_3O_2$ (MH$^+$): calcd, 402.2176. found, 402.2167.

N,N'-((4-(Diethylamino)phenyl)methylene)bis(2-methylpropanamide) (50). Compound 50 was prepared from isobutyramide and 4-(diethylamino)benzaldehyde according to the procedure for compound 1. Yield: 80%. 1H NMR (400 MHz, CD$_3$OD) δ 7.18 (d, J=8.4 Hz, 2H), 6.70-6.73 (m, 2H), 6.56 (s, 1H), 3.35-3.50 (m, 2H), 2.47-2.54 (m, 4H), 1.13-1.16 (m, 12H). LC-MS (ESI): m/z 334.2 (M+H)$^+$. HRMS (ESI) for $C_{19}H_{32}N_3O_2$ (MH$^+$): calcd, 334.2489. found 334.2483.

N,N'-((4-(diethylamino)phenyl)methylene)bis(2,2-dimethylpropanamide) (51). Compound 51 was prepared from pivalamide and 4-(diethylamino)benzaldehyde using method 1. Yield: 77%. $^1$H NMR (400 MHz, DMSO) δ 7.70 (d, J=8.8 Hz, 2H), 7.03 (d, J=8.8 Hz, 2H), 6.62 (d, J=8.8 Hz, 2H), 6.52 (t, J=8.4 Hz, 1H), 3.30-3.33 (m, 4H), 1.12 (s, 18H), 1.05-1.08 (m, 6H). LC-MS (ESI): m/z 262.2 (M+H)$^+$. HRMS (ESI) for $C_{21}H_{36}N_3O_2$ (MH$^+$): calcd, 362.2802. found 362.2795.

N,N'-((4-(diethylamino)phenyl)methylene)dipentanamide (52). Compound 52 was prepared from pentanamide and 4-(diethylamino)benzaldehyde using method 1. Yield: 69%. $^1$H NMR (400 MHz, CD$_3$OD) δ 7.18 (d, J=8.8 Hz, 2H), 6.71 (d, J=8.8 Hz, 2H), 6.58 (t, J=8.4 Hz, 1H), 3.33-3.41 (m, 4H), 2.25 (t, J=7.2 Hz, 4H), 1.58-1.66 (m, 4H), 1.33-1.43 (m, 4H), 1.14 (t, J=7.2 Hz, 6H), 0.95 (t, J=2.8 Hz, 6H). LC-MS (ESI): m/z 362.2 (M+H)$^+$. HRMS (ESI) for $C_{21}H_{36}N_3O_2$ (MH$^+$): calcd, 362.2802. found 362.2792.

N,N'-((4-(diethylamino)phenyl)methylene)dihexanamide (53). Compound 53 was prepared from hexanamide and 4-(diethylamino)benzaldehyde using method 1. Yield: 76%. $^1$H NMR (400 MHz, CD$_3$OD) δ 7.19 (d, J=8.8 Hz, 2H), 6.71 (d, J=8.8 Hz, 2H), 6.58 (t, J=8.4 Hz, 1H), 3.35-3.41 (m, 4H), 2.19-2.26 (m, 4H), 1.61-1.68 (m, 4H), 1.32-1.35 (m, 8H), 1.14 (t, J=6.8 Hz, 6H), 0.94 (t, J=2.8 Hz, 6H). LC-MS (ESI): m/z 390.3 (M+H)$^+$. HRMS (ESI) for $C_{23}H_{40}N_3O_2$ (MH$^+$): calcd, 390.3115. found 390.3108.

N,N'-((4-(diethylamino)phenyl)methylene)dioctanamide (54). Compound 54 was prepared from octanamide and 4-(diethylamino)benzaldehyde using method 1. Yield: 68%. $^1$H NMR (400 MHz, DMSO) δ 8.21 (d, J=8.0 Hz, 2H), 7.07 (d, J=8.8 Hz, 2H), 6.61 (d, J=8.8 Hz, 2H), 6.42 (t, J=8.0 Hz, 1H), 3.29-3.31 (m, 4H), 2.06-2.14 (m, 4H), 1.47-1.50 (m, 4H), 1.08-1.24 (m, 16H), 1.06 (t, J=7.2 Hz, 6H), 0.94 (t, J=7.2 Hz, 6H). LC-MS (ESI): m/z 446.3 (M+H)$^+$. HRMS (ESI) for $C_{27}H_{48}N_3O_2$ (MH$^+$): calcd, 446.3741. found 446.3734.

N,N'-((4-(diethylamino)phenyl)methylene)bis(decanamide) (55). Compound 55 was prepared from decanamide and 4-(diethylamino)benzaldehyde using method 1. Yield: 56%. $^1$H NMR (400 MHz, DMSO) δ 8.99 (d, J=9.6 Hz, 1H), 8.38 (d, J=8.8 Hz, 1H), 6.99 (d, J=8.8 Hz, 2H), 6.58 (d, J=8.4 Hz, 2H), 5.84 (d, J=8.4 Hz, 1H), 3.27-3.30 (m, 4H), 2.33 (t, J=7.2 Hz, 4H), 2.14 (t, J=7.2 Hz, 4H), 1.50-1.55 (m, 4H), 1.24-1.28 (m, 24H), 1.06 (t, J=7.2 Hz, 6H), 0.87 (t, J=7.2 Hz, 6H). LC-MS (ESI): m/z 502.4 (M+H)$^+$.

Scheme 2. General Synthesis of Compounds 56-99.

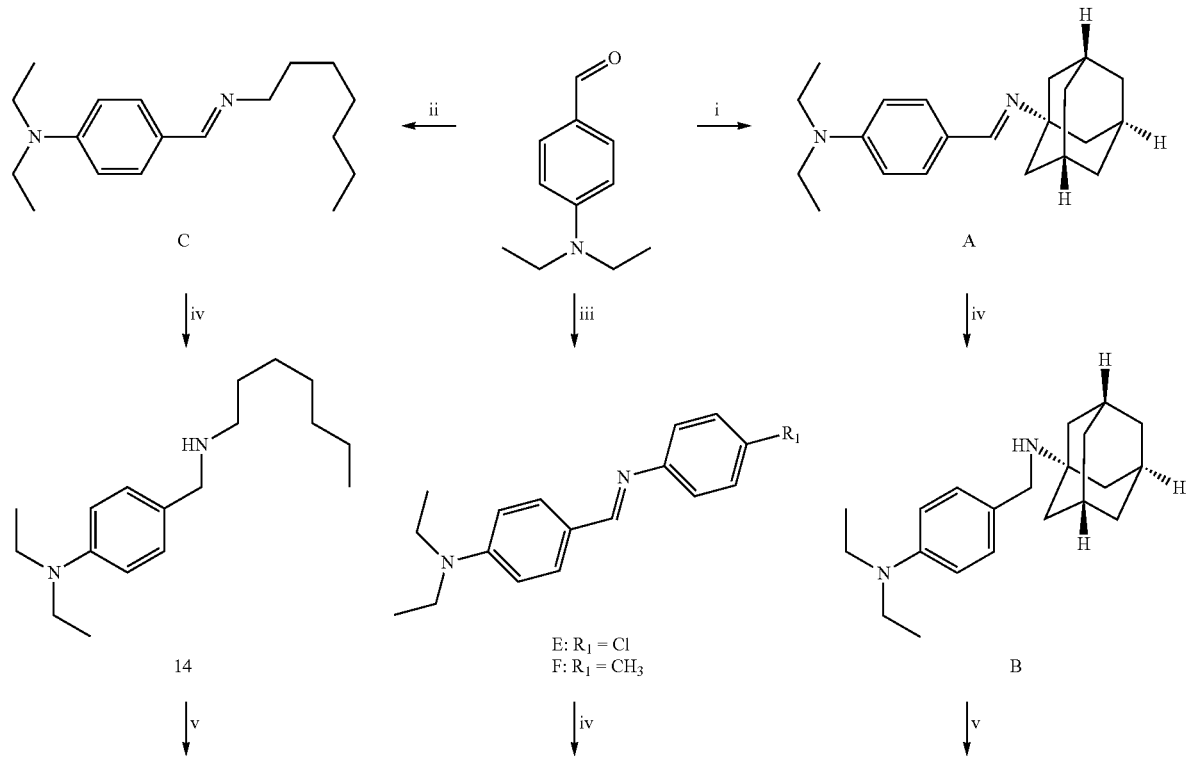

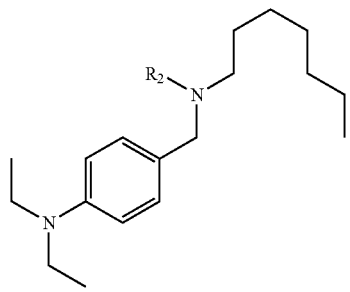

67-80: R₂ = acyl, sulfonyl

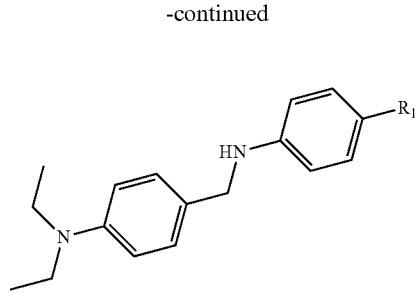

G: R₁ = Cl
H: R₁ = CH₃

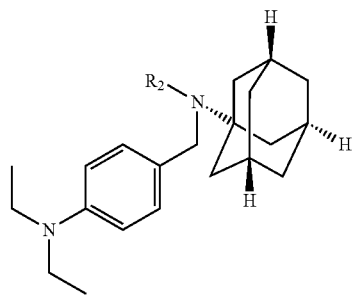

56-66: R₂ = acyl, sulfonyl

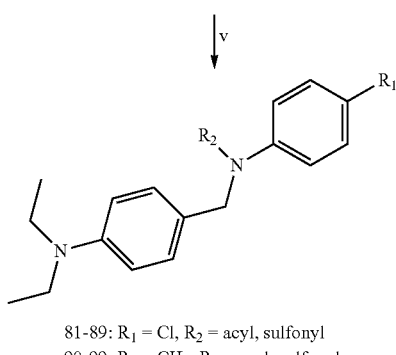

81-89: R₁ = Cl, R₂ = acyl, sulfonyl
90-99: R₁ = CH₃, R₂ = acyl, sulfonyl

[a]Reagents and conditions: (i) adamantan-1-amine, methanol, refluxed, 10 h; (ii) heptan-1-amine, methanol, refluxed, 12 h; (iii) p-toluidine or 4-chloroaniline, methanol, refluxed, 12 h; (iv) NaBH₄, methanol, r.t, 12 h; (v) acyl chloride or sulfonyl chloride, anhydrous DCM, TEA, r.t, 12 h.

The synthetic routes to obtain compounds 55-99 are outlined in Scheme 2 above. The commercially available 4-(diethylamino)benzaldehyde was reacted with adamantan-1-amine in methanol to give A, which, when treated with NaBH₄ gave the secondary amine B. Finally, the coupling reaction between intermediate B and selected acyl chloride or sulfonyl chloride yielded the corresponding compounds 56-66. Taking heptan-1-amine, p-toluidine or 4-chloroaniline as the starting material, the synthesis of target compounds 67-99 was accomplished using a procedure similar to that utilized for preparing compounds 56-66. The final compounds were purified by flash column chromatography.

General Procedure for Synthesis of Secondary Amine Building Blocks.

(3s,5s,7s,E)-N-(4-(Diethylamino)benzylidene)adamantan-1-amine (A). (3s,5s,7s)-adamantan-1-amine hydrochloride (3.75 g, 20 mmol) was added slowly to a solution of 4-(diethylamino)benzaldehyde and methanol (50 mL). The mixture was stirred and refluxed for 12 h. The reaction mixture was cooled to room temperature and the solvent was removed by evaporation in vacuum to give the crude compound A, which was used to the next step without further purification.

(3s,5s,7s)-N-(4-(Diethylamino)benzyl)adamantan-1-amine (B). The crude compound A was dissolved in methanol (50 mL) and NaBH₄ (1.14 g, 30 mmol) was added. The mixture was continued to stir for 12 h at room temperature. The reaction solution was poured into water and extracted with EA. The combined organic layers were washed with water and brine, and then dried over Na₂SO₄. The mixture was filtered and the solvent was evaporated in vacuum. The residue was purified by flash chromatography on silica gel to obtain B (5.8 g, 88%). $^1$H NMR (400 MHz, DMSO-$d_6$) δ 7.13 (d, J=8.0 Hz, 2H), 6.62 (d, J=8.0 Hz, 2H), 3.65 (bs, 1H), 3.42-3.48 (m, 2H), 3.28-3.39 (m, 4H), 2.05-2.07 (m, 3H), 1.58-1.71 (m, 12H), 1.07 (t, J=6.8 Hz, 6H). LC-MS (ESI): m/z 313.2 (M+H)⁺.

4-(((4-Chlorophenyl)amino)methyl)-N,N'-diethylaniline (C). Yield: 78%. $^1$H NMR (400 MHz, DMSO-$d_6$) δ 7.03-7.14 (m, 4H), 6.56-6.62 (m, 4H), 6.19-6.22 (m, 1H), 4.06-4.07 (m, 2H), 3.27-3.34 (m, 4H), 1.06 (t, J=6.8 Hz, 3H). LC-MS (ESI): m/z 289.0 (M+H)⁺.

Synthesis of Compounds 56-99

N-((3s,5s,7s)-Adamantan-1-yl)-N-(4-(diethylamino)benzyl)benzenesulfonamide (56). The intermediate B (328 mg, 1.0 mmol) in dichloromethane (DCM, 5 mL) was chilled in ice with the exclusion of moisture and them triethylamine (122 mg, 1.2 mmol) was added to it. The resulting solution was treated dropwise under stirring with benzenesulfonyl chloride (177 mg, 1.0 mmol) also dissolved in DCM over 30 min at 0° C. and them left overnight at room temperature. The reaction solution was poured into water and extracted with EA. The combined organic layers were washed with water and brine, and then dried over Na₂SO₄. The mixture was filtered and the solvent was evaporated in vacuum. The residue was purified by flash chromatography on silica gel to obtain 56 (400 mg, 85%). $^1$H NMR (400 MHz, DMSO-$d_6$) δ 7.13 (d, J=8.0 Hz, 2H), 6.62 (d, J=8.0 Hz, 2H), 3.65 (bs, 1H), 3.42-3.48 (m, 2H), 3.28-3.39 (m, 4H), 2.05-2.07 (m, 3H), 1.58-1.71 (m, 12H), 1.07 (t, J=6.8 Hz, 6H). LC-MS (ESI): m/z 453.1 (M+H)⁺.

N-((3s,5s,7s)-Adamantan-1-yl)-N-(4-(diethylamino)benzyl)-4-fluorobenzenesulfonamide (57) was prepared in a manner analogous to that for compound 56. Yield: 87%. $^1$H NMR (400 MHz, DMSO-$d_6$) δ 7.87-7.89 (m, 2H), 7.38-7.43 (m, 2H), 7.21 (d, J=8.8 Hz, 2H), 6.64 (d, J=8.8 Hz, 2H), 4.59 (s, 2H), 3.29-3.36 (m, 4H), 1.88-1.93 (m, 9H), 1.42-1.51 (m, 6H), 1.07-1.10 (m, 6H). LC-MS (ESI): m/z 471.0 (M+H)⁺.

N-((3s,5s,7s)-Adamantan-1-yl)-4-chloro-N-(4-(diethylamino)benzyl)benzenesulfonamide (58) was prepared in a manner analogous to that for compound 56. Yield: 92%. $^1$H NMR (400 MHz, DMSO-$d_6$) δ 7.83 (d, J=8.4 Hz, 2H), 7.64 (d, J=8.8 Hz, 2H), 7.21 (d, J=8.8 Hz, 2H), 6.65 (d, J=8.8 Hz, 2H), 4.60 (s, 2H), 3.29-3.37 (m, 4H), 1.88-1.93 (m, 9H), 1.42-1.51 (m, 6H), 1.07-1.11 (m, 6H). LC-MS (ESI): m/z 487.1 (M+H)$^+$.

N-(3r)-Adamantan-1-yl)-N-(4-(diethylamino)benzyl)-4-methoxybenzenesulfonamide (59) was prepared in a manner analogous to that for compound 56. Yield: 89%. $^1$H NMR (400 MHz, DMSO-$d_6$) δ 7.72-7.74 (m, 2H), 7.21 (d, J=8.8 Hz, 2H), 7.07-7.10 (m, 2H), 6.64 (d, J=8.8 Hz, 2H), 4.56 (s, 2H), 3.85 (s, 3H), 3.29-3.33 (m, 4H), 1.87-1.92 (m, 9H), 1.42-1.50 (m, 6H), 1.07-1.10 (m, 6H). LC-MS (ESI): m/z 483.0 (M+H)$^+$.

N-((3s,5s,7s)-Adamantan-1-yl)-N-(4-(diethylamino)benzyl)-4-methylbenzenesulfonamide (60) was prepared in a manner analogous to that for compound 56. Yield: 86%. $^1$H NMR (400 MHz, DMSO-$d_6$) δ 7.70 (d, J=8.4 Hz, 2H), 7.38 (d, J=8.0 Hz, 2H), 7.23 (d, J=8.8 Hz, 2H), 6.65 (d, J=8.8 Hz, 2H), 4.59 (s, 2H), 3.30-3.42 (m, 4H), 2.40 (s, 3H), 1.87-1.92 (m, 9H), 1.40-1.50 (m, 6H), 1.03-1.12 (m, 6H). LC-MS (ESI): m/z 467.2 (M+H)$^+$.

N-((3s,5s,7s)-Adamantan-1-yl)-N-(4-(diethylamino)benzyl)-3-methylbenzenesulfonamide (61) was prepared in a manner analogous to that for compound 56. Yield: 84%. $^1$H NMR (400 MHz, DMSO-$d_6$) δ 7.58-7.62 (m, 2H), 7.42-7.48 (m, 2H), 7.23 (d, J=8.4 Hz, 2H), 6.65 (d, J=8.4 Hz, 2H), 4.60 (s, 2H), 3.30-3.34 (m, 4H), 2.39 (s, 3H), 1.87-1.92 (m, 9H), 1.41-1.50 (m, 6H), 1.07-1.11 (m, 6H). LC-MS (ESI): m/z 467.1 (M+H)$^+$.

N-((3s,5s,7s)-Adamantan-1-yl)-N-(4-(diethylamino)benzyl)-4-isopropylbenzenesulfonamide (62) was prepared in a manner analogous to that for compound 56. Yield: 71%. $^1$H NMR (400 MHz, DMSO-$d_6$) δ 7.72 (d, J=8.0 Hz, 2H), 7.44 (d, J=8.0 Hz, 2H), 7.20 (d, J=8.8 Hz, 2H), 6.64 (d, J=8.8 Hz, 2H), 4.57 (s, 2H), 3.27-3.29 (m, 4H), 2.97-3.01 (m, 1H), 1.89-1.92 (m, 9H), 1.41-1.51 (m, 6H), 1.19-1.24 (m, 6H), 1.08-1.10 (m, 6H). LC-MS (ESI): m/z 495.2 (M+H)$^+$.

N-((3s,5s,7s)-Adamantan-1-yl)-N-(4-(diethylamino)benzyl)cyclohexanecarboxamide (63) was prepared in a manner analogous to that for compound 56. Yield: 89%. $^1$H NMR (400 MHz, CDCl$_3$) δ 7.03 (d, J=8.8 Hz, 2H), 6.68 (d, J=8.8 Hz, 2H), 4.49 (s, 2H), 3.35-3.40 (m, 4H), 2.36-2.42 (m, 1H), 2.22 (d, J=2.4 Hz, 6H), 2.03-2.07 (m, 3H), 1.54-1.76 (m, 14H), 1.18-1.21 (m, 8H). LC-MS (ESI): m/z 423.5 (M+H)$^+$.

N-((3s,5s,7s)-Adamantan-1-yl)-N-(4-(diethylamino)benzyl)octanamide (64) was prepared in a manner analogous to that for compound 56. Yield: 81%. $^1$H NMR (400 MHz, CDCl$_3$) δ 7.05 (d, J=8.4 Hz, 2H), 6.68 (d, J=8.8 Hz, 2H), 4.51 (s, 2H), 3.34-3.39 (m, 4H), 2.25-2.33 (m, 8H), 2.05 (s, 3H), 1.60-1.70 (m, 8H), 1.17-1.31 (m, 14H), 0.88 (t, J=6.8 Hz, 3H). LC-MS (ESI): m/z 439.4 (M+H)$^+$.

N-((3s,5s,7s)-Adamantan-1-yl)-2-(4-chlorophenyl)-N-(4-(diethylamino)benzyl)acetamide (65) was prepared in a manner analogous to that for compound 56. Yield: 79%. $^1$H NMR (400 MHz, CDCl$_3$) δ 7.28 (d, J=8.8 Hz, 2H), 7.14 (d, J=8.4 Hz, 2H), 7.09 (d, J=8.4 Hz, 2H), 6.71 (d, J=8.8 Hz, 2H), 4.50 (s, 2H), 3.62 (s, 2H), 3.36-3.41 (m, 4H), 2.27 (s, 6H), 2.06-2.07 (m, 3H), 1.60-1.70 (m, 6H), 1.21 (t, J=7.2 Hz, 6H). LC-MS (ESI): m/z 465.2 (M+H)$^+$.

N-((3s,5s,7s)-Adamantan-1-yl)-N-(4-(diethylamino)benzyl)-2-phenylacetamide (66) was prepared in a manner analogous to that for compound 56. Yield: 70%. $^1$H NMR (400 MHz, CDCl$_3$) δ 7.29-7.32 (m, 2H), 7.22-7.26 (m, 3H), 7.10 (d, J=8.4 Hz, 2H), 6.71 (d, J=8.8 Hz, 2H), 4.50 (s, 2H), 3.67 (s, 2H), 3.36-3.41 (m, 4H), 2.28 (s, 6H), 2.06-2.07 (m, 3H), 1.60-1.70 (m, 6H), 1.21 (t, J=7.2 Hz, 6H). LC-MS (ESI): m/z 431.1 (M+H)$^+$.

N-(4-(Diethylamino)benzyl)-N-heptyl-4-methylbenzenesulfonamide (67) was prepared in a manner analogous to that for compound 56. Yield: 87%. $^1$H NMR (400 MHz, CDCl$_3$) δ 7.74 (d, J=8.4 Hz, 2H), 7.29-7.33 (m, 2H), 7.09 (d, J=8.8 Hz, 2H), 6.61 (d, J=8.4 Hz, 2H), 4.23 (s, 2H), 3.33-3.38 (m, 4H), 3.06-3.09 (m, 2H), 2.46 (s, 3H), 1.17-1.39 (m, 16H), 1.10-1.15 (m, 3H). LC-MS (ESI): m/z 430.7 (M+H)$^+$.

N-(4-(Diethylamino)benzyl)-N-heptyl-3-methylbenzenesulfonamide (68) was prepared in a manner analogous to that for compound 56. Yield: 89%. $^1$H NMR (400 MHz, DMSO-$d_6$) δ 7.61 (bs, 2H), 7.49-7.50 (m, 2H), 7.06 (d, J=8.4 Hz, 2H), 6.60 (d, J=8.4 Hz, 2H), 4.14 (s, 2H), 3.28-3.33 (m, 4H), 2.96-3.00 (m, 2H), 2.40 (s, 3H), 1.14-1.24 (m, 4H), 1.04-1.08 (m, 12H), 0.81-0.83 (m, 3H). LC-MS (ESI): m/z 432.0 (M+H)$^+$.

N-(4-(Diethylamino)benzyl)-N-heptyl-4-isopropylbenzenesulfonamide (69) was prepared in a manner analogous to that for compound 56. Yield: 81%. $^1$H NMR (400 MHz, CDCl$_3$) δ 7.77 (d, J=8.4 Hz, 2H), 7.37 (d, J=8.0 Hz, 2H), 7.07 (d, J=8.4 Hz, 2H), 6.61 (d, J=8.8 Hz, 2H), 4.24-4.27 (m, 2H), 3.34-3.38 (m, 4H), 2.97-3.32 (m, 3H), 1.10-1.38 (m, 22H), 0.85-0.89 (m, 3H). LC-MS (ESI): m/z 460.2 (M+H)$^+$.

N-(4-(Diethylamino)benzyl)-N-heptyl-4-methoxybenzenesulfonamide (70) was prepared in a manner analogous to that for compound 56. Yield: 89%. $^1$H NMR (400 MHz, CDCl$_3$) δ 7.77-7.80 (m, 2H), 7.08 (d, J=8.4 Hz, 2H), 6.99 (d, J=8.8 Hz, 2H), 6.61 (d, J=8.4 Hz, 2H), 4.22 (s, 2H), 3.90 (s, 3H), 3.33-3.38 (m, 4H), 3.05-3.09 (m, 2H), 1.15-1.40 (m, 16H), 0.83-0.89 (m, 3H). LC-MS (ESI): m/z 448.2 (M+H)$^+$.

N-(4-(Diethylamino)benzyl)-N-heptyl-4-isopropoxybenzenesulfonamide (71) was prepared in a manner analogous to that for compound 56. Yield: 61%. $^1$H NMR (400 MHz, DMSO-$d_6$) δ 7.76 (d, J=8.08 Hz, 2H), 7.13 (d, J=8.8 Hz, 2H), 7.06 (d, J=8.4 Hz, 2H), 6.60 (d, J=8.0 Hz, 2H), 4.10 (s, 2H), 3.86 (s, 3H), 3.28-3.34 (m, 4H), 2.93-2.96 (m, 2H), 1.03-1.23 (m, 20H), 0.79-0.83 (m, 3H). LC-MS (ESI): m/z 475.4 (M+H)$^+$.

N-(4-(Diethylamino)benzyl)-4-fluoro-N-heptylbenzenesulfonamide (72) was prepared in a manner analogous to that for compound 56. Yield: 77%. $^1$H NMR (400 MHz, CDCl$_3$) δ 7.83-7.87 (m, 2H), 7.16-7.21 (m, 2H), 7.05 (d, J=8.4 Hz, 2H), 6.60 (d, J=8.4 Hz, 2H), 4.25 (s, 2H), 3.33-3.38 (m, 4H), 3.08-3.13 (m, 2H), 1.02-1.40 (m, 16H), 0.88-0.92 (m, 3H). LC-MS (ESI): m/z 436.0 (M+H)$^+$.

4-Chloro-N-(4-(diethylamino)benzyl)-N-heptylbenzenesulfonamide (73) was prepared in a manner analogous to that for compound 56. Yield: 83%. $^1$H NMR (400 MHz, CDCl$_3$) δ 7.77 (d, J=8.4 Hz, 2H), 7.48 (d, J=8.4 Hz, 2H), 7.06 (d, J=8.8 Hz, 2H), 6.60 (d, J=8.4 Hz, 2H), 4.25 (s, 2H), 3.33-3.38 (m, 4H), 3.08-3.12 (m, 2H), 1.04-1.42 (m, 16H), 0.88-0.92 (m, 3H). LC-MS (ESI): m/z 450.7 (M+H)$^+$.

N-(4-(Diethylamino)benzyl)-N-heptyl-1-phenylmethanesulfonamide (74) was prepared in a manner analogous to that for compound 56. Yield: 63%. $^1$H NMR (400 MHz, CDCl$_3$) δ 7.35-7.40 (m, 5H), 7.16 (d, J=8.4 Hz, 2H), 6.65 (d, J=8.4 Hz, 2H), 4.05-4.25 (m, 4H), 3.34-3.39 (m, 4H), 2.93-2.96 (m, 2H), 1.03-1.41 (m, 16H), 0.88-0.92 (m, 3H). LC-MS (ESI): m/z 431.2 (M+H)$^+$.

N-(4-(Diethylamino)benzyl)-N-heptylbutane-1-sulfonamide (75) was prepared in a manner analogous to that for compound 56. Yield: 60%. $^1$H NMR (400 MHz, CDCl$_3$) δ 7.19 (d, J=8.4 Hz, 2H), 6.66 (d, J=8.8 Hz, 2H), 4.31 (s, 2H), 3.40-3.40 (m, 4H), 3.14-3.16 (m, 2H), 2.88-2.92 (m, 2H), 1.77-1.81 (m, 2H), 0.88-1.57 (m, 24H). LC-MS (ESI): m/z 398.0 (M+H)$^+$.

N-(4-(Diethylamino)benzyl)-N-heptyl-2-phenylacetamide (76) was prepared in a manner analogous to that for compound 56. Yield: 70%. $^1$H NMR (400 MHz, DMSO-d$_6$) δ 7.25-7.33 (m, 5H), 7.08 (d, J=8.4 Hz, 1H), 6.94 (d, J=8.8 Hz, 1H), 6.65-6.69 (m, 2H), 4.47-4.51 (m, 2H), 3.81-3.82 (m, 2H), 3.31-3.40 (m, 5H), 3.24-3.28 (m, 1H), 1.12-1.29 (m, 16H), 0.88-0.92 (m, 3H). LC-MS (ESI): m/z 396.1 (M+H)$^+$.

2-(4-Chlorophenyl)-N-(4-(diethylamino)benzyl)-N-heptylacetamide (77) was prepared in a manner analogous to that for compound 56. Yield: 65%. $^1$H NMR (400 MHz, DMSO-d$_6$) δ 7.16-7.35 (m, 4H), 7.17 (d, J=8.4 Hz, 1H), 7.08 (d, J=6.4 Hz, 1H), 6.66-6.71 (m, 2H), 4.51 (s, 2H), 3.80-3.81 (m, 2H), 3.35-3.39 (m, 5H), 3.26-3.28 (m, 1H), 1.14-1.67 (m, 16H), 0.89-0.92 (m, 3H). LC-MS (ESI): m/z 428.8 (M+H)$^+$.

N-(4-(Diethylamino)benzyl)-4-(dimethylamino)-N-heptylbenzamide (78) was prepared in a manner analogous to that for compound 56. Yield: 80%. $^1$H NMR (400 MHz, CDCl$_3$) δ 7.37 (d, J=8.4 Hz, 2H), 7.09 (bs, 2H), 6.64-6.66 (m, 4H), 4.55 (s, 2H), 3.32-3.37 (m, 6H), 2.98 (s, 6H), 1.57-1.61 (m, 2H), 1.14-1.28 (m, 14H), 0.86 (t, J=7.2 Hz, 6H). LC-MS (ESI): m/z 424.4 (M+H)$^+$.

N-(4-(Diethylamino)benzyl)-N-heptylcyclohexanecarboxamide (79) was prepared in a manner analogous to that for compound 56. Yield: 91%. $^1$H NMR (400 MHz, CDCl$_3$) δ 6.97-7.06 (m, 4H), 6.59-6.66 (m, 4H), 4.11-4.46 (m, 2H), 3.14-3.37 (m, 6H), 2.47-2.51 (m, 1H), 1.51-1.82 (m, 10H), 1.01-1.49 (m, 16H), 0.84-0.90 (m, 3H). LC-MS (ESI): m/z 387.1 (M+H)$^+$.

N-(4-(Diethylamino)benzyl)-N-heptyloctanamide (80) was prepared in a manner analogous to that for compound 56. Yield: 95%. $^1$H NMR (400 MHz, MeOD) δ 7.02-7.09 (m, 2H), 6.67-6.87 (m, 2H), 4.49 (s, 2H), 3.24-3.41 (m, 6H), 2.43 (t, J=7.2 Hz, 2H), 1.13-1.68 (m, 26H), 0.89-0.95 (m, 3H). LC-MS (ESI): m/z 402.9 (M+H)$^+$.

N-(4-Chlorophenyl)-N-(4-(diethylamino)benzyl)benzenesulfonamide (81) was prepared in a manner analogous to that for compound 56. Yield: 73%. $^1$H NMR (400 MHz, DMSO-d$_6$) δ 7.64-7.73 (m, 5H), 7.32-7.34 (m, 2H), 6.96-7.05 (m, 4H), 6.50 (d, J=7.2 Hz, 2H), 4.63 (s, 2H), 3.23-3.26 (m, 4H), 1.02-1.04 (m, 6H). LC-MS (ESI): m/z 428.9 (M+H)$^+$.

N-(4-Chlorophenyl)-N-(4-(diethylamino)benzyl)-4-fluorobenzenesulfonamide (82) was prepared in a manner analogous to that for compound 56. Yield: 69%. $^1$H NMR (400 MHz, DMSO-d$_6$) δ 7.68-7.70 (m, 2H), 7.44-7.49 (m, 2H), 7.33 (d, J=8.8 Hz, 2H), 7.06 (d, J=8.4 Hz, 2H), 6.96 (d, J=8.8 Hz, 2H), 6.50 (d, J=8.8 Hz, 2H), 4.62 (s, 2H), 3.22-3.28 (m, 4H), 1.02 (t, J=6.8 Hz, 6H). LC-MS (ESI): m/z 446.9 (M+H)$^+$.

4-Chloro-N-(4-chlorophenyl)-N-(4-(diethylamino)benzyl)benzenesulfonamide (83) was prepared in a manner analogous to that for compound 56. Yield: 65%. $^1$H NMR (400 MHz, DMSO-d$_6$) δ 7.70 (d, J=8.8 Hz, 2H), 7.63 (d, J=8.8 Hz, 2H), 7.34 (d, J=8.8 Hz, 2H), 7.07 (d, J=8.8 Hz, 2H), 6.96 (d, J=8.8 Hz, 2H), 6.50 (d, J=8.8 Hz, 2H), 4.62 (s, 2H), 3.22-3.28 (m, 4H), 1.01-1.06 (m, 6H). LC-MS (ESI): m/z 463.0 (M+H)$^+$.

N-(4-Chlorophenyl)-N-(4-(diethylamino)benzyl)-4-methoxybenzenesulfonamide (84) was prepared in a manner analogous to that for compound 56. Yield: 55%. $^1$H NMR (400 MHz, DMSO-d$_6$) δ 7.56 (d, J=8.8 Hz, 2H), 7.32 (d, J=8.8 Hz, 2H), 7.13 (d, J=8.8 Hz, 2H), 7.05 (d, J=8.8 Hz, 2H), 6.96 (d, J=8.8 Hz, 2H), 6.50 (d, J=8.8 Hz, 2H), 4.58 (s, 2H), 3.86 (s, 3H), 3.22-3.27 (m, 4H), 1.02 (t, J=6.8 Hz, 6H). LC-MS (ESI): m/z 459.1 (M+H)$^+$.

N-(4-Chlorophenyl)-N-(4-(diethylamino)benzyl)-4-methylbenzenesulfonamide (85) was prepared in a manner analogous to that for compound 56. Yield: 79%. $^1$H NMR (400 MHz, DMSO-d$_6$) δ 7.31-7.51 (m, 6H), 7.03-7.05 (m, 2H), 6.96 (d, J=8.8 Hz, 2H), 6.49 (d, J=8.8 Hz, 2H), 4.59 (s, 2H), 3.22-3.27 (m, 4H), 2.42 (s, 3H), 1.02 (t, J=6.8 Hz, 6H). LC-MS (ESI): m/z 443.2 (M+H)$^+$.

N-(4-Chlorophenyl)-N-(4-(diethylamino)benzyl)-3-methylbenzenesulfonamide (86) was prepared in a manner analogous to that for compound 56. Yield: 65%. $^1$H NMR (400 MHz, DMSO-d$_6$) δ 7.38-7.53 (m, 4H), 7.32 (d, J=8.4 Hz, 2H), 7.04 (d, J=8.8 Hz, 2H), 6.96 (d, J=8.8 Hz, 2H), 6.50 (d, J=8.8 Hz, 2H), 4.61 (s, 2H), 3.22-3.28 (m, 4H), 2.40 (s, 3H), 1.02 (t, J=6.8 Hz, 6H). LC-MS (ESI): m/z 443.0 (M+H)$^+$.

N-(4-Chlorophenyl)-N-(4-(diethylamino)benzyl)-4-isopropylbenzenesulfonamide (87) was prepared in a manner analogous to that for compound 56. Yield: 89%. $^1$H NMR (400 MHz, DMSO-d$_6$) δ 7.56 (d, J=8.4 Hz, 2H), 7.49 (d, J=8.0 Hz, 2H), 7.32 (d, J=8.8 Hz, 2H), 7.06 (d, J=8.8 Hz, 2H), 6.96 (d, J=8.8 Hz, 2H), 6.50 (d, J=8.8 Hz, 2H), 4.61 (s, 2H), 3.23-3.26 (m, 4H), 2.98-3.05 (m, 1H), 1.25 (d, J=6.8 Hz, 6H), 1.03 (t, J=6.4 Hz, 6H). LC-MS (ESI): m/z 471.1 (M+H)$^+$.

N,2-bis(4-Chlorophenyl)-N-(4-(diethylamino)benzyl)acetamide (88) was prepared in a manner analogous to that for compound 56. Yield: 79%. $^1$H NMR (400 MHz, DMSO-d$_6$) δ 7.44 (d, J=8.4 Hz, 2H), 7.32 (d, J=8.4 Hz, 2H), 7.09-7.14 (m, 4H), 6.91 (d, J=8.8 Hz, 2H), 6.54 (d, J=8.8 Hz, 2H), 4.71 (s, 2H), 3.42 (s, 2H), 3.25-3.31 (m, 4H), 1.05 (t, J=6.4 Hz, 6H). LC-MS (ESI): m/z 442.8 (M+H)$^+$.

N-(4-Chlorophenyl)-N-(4-(diethylamino)benzyl)cyclohexanecarboxamide (89) was prepared in a manner analogous to that for compound 56. Yield: 68%. $^1$H NMR (400 MHz, DMSO-d$_6$) δ 7.44 (d, J=8.4 Hz, 2H), 7.11 (d, J=8.4 Hz, 2H), 6.89 (d, J=8.4 Hz, 2H), 6.55 (d, J=8.4 Hz, 2H), 4.65 (s, 2H), 3.26-3.31 (m, 4H), 2.08 (bs, 1H), 1.36-1.63 (m, 7H), 0.93-1.13 (m, 9H). LC-MS (ESI): m/z 399.4 (M+H)$^+$.

N-(4-(Diethylamino)benzyl)-N-(p-tolyl)benzenesulfonamide (90) was prepared in a manner analogous to that for compound 56. Yield: 80%. $^1$H NMR (400 MHz, DMSO-d$_6$) δ 7.60-7.72 (m, 5H), 7.04 (d, J=8.0 Hz, 2H), 6.96 (d, J=8.8 Hz, 2H), 6.87 (d, J=8.4 Hz, 2H), 6.50 (d, J=8.8 Hz, 2H), 4.60 (s, 2H), 3.23-3.28 (m, 4H), 2.23 (s, 3H), 1.03 (t, J=7.2 Hz, 6H). LC-MS (ESI): m/z 408.9 (M+H)$^+$.

N-(4-(Diethylamino)benzyl)-4-fluoro-N-(p-tolyl)benzenesulfonamide (91) was prepared in a manner analogous to that for compound 56. Yield: 83%. $^1$H NMR (400 MHz, DMSO-d$_6$) δ 7.66-7.68 (m, 2H), 7.43-7.47 (m, 2H), 7.06 (d, J=8.0 Hz, 2H), 6.96 (d, J=8.8 Hz, 2H), 6.89 (d, J=8.4 Hz, 2H), 6.50 (d, J=8.8 Hz, 2H), 4.60 (s, 2H), 3.22-3.30 (m, 4H), 2.23 (s, 3H), 1.02 (t, J=7.2 Hz, 6H). LC-MS (ESI): m/z 427.2 (M+H)$^+$.

4-Chloro-N-(4-(diethylamino)benzyl)-N-(p-tolyl)benzenesulfonamide (92) was prepared in a manner analogous to that for compound 56. Yield: 85%. $^1$H NMR (400 MHz, DMSO-d$_6$) δ 7.67-7.70 (m, 2H), 7.61-7.63 (m, 2H), 7.06 (d, J=8.0 Hz, 2H), 6.96 (d, J=8.8 Hz, 2H), 6.90 (d, J=8.4 Hz, 2H), 6.50 (d, J=8.8 Hz, 2H), 4.60 (s, 2H), 3.22-3.28 (m, 4H), 2.23 (s, 3H), 1.02 (t, J=7.2 Hz, 6H). LC-MS (ESI): m/z 442.8 (M+H)$^+$.

N-(4-(Diethylamino)benzyl)-4-methoxy-N-(p-tolyl)benzenesulfonamide (93) was prepared in a manner analogous to that for compound 56. Yield: 91%. $^1$H NMR (400 MHz, DMSO-d$_6$) δ 7.53-7.56 (m, 2H), 7.11-7.13 (m, 2H), 7.04 (d, J=8.4 Hz, 2H), 6.96 (d, J=8.4 Hz, 2H), 6.88 (d, J=8.4 Hz, 2H), 6.49 (d, J=8.8 Hz, 2H), 4.56 (s, 2H), 3.86 (s, 3H), 3.22-3.27 (m, 4H), 2.23 (s, 3H), 1.02 (t, J=7.2 Hz, 6H). LC-MS (ESI): m/z 439.1 (M+H)$^+$.

N-(4-(Diethylamino)benzyl)-4-methyl-N-(p-tolyl)benzenesulfonamide (94) was prepared in a manner analogous to that for compound 56. Yield: 94%. $^1$H NMR (400 MHz, DMSO-d$_6$) δ 7.50 (d, J=8.0 Hz, 2H), 7.40 (d, J=8.4 Hz, 2H), 7.04 (d, J=8.0 Hz, 2H), 6.96 (d, J=8.8 Hz, 2H), 6.87 (d, J=8.4 Hz, 2H), 6.49 (d, J=8.8 Hz, 2H), 4.57 (s, 2H), 3.22-3.27 (m, 4H), 2.42 (s, 3H), 2.22 (s, 3H), 1.02 (t, J=7.2 Hz, 6H). LC-MS (ESI): m/z 423.0 (M+H)$^+$.

N-(4-(Diethylamino)benzyl)-3-methyl-N-(p-tolyl)benzenesulfonamide (95) was prepared in a manner analogous to that for compound 56. Yield: 72%. $^1$H NMR (400 MHz, DMSO-d$_6$) δ 7.37-7.51 (m, 4H), 7.05 (d, J=8.4 Hz, 2H), 6.96 (d, J=8.4 Hz, 2H), 6.86-6.88 (m, 2H), 6.50 (d, J=8.8 Hz, 2H), 4.59 (s, 2H), 3.22-3.28 (m, 4H), 2.39 (s, 3H), 2.23 (s, 3H), 1.03 (t, J=7.2 Hz, 6H). LC-MS (ESI): m/z 423.4 (M+H)$^+$.

N-(4-(Diethylamino)benzyl)-4-isopropyl-N-(p-tolyl)benzenesulfonamide (96) was prepared in a manner analogous to that for compound 56. Yield: 86%. $^1$H NMR (400 MHz, DMSO-d$_6$) δ 7.54-7.56 (m, 2H), 7.47 (d, J=8.4 Hz, 2H), 7.05 (d, J=8.0 Hz, 2H), 6.96 (d, J=8.4 Hz, 2H), 6.89 (d, J=8.4 Hz, 2H), 6.49 (d, J=8.8 Hz, 2H), 4.58 (s, 2H), 3.22-3.28 (m, 4H), 2.98-3.05 (m, 1H), 2.23 (s, 3H), 1.25 (d, J=7.2 Hz, 6H), 1.02 (t, J=7.2 Hz, 6H). LC-MS (ESI): m/z 450.9 (M+H)$^+$.

N-(4-(Diethylamino)benzyl)-2-phenyl-N-(p-tolyl)acetamide (97) was prepared in a manner analogous to that for compound 56. Yield: 86%. $^1$H NMR (400 MHz, DMSO-d$_6$) δ 7.17-7.27 (m, 5H), 7.05 (d, J=7.2 Hz, 2H), 6.97 (d, J=8.0 Hz, 2H), 6.91 (d, J=8.8 Hz, 2H), 6.54 (d, J=8.8 Hz, 2H), 4.69 (s, 2H), 3.35-3.40 (m, 2H), 3.25-3.31 (m, 4H), 2.30 (s, 3H), 1.05 (t, J=7.2 Hz, 6H). LC-MS (ESI): m/z 387.5 (M+H)$^+$.

2-(4-Chlorophenyl)-N-(4-(diethylamino)benzyl)-N-(p-tolyl)acetamide (98) was prepared in a manner analogous to that for compound 56. Yield: 86%. $^1$H NMR (400 MHz, DMSO-d$_6$) δ 7.31 (d, J=8.4 Hz, 2H), 7.18 (d, J=8.0 Hz, 2H), 7.08 (d, J=8.0 Hz, 2H), 6.98 (d, J=8.0 Hz, 2H), 6.91 (d, J=8.4 Hz, 2H), 6.54 (d, J=8.8 Hz, 2H), 4.68 (s, 2H), 3.35-3.38 (m, 2H), 3.25-3.32 (m, 4H), 2.30 (s, 3H), 1.05 (t, J=7.2 Hz, 6H). LC-MS (ESI): m/z 420.7 (M+H)$^+$.

N-(4-(Diethylamino)benzyl)-N-(p-tolyl)cyclohexanecarboxamide (99) was prepared in a manner analogous to that for compound 56. Yield: 84%. $^1$H NMR (400 MHz, DMSO-d$_6$) δ 7.18 (d, J=8.0 Hz, 2H), 6.94 (d, J=8.0 Hz, 2H), 6.89 (d, J=8.4 Hz, 2H), 6.54 (d, J=8.4 Hz, 2H), 4.63 (s, 2H), 3.26-3.31 (m, 4H), 2.30 (s, 3H), 2.08-2.14 (m, 1H), 1.35-1.62 (m, 8H), 0.86-1.09 (m, 8H). LC-MS (ESI): m/z 379.5 (M+H)$^+$.

Methods and Uses

Inventive compounds that conform to Formulae I, I', II, III, III' and IV are useful for modulating CB2 receptor activity. The endocannabinoid system that is formed of the CB1 and CB2 receptors plays an important physiological role glaucoma, cancer, stroke, pain, neuronal disorders, osteoporosis, multiple sclerosis, and autoimmune disorders. The present invention focuses on the of small molecule therapeutic agents that selectively target and modulate the activity of the CB2 receptor, as well as the use of such compounds to treat multiple myeloma and osteoporosis.

Multiple Myeloma (MM)

CB2 signaling plays an important role in B cell maturation and functions. The observation that CB2 is consistently overexpressed in malignant B cells and MM cells when compared to reactive lymphoid tissue or normal purified B lymphocytes, led to the conclusion that agents capable of selectively targeting CB2 receptor and capable of modulating its activity may play a role in the treatment of MM.

For example, FIG. 1 illustrates higher expression of cannabinoid receptor 2 in various multiple myeloma cells grown in culture using Western blot or RT-PCR analysis. This figure also shows that CB1 is primarily expressed in brain tissue and its expression in MM cells is negligible.

Several compounds according to the present invention were synthesized as described above. Radiometric binding studies using cultured cells expressing CB2 and [$^{35}$S]-GTPγS binding assays were used to demonstrate the CB2 binding ability of compounds in accordance with the invention and to identify whether the inventive Formulae I, II or III compounds were agonist, antagonist or inverse agonists of CB2.

Biological Testing Data

1. Cell Culture and Reagents

Human MM cell lines U266, H929, OPM2, RPMI-8226 and its subline RPMI 8226/LR5 (resistant to melphalan), MM.1 S and its subline MM.1 R (resistant to dexamethasone) were cultured as described earlier. The chemoresistant cell lines were cultured in the presence of melphalan or dexamethasone, and resistance phenotype was confirmed by cell proliferation assays. zVAD-fmk was from Calbiochem (San Diego, Calif., USA). Cannabinoid ligands SR141716 (CB1 inverse agonist), CP55940 (CB1/CB2 agonist), Win55212-2 (CB1/CB2 agonist), SR144528 (CB2 inverse agonist) were provided by NIH-NIDA-NDSP program. The radioligand [$^3$H]-CP55940 used for receptor binding assay was obtained from Perkin-Elmer (Boston, Mass., USA).

2. Biological Assays

Briefly, the bioassay is carried out using the Perkin Elmer 96-well Top Counter. Competition binding assay was used to evaluate the CB receptor binding affinity (K$_i$) of the screened ligands by displacing [$^3$H]CP-55940. The procedure is as follows.

The CB receptor binding affinity (Ki) of the in-silico screened ligands is determined via displacement of [$^3$H]CP-55,940. In competition binding experiments, the tested compound dilutions are carried out in duplicate in TME buffer (25 mM Tris, 5 mM MgCl$_2$, 1 mM EDTA) containing 0.1% (w/v) fatty acid free bovine serum albumin (BSA), pH 7.4. Various concentrations of the tested compound are added in the same volume to 3 nM [$^3$H]CP-55,940. TME buffer and cell membrane preparations expressing CB receptors (5 μg per well) are added to a final volume of 200 μL. For the saturation binding experiments, varying concentrations of [$^3$H]CP-55, 940 (0.05-1.5 nM) with or without 2 μM of unlabeled ligands (CP-55,940) are incubated with the receptor membrane preparations to determine K$_d$ and nonspecific binding. After the binding suspensions are incubated at 30° C. for 1 hr, the reaction is terminated by rapid filtration through microfiltration plates (Unifilter GF/B filterplate, PerkinElmer), followed by 5 washes with ice cold TME buffer containing 0.1% BSA on a Packard Filtermate Harvester (PerkinElmer). The plates are then dried overnight and 30 μl MicroScint 0 scintillation cocktail is added to each well of the dried filter plates. The bound radioactivity is then counted using a Perkin Elmer 96-well TopCounter. The $K_i$ is calculated by using nonlinear regression analysis (Prism 5; GraphPad Software Inc., San Diego, Calif.), with the $K_d$ values for [$^3$H]CP-55,940 determined from saturation binding experiments. This assay is used for determination of the binding affinity parameters ($K_i$) of ligand-receptor interactions for the CB receptor.

A tritiated thymidine incorporation assay was carried out to investigate the effects of CB2 ligands on cell proliferation. U266, RPMI-8226 (3×10$_4$ cells/well), MM.1 S cells (6×10$^4$ cells/well), and their resistant sublines were cultured in 96-well culture plates with or without drugs for 48 hours. DNA synthesis was measured by $^3$H-thymidine uptake as described previously.

3. Compounds of the Invention Inhibit Proliferation of Human MM Cells

Cell-based cAMP assays were used to identify the mode by which the CB2 ligands according to the present invention modulate CB2 receptor. Briefly, cAMP cell-based assays were used to investigate whether a given Formula I, I', II, III, III' or IV compound was an agonist, antagonist, or an inverse agonist of MM cells expressing the CB2 receptor and to measure the anti-MM activity of the compounds of the present invention. Known CB2 agonists, antagonists and inverse agonist were used as positive controls. The data illustrates that compounds of the invention bind tightly to the CB2 receptors with $K_1$ values in the nanomolar range. See Table 3.

TABLE 3A

Compounds And Radioligand Binding Data For Compounds Of Structure

| Compd | $R_1$ | $R_2$ | MW | cLog P | $K_i$ (CB$_2$), nM[b, c] | $K_i$ (CB$_1$), nM[a, d] | SI[e] |
|---|---|---|---|---|---|---|---|
| 1 | H | p-(CH$_3$)$_2$N—C$_6$H$_4$ | 401.50 | 4.04 | 777 | >20,000 | >26 |
| 2 | H | Ph | 358.43 | 3.93 | 9,930 | NT | |
| 3 | H | o-F—C$_6$H$_4$ | 376.42 | 4.08 | 35,330 | NT | |
| 4 | H | m-F—C$_6$H$_4$ | 376.42 | 4.08 | 12,670 | NT | |
| 5 | H | p-F—C$_6$H$_4$ | 376.42 | 4.08 | 10,900 | NT | |
| 6 | H | p-Cl—C$_6$H$_4$ | 392.88 | 4.54 | 3,081 | NT | |
| 7 | H | p-Br—C$_6$H$_4$ | 437.33 | 4.70 | 2,226 | NT | |
| 8 | H | p-CH$_3$—C$_6$H$_4$ | 372.46 | 4.45 | 494 | 109 | |
| 9 | H | p-i-C$_3$H$_7$—C$_6$H$_4$ | 400.51 | 5.18 | 85 | >20,000 | >235 |
| 10 | H | p-CH$_3$O—C$_6$H$_4$ | 388.46 | 3.78 | 783 | >20,000 | >26 |
| 11 | H | p-C$_2$H$_5$O—C$_6$H$_4$ | 402.49 | 4.13 | 1,500 | NT | |
| 12 | H | p-i-C$_3$H$_7$O—C$_6$H$_4$ | 416.51 | 4.55 | 313 | >20,000 | >64 |
| 13 | H | o-CF$_3$—C$_6$H$_4$ | 426.43 | 4.81 | 11,780 | NT | |
| 14 | H | p-CF$_3$—C$_6$H$_4$ | 426.43 | 4.81 | 596 | >20,000 | >34 |
| 15 | H | p-NO$_2$—C$_6$H$_4$ | 403.43 | 3.87 | NB | NT | |
| 16 | H | p-H$_2$N—C$_6$H$_4$ | 373.45 | 2.51 | 12,550 | NT | |
| 17 | H | p-(C$_2$H$_5$)$_2$N—C$_6$H$_4$ | 429.55 | 4.76 | 64 | >20,000 | >313 |
| 18 | H | p-(C$_4$H$_9$)$_2$N—C$_6$H$_4$ | 485.66 | 6.69 | 221 | >20,000 | >90 |
| 19 | H | p-piperidyl-C$_6$H$_4$ | 441.56 | 4.89 | 595 | >20,000 | >34 |
| 20 | H | p-(Benzyl)$_2$N—C$_6$H$_4$ | 553.69 | 7.33 | 203 | >20,000 | >99 |
| 21 | Cl | Ph | 427.32 | 5.14 | NB | NT | |
| 22 | Cl | o-F—C$_6$H$_4$ | 445.31 | 5.29 | 10,850 | NT | |
| 23 | Cl | p-F—C$_6$H$_4$ | 445.31 | 5.29 | NB | NT | |
| 24 | Cl | p-Cl—C$_6$H$_4$ | 461.77 | 5.75 | 154 | >20,000 | >130 |
| 25 | Cl | p-CH$_3$—C$_6$H$_4$ | 441.35 | 5.66 | 462 | >20,000 | >43 |
| 26 | Cl | p-CH$_3$O—C$_6$H$_4$ | 457.35 | 4.98 | 310 | >20,000 | >65 |
| 27 | Cl | o-CF$_3$—C$_6$H$_4$ | 495.32 | 6.02 | 158 | >20,000 | >127 |
| 28 | Cl | p-CF$_3$—C$_6$H$_4$ | 495.32 | 6.02 | 101 | >20,000 | >198 |
| 29 | Cl | p-NO$_2$—C$_6$H$_4$ | 472.32 | 5.08 | NB | NT | |
| 30 | CF$_3$ | Ph | 494.43 | 5.69 | NB | NT | |
| 31 | CF$_3$ | o-F—C$_6$H$_4$ | 512.42 | 5.83 | NB | NT | |
| 32 | CF$_3$ | p-F—C$_6$H$_4$ | 512.42 | 5.83 | NB | NT | |
| 33 | CF$_3$ | p-Cl—C$_6$H$_4$ | 528.87 | 6.29 | NB | NT | |
| 34 | CF$_3$ | p-CH$_3$—C$_6$H$_4$ | 508.46 | 6.20 | NB | NT | |
| 35 | CF$_3$ | p-CH$_3$O—C$_6$H$_4$ | 524.45 | 5.53 | NB | NT | |
| 36 | CF$_3$ | p-CF$_3$—C$_6$H$_4$ | 562.43 | 6.57 | NB | NT | |
| 37 | H | C$_6$H$_5$CH$_2$ | 372.46 | 3.99 | NB | NT | |
| 38 | H | C$_6$H$_5$CH$_2$CH$_2$ | 386.49 | 4.44 | 9,319 | NT | |
| 39 | H | C$_6$H$_5$CH=CH | 384.47 | 4.54 | 5,683 | NT | |
| 40 | H | n-C$_4$H$_9$ | 338.44 | 3.75 | 35,970 | NT | |
| 41 | H | n-C$_5$H$_{11}$ | 352.47 | 4.19 | 18,200 | NT | |
| 42[f, g] | | | | | 2.1 | NT | |
| 43[f, h] | | | | | NT | 10.6 | |
| 44 | H | C$_6$H$_5$CH$_2$ | 372.46 | 3.99 | NB | NB | |
| 45 | H | C$_6$H$_5$CH$_2$CH$_2$ | 386.49 | 4.44 | 9,319 | NB | |
| 46 | H | C$_6$H$_5$CH=CH | 384.47 | 4.54 | 5,683 | NB | |

TABLE 3B

Compounds And Radioligand Binding Data For Compounds Of Structure

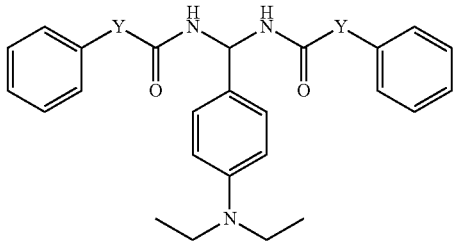

| Compd | Y | MW | cLog P | $K_i$ (CB$_2$), nM[b,c] | $K_i$ (CB$_1$), nM[a,d] | SI[e] |
|---|---|---|---|---|---|---|
| 47 | CH$_2$CH$_2$ | 457.61 | 5.64 | 231 | >20,000 | >93 |
| 48 | CH=CH | 453.58 | 5.80 | 167 | >20,000 | >119 |
| 49 | bond | 401.50 | 4.80 | 688 | >20,000 | >29 |

TABLE 3C

Compounds And Radioligand Binding Data For Compounds Of Structure

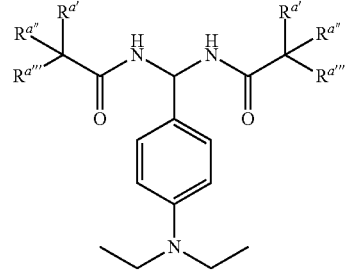

| Compd | R$^{a'}$ | R$^{a''}$ | R$^{a'''}$ | MW | cLog P | $K_i$ (CB$_2$), nM[b,c] | $K_i$ (CB$_1$), nM[a,d] | SI[e] |
|---|---|---|---|---|---|---|---|---|
| 50 | H | CH$_3$ | CH$_3$ | 333.46 | 3.57 | 2636 | NB | |
| 51 | CH$_3$ | CH$_3$ | CH$_3$ | 361.52 | 4.69 | 3553 | NB | |
| 52 | H | H | C$_3$H$_7$ | 361.52 | 4.27 | 182 | >20,000 | >109 |
| 53 | H | H | C$_4$H$_9$ | 389.57 | 5.16 | 25 | >20,000 | >800 |
| 54 | H | H | C$_6$H$_{13}$ | 445.68 | 7.9 | 146 | >20,000 | >136 |
| 55 | H | H | C$_8$H$_{17}$ | 501.79 | 10.0 | 160 | >20,000 | >125 |

TABLE 3D

Compounds And Radioligand Binding Data For Compounds Of Structure

| Compd | R | $K_i$ (CB$_2$), nM[b,c] | $K_i$ (CB$_1$), nM[a,d] | SI[e] |
|---|---|---|---|---|
| B | H | 19950 | NT | 130 |
| 56 | phenylsulfonyl | 84 | 11000 | 130 |
| 57 | 4-fluorophenylsulfonyl | 25 | 4268 | 170 |
| 58 | 4-chlorophenylsulfonyl | 173 | 2033 | 11 |
| 59 | 4-methoxyphenylsulfonyl | 137 | 7300 | 53 |
| 60 | 4-methylphenylsulfonyl | 47 | NB | 425 |

TABLE 3D-continued
Compounds And Radioligand Binding Data For Compounds Of Structure
| Compd | R | $K_i$ (CB$_2$), nM[b,c] | $K_i$ (CB$_1$), nM[a,d] | SI[e] |
|---|---|---|---|---|
| 61 | 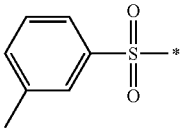 | 19 | 8224 | 432 |
| 62 | 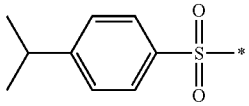 | 457 | NT | |
| 63 | 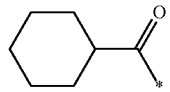 | 35 | NB | >571 |
| 64 | 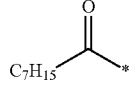 | 638 | NT | |
| 65 | 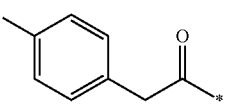 | 38 | NB | >526 |
| 66 | 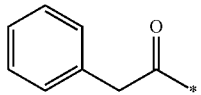 | 60 | NB | >333 |
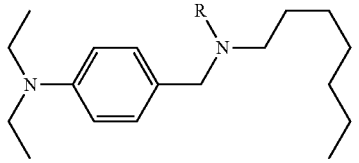
| 67 | 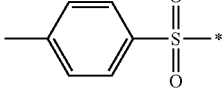 | 2745 | NT | |
| 68 | 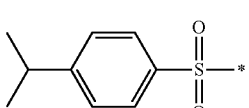 | 2303 | NT | |
| 69 | 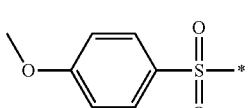 | 13000 | NT | |
| 70 | 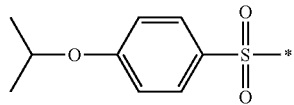 | 5193 | NT | |
| 71 | | NB | NT | |

TABLE 3D-continued
Compounds And Radioligand Binding Data For Compounds Of Structure
| Compd | R | $K_i$ (CB$_2$), nM[b,c] | $K_i$ (CB$_1$), nM[a,d] | SI[e] |
|---|---|---|---|---|
| 72 | 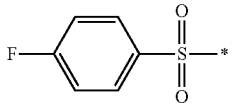 | 1101 | NT | |
| 73 | 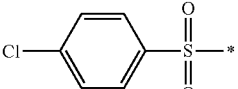 | 6740 | NT | |
| 74 | 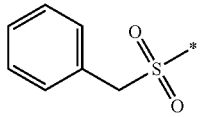 | 273 | NT | |
| 75 | 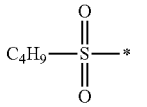 | 680 | NT | |
| 76 | 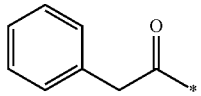 | 1312 | NT | |
| 77 | 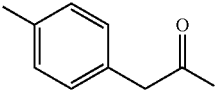 | 696 | NT | |
| 78 |  | 1280 | NT | |
| 79 | 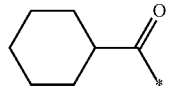 | 212 | NT | |
| 80 | 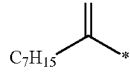 | NB | NT | |
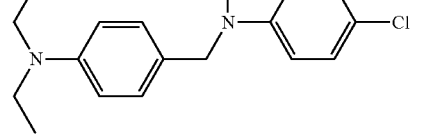
| G | H | 6741 | NT | |
|---|---|---|---|---|
| 81 | 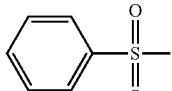 | 20 | 1773 | 88 |
| 82 | 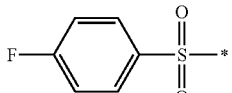 | 73 | 1126 | 15 |

TABLE 3D-continued
Compounds And Radioligand Binding Data For Compounds Of Structure
| Compd | R | $K_i$ (CB$_2$), nM[b,c] | $K_i$ (CB$_1$), nM[a,d] | SI[e] |
|---|---|---|---|---|
| 83 | 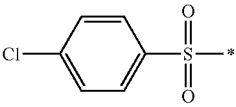 | 36 | 6617 | 183 |
| 84 | 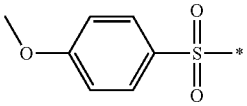 | 14 | NB | >1,428 |
| 85 | 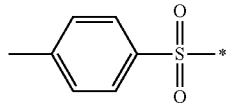 | 37 | 137 | 3.7 |
| 86 | 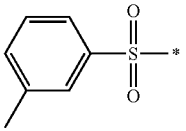 | 2.8 | 866 | 309 |
| 87 | 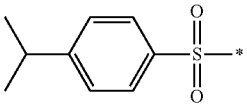 | 222 | NT | |
| 88 | 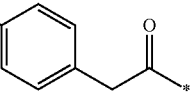 | 136 | NB | 147 |
| 89 | 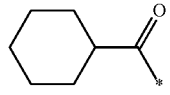 | 164 | NB | 121 |
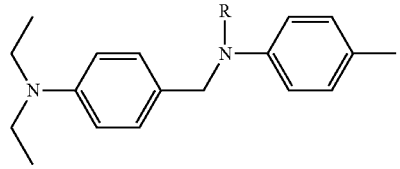
| 90 | 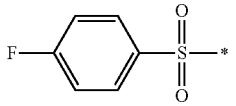 | 3.4 | 514 | 151 |
| 91 | 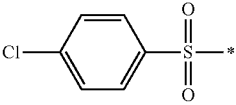 | 5.6 | 858 | 153 |
| 92 | 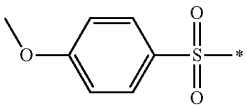 | 3.0 | 412 | 137 |
| 93 | | 0.5 | 1297 | 2594 |

TABLE 3D-continued

Compounds And Radioligand Binding Data For Compounds Of Structure

| Compd | R | $K_i(CB_2)$, nM[b,c] | $K_i(CB_1)$, nM[a,d] | SI[e] |
|---|---|---|---|---|
| 94 | 4-methylphenylsulfonyl | 5.4 | 437 | 80 |
| 95 | 3-methylphenylsulfonyl | 5.8 | 218 | 37 |
| 96 | 4-isopropylphenylsulfonyl | 4.3 | 3365 | 782 |
| 97 | phenylacetyl | 72 | NB | >277 |
| 98 | 4-chlorophenylacetyl | 107 | 3200 | 29 |
| 99 | cyclohexylcarbonyl | 222 | 202 | 0.9 |

[a,b]Binding affinities of compounds for $CB_1$ and $CB_2$ receptor were evaluated using [$^3$H]CP-55,940 radioligand competition binding assay.
[c]NB no binding, $K_i > 20,000$ nM.
[d]NT = not tested.
[e]SI: selectivity index for $CB_2$, calculated as $K_i(CB_1)/K_i(CB_2)$ ratio.
[f]The binding affinities of reference compounds were evaluated in parallel with compounds 1-99 under the same conditions.
[g]$CB_2$ reference compound SR 144528.
[h]$CB_1$ reference compound SR 141716.

Figure 2:
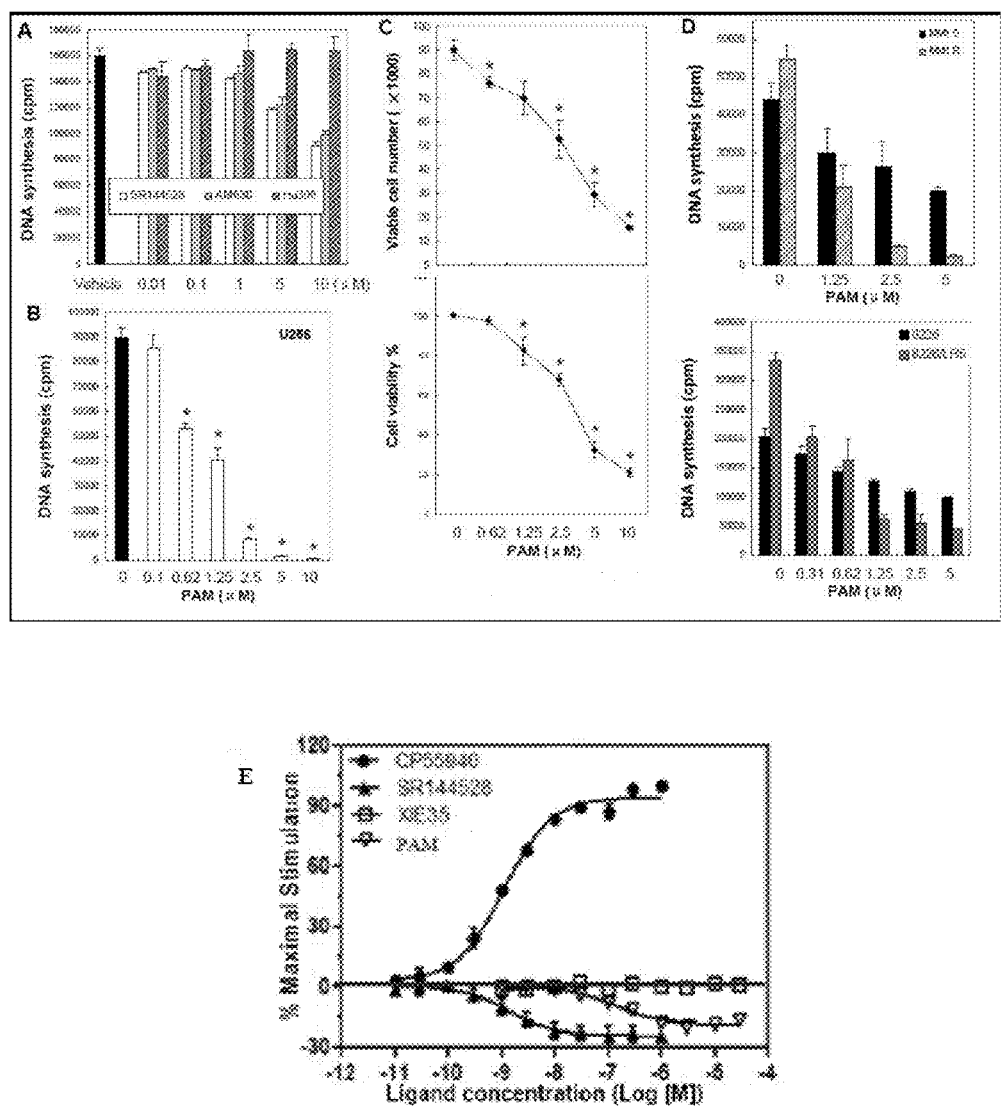
FIG. 2. Inhibitory effects of CB2 ligands on human MM cell growth. Human MM cell U266 ($3 \times 10^4$ cells per well in 96-well plate) was exposed to the known CB2 ligands (A) or PAM (B) at indicated concentrations (0-10 µmol/L) for 48 h. Cell proliferation was measured by [$^3$H]-thymidine uptake assay as described in Materials and Methods. (C) U266 cells ($3 \times 10^4$ per well in 96-well plate) were treated with PAM at indicated doses for 48 h. Cell viability and the viable cell number per well were determined using trypan blue exclusion assay. (D) Human chemoresistant myeloma cell lines MM.1R (dexamethasone), RPMI-8226/LR5 (melphalan) and their respective parent cells MM.1S and RPMI-8226 were exposed to PAM for 48 h. Cell proliferation was measured by $^3$H-thymidine incorporation. The data presented are the mean±SD of at least 3 independent measurements. (E) [$S^{35}$]-GTPγS binding assay of different ligands on human CB2 receptor expressed in CHO cells.

The above compounds in Table 3, however, showed very poor to no binding activity to the CB1 receptor, thus illustrating the selectivity for CB2. FIG. 2A shows the dose dependent inhibition of DNA synthesis in MM cells by the known CB2 selective inverse agonists (SR144528 and AM630) and a known CB2 selective agonist (Hu308) while FIG. 2B illustrates dose dependent inhibition of DNA synthesis in MM cells using a representative compound (1) according to the present invention.

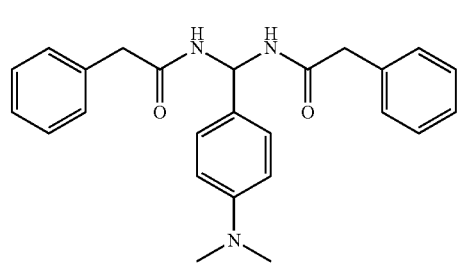

(1)

As demonstrated in FIG. 2A, the known inverse agonist had a modest activity in inhibiting DNA synthesis in MM cells, while the known agonist Hu308 showed no effect even at a concentration as high as 10 μM. In contrast, compound (1), showed potent inhibition of DNA synthesis in MM cells a dose-dependent manner ($IC_{50}$: 1.25 μM). c-AMP studies showed this compound to be an inverse agonist of CB2. See FIG. 2C. It was surprising to discover that compound (1) selectively inhibited the growth of two human chemoresistant myeloma cell lines MM.1 R, resistant to dexamethasone and RPMI-226/LR5 resistant to melphalan with $IC_{50}$ values in the range of about 0.6 to 1.2 μM. However, no growth inhibitory effect was seen for their respective parent cells MM.1S and RPMI-8226.

Since drug resistance is a prevalent problem in multiple myeloma clinical treatment, the ability of compounds according to this invention to overcome chemoresistance of MM cells against conventional drugs such as dexamethasone or melphalan provides an unexpected advantageous benefit in MM treatment. The present inventors have hypothesized that the cell inhibitory activity of the inventive compounds is due to their ability to activate apoptotic processes. Biological studies by the inventors have shown that while mitogen-activated protein kinase (MAPK) family members activated in response to cell stress are crucial for triggering apoptosis, are not up regulated in MM cells treated with compound (1).

Further studies revealed that compound (1) did not have any effect on H2A.X phosphorylation that is critical for DNA damage and apoptosis through sustained activation of JNK. However, endoplasmic reticulum (ER) stress-induced transcription factor, CHOP, was transiently upregulated, which promoted upregulation of CHOP-targeted gene death receptor (DR) 5a, but not death receptor-4 (DR4). Compound (1) also altered certain proteins that are known to play a role in the cell-growth cycle. For instance, contacting cells with various concentrations of compound (1), showed that while number of cells in the $G_0$-$G_1$ phase does not change, the number of cells in the S-phase and those in the G2-M phase decreased in a dose dependent manner. To further explore this observation, the present inventors investigated the effect of compound (1) on several proteins involved in cell G2-M phase transition. In vitro studies indicate that compound (1) prevents the tyrosine phosphatase Cdc25C from activating cyclin-B bound Cdc2 that is responsible for triggering mitosis and G1 to S phase and G2 to M phase cell transitions.

Figure 3:
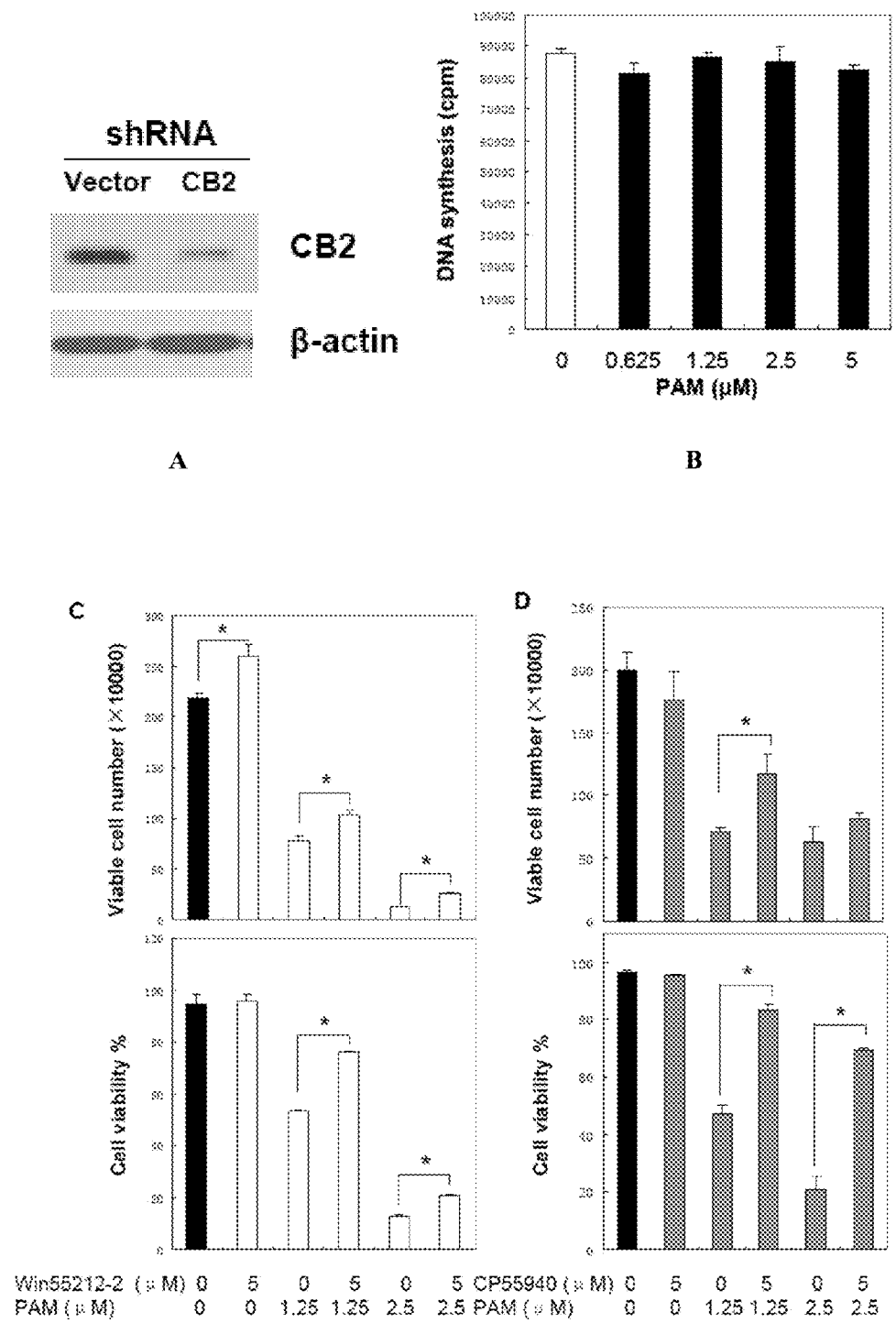
FIG. 3. Inhibitory activity of PAM (compound (1)) in CB2 knockdown or agonist treated cells. (A) CB2 gene silencing in MM1.S cells confirmed by Western blot with CB2antibody. (B) Human MM1.S cells expressing shRNA vector or expressing the specific shRNA against human CB2 were treated with vehicle control (white column), or the indicated concentrations of PAM (black column) for 48 h. Cell proliferation was measured by [$^3$H]TdR uptake. (C) and (D) Human U266 cells ($4 \times 10^5$ cells/well, 24 well plate) were treated with PAM in the absence or presence of CB2 agonist Win55212-2, or CP55940 for 48 h. The cell viability and the viable cells/well were determined using trypan blue exclusion assay.

Taken together, the biological data indicates that compound (1) negatively regulates myeloma cell cycle transitions by modulating the expression and/or activity of various proteins that are known to be important for cell cycle phase transitions, which ultimately result in cell growth inhibition and cell death. The role of CB2 in mediating the inhibition of MM cell growth was studied using compound (1) as an exemplary compound according to the present invention. As illustrated by Western blot analysis (FIGS. 3A and 3B), a stable knockout of CB2, largely abrogated the anti-MM activity of compound (1), suggesting a direct role for the cannabinoid receptor 2 in MM cell death. Pretreatment of MM cells with known agonists Win55212-2 or CP55940 and subsequent contact of these cells with compound (1) showed that pretreatment with a CB2 specific agonist attenuated compound (1) mediated inhibition of MM cell growth demonstrating that the CB2 receptor is a mediator of MM scell death. See FIGS. 3C and 3D. The inventors also compared the CB2 receptor modulatory activity of several known CB2 ligands to PAM (compound (1)). See, e.g., FIG. 2E. Surprisingly, the present inventors discovered that PAM is an inverse CB2 receptor agonist.

The above results and data illustrated in the figures illustrate that compounds that conform to Formulae I, I', II, III, III' and IV are a novel class of candidate therapeutics for treating multiple myeloma.

Osteoporosis

In a further embodiment of the invention, Formulae I, I', II, III, III' and IV compounds are candidate therapeutics for treating a patient or subject suffering from osteoporosis and in need of treatment. The present inventors surprisingly found that compounds according to the present invention suppress osteoclast activity while enhancing the activity of osteoblasts. The inventive compounds, therefore, provide a two pronged therapeutic approach to the treatment of osteoporosis, which differs from conventional therapeutic regimens that rely on inhibition of osteoclast activity to treat osteoporosis.

Using in vitro cell based binding assays, c-AMP regulation and/or $^{35}$S-GTP-γS binding assays described above, the present inventors tested the ability of compound (1) to inhibit osteoclast activity and prevent bone loss either alone or in combination with the clinically approved drug Zoledronic in mouse OVX osteoporosis models. Recent data indicate that compound (1) selectively perturbs CB2 receptor and has exhibits anti-osteoclast activity on both primary mouse and human bone marrow (BM) preosteoclasts. Compound (1) was also found to be non-toxic when administered at concentrations as high as 1 µM.

Figure 4:
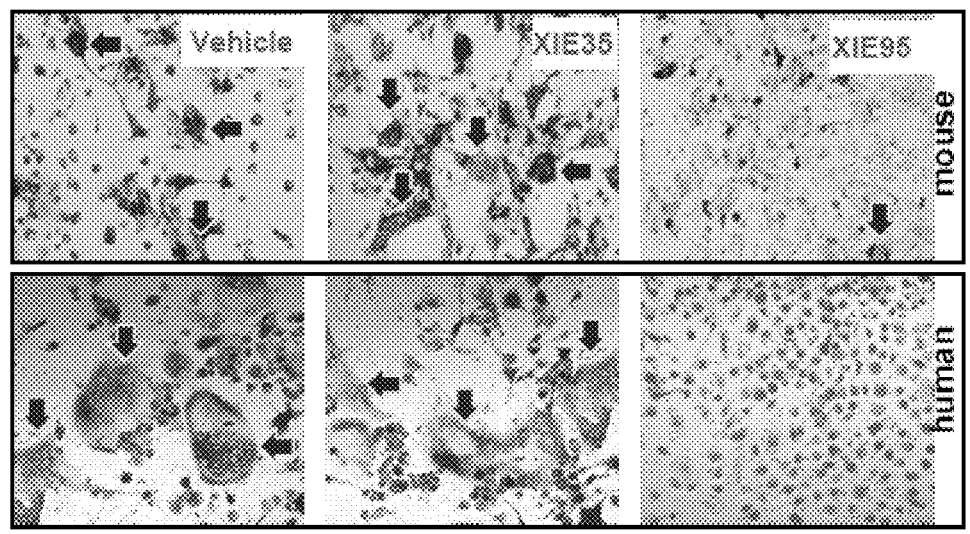
FIG. 4. Effects of XIE35 and compound (1) on RANKL-induced osteoclast formation in bone marrow mononuclear cells (MNC). Upper panel: Murine bone marrow MNCs ($1 \times 10^5$ per well) were isolated by separation on Ficoll-Hypaque gradients as described previously and cultured in the presence of rmRANKL (12.5 ng/mL) plus rhM-CSF (10 ng/ml), and drug vehicle, XIE35 (1 µM) or compound (1) (1 µM) was added to appropriate wells. Half-medium change was performed every other day using drug-containing media where appropriate. After 5 days, the cells were fixed and stained for TRAP activity using a TRAP-staining kit (Sigma-Aldrich) according to the manufacturer's instructions. Lower panel: Human bone marrow MNCs ($1 \times 10^5$ per well) were treated with rhRANKL (50 ng/ml) plus rhM-CSF (10 ng/ml), and the respective compounds as described above. After three weeks, differentiation into OCLs was assessed by staining with monoclonal antibody 23c6 using a Vectastatin-ABC-AP kit (Vector Laboratories). The antibody 23c6, which recognizes CD51/61 dimer constituting the OCL vitronectin receptor, was kindly provided by the Bone Biology Center of our university. Images were obtained with an Olympus IX70 microscope. Arrows designate the typical multinucleated osteoclasts with 3 or more nuclei.

FIG. 4 illustrates the anti-osteoclast activity of compound (1). Briefly, this figure compares the inhibitory effects of compound (1) and a known CB2 antagonist (XIE-35), from the inventors laboratory on RANKL-induced osteoclast formation in bone marrow mononuclear cells. It is clear that XIE-35 exerts a weak inhibitory effect on RANKL/M-CSF induced osteoclast formation as shown by the presence of numerous osteoclasts (arrows). In contrast, compound (1) exerts strong anti-osteoclast effect completely blocking osteoclast formation suggesting a more favorable spatial orientation that enhances this compounds interactions with appropriate amino acid residues in the CB2 receptors ligand binding pocket. As stated above CB2 is highly expressed on osteoclasts and is believed to play a role in osteoclast formation, maturation, and modulate processes that are involved in bone resorption.

As a first step in evaluating the therapeutic potential of compounds of the present invention as candidate therapeutics for treating osteoporosis, the present inventors will conduct studies directed to measuring the ability of these CB2 ligands inhibit osteoclast (OCL) formation and prevent bone resorption as further explained below.

a. Mouse OCL Formation and Bone Resorption Using Marrow Cells and Preosteoclast Cell Line RAW264.7

Briefly, bone marrow (BM) cells will be flushed from the long bones of 4-month-old mice, plated onto petri dishes, and incubated for 48 h in the presence of M-CSF (100 ng/ml). Nonadherent erythrocytes will be removed, and the adherent cells will be washed with PBS and resuspended in culture medium. The resulting M-CSF-dependent bone marrow macrophages cells will be plated onto 96-well plates ($5 \times 10^4$ cells per well) in 100 µl α-MEM containing 10% FBS, antibiotics, rhM-CSF (10 ng/ml), and rmRANKL (15 ng/ml), with or without a Formulae I, II or III compound and inhibition of osteoclast formation by compounds of the invention will be determined fixing the cells and staining the fixed cells with a TRAP staining kit (Sigma-Aldrich) according to the manufacturer's instructions.

The positively stained cells that contain three or more nuclei will be counted as osteoclasts. Mouse OCL formation using RAW264.7 cells ($4 \times 10^3$/well) will be conducted using the similar procedures. To perform bone resorption pit assay, murine M-CSF-dependent marrow cells ($2 \times 10^5$/well) will be seeded on the dentin slices in 96-well plate and treated as above for three weeks. The presence of osteoclasts on dentin slices will be confirmed by TRAP staining and bone resorption lacunae will be stained with hematoxylin.

b. Human Osteoclast Maturation and Function (Bone Resorption Assay)

This assay will measure the effects of our CB2 ligands on human OCL formation and activity. Briefly, nonadherent BM mononuclear cells ($10^5$ cells/well) will be seeded in 96-well plates in α-MEM containing 20% horse serum, 10 ng/ml rhM-CSF, and 50 ng/ml rhRANKL, in the presence or absence of CB2 ligands. Half-media changes will be carried out twice a week where appropriate. Differentiation into OCLs will be assessed by staining with monoclonal antibody 23c6 that recognizes CD51/61 dimer constituting the OCL vitronectin receptor, using a Vectastatin-ABC-AP kit.

OCL number per well, nuclei per OCL, and OCL size will be counted and measured using an inverted microscope and SPOT software. For bone resorption, non-adherent marrow cells ($10^5$/well) will be seeded on the dentin slices in 96-well plate and treated as above for four weeks. Bone resorption lacunae will be stained with hematoxylin. All these tests will be conducted using previously published protocols from the inventors [28].

c. Exploration of the Cellular Pathways and Molecular Mechanisms by which the CB2 Ligands Exhibit Inhibitory Effects on OCL.

To investigate the molecular mechanism for the anti-osteoclast activity of compounds encompassed by the present invention, granulocyte macrophage colony forming units (CFU-GM) cells that are known to be committed to osteoclast (OCL) precursor cell will be plated at a cell density of $5 \times 10^4$/well in 96-well culture plates in the presence of a-MEM medium containing 10% FCS and 100 pg/ml GM-CSF.

Cells will be incubated with an exemplary Formulae I, II or III compound at one or more dose for 48 h. Control wells containing cells but no test compound will also be maintained under identical tissue culture conditions. Cells will be pulsed with $[^3H]$-TdR 37 kBq/well during the last 8 h of culture, harvested onto glass-fiber filter mats using an automatic cell harvester, and counted using a beta plate scintillation counter. Thymidine uptake will be measured as described in the literature and the data will be analyzed and presented graphically as counts per minute (CPM).

Furthermore, given that compounds that conform to Formulae I, II or III are selectivity and tight-binding ligands of CB2 receptor, these compounds are valuable chemical probes for elucidating the signal pathways that are important in the onset and progression of osteoporosis. Recent studies have demonstrated the high expression of cannabinoid receptor CB2 on osteoclasts. In view of the immune monocyte origin of osteoclasts, targeting CB2 receptor has been proposed to regulate the ratio of activated osteoclast to osteoblast, which is critical for the seizure of bone loss and pathological fractures in osteoporosis induced by aging or cancers. See for example, Ofek O, et al. *Proc Natl Acad Sci USA.* 2006; 103:696-701; Idris A I, et al. *Drug News Perspect.* 2008; 21:533-40; and Bab I A. *Ann N Y Acad. Sci.* 2007; 116:414-22.

The effect of Formulae I, I', II, III, III' and IV compounds on differentiation and activity of osteoblasts will also be investigated. Three kinds of experiments: alkaline phosphatase (ALP) activity (an osteoblast differentiation marker), expression of osteoblast related genes (Bsp, Ocn and Runx2) and transactivation of osteoblast-specific Og2 (mouse osteocalcin gene 2), and mineralization assay will be used for this study.

To identify specific genes associated with osteoblast development MC3T3-E1 preosteoblastic cells MC-4 will be cultured in α-MEM containing ascorbic acid (50 μg/ml) for 6 days. Cells will be incubated with an exemplary Formulae I, II or III compound at one or more dose for 48 h. Control wells containing cells but no test compound will also be maintained under identical tissue culture conditions. Total RNA will be isolated and analyzed by quantitative real-time (RT)-PCR using specific primers for Bsp (bone sialoprotein), Ocn (osteocalcin), and Runx2 mRNAs, which are normalized to Gapdh mRNA.

In a separate experiment, MC-42 cells that are stably transfected 1.3-kb Og2 (mouse osteocalcin gene 2) promoter driving expression of a firefly luciferase gene, will be plated in 35-mm plates and cultured in α-MEM-containing ascorbic acid (50 μg/mL) for 15 days. Cells will be incubated with an exemplary compound of the invention at one or more dose for 24 hours. Following incubation, cells are harvested and ssayed for luciferase and ALP activity. The results were normalized to total protein content of the sample.

d. Mineralization Assay

To determine the effect of exemplary Formulae I, I', II, III, III' and IV compounds on the mineralization potential of cells in culture, MC-42 cells will grown in culture as described above for 15 days. Inorganic phosphate will be added to a final concentration of 5.0 mM in the presence or absence of a fixed concentrations of a Formulae I, I', II, III, III' and IV compound for 48 hours. Following incubation, cells will be stained using the von Kossa method and imaged by direct scanning of the mineralization dish using the ScanMaker 9800 XL as previously described.

e. In Vivo Studies

Based on the results from ex-vivo studies, compounds identified as having potent CB2 modulatory effects will be evaluated in the OVX mouse model using 25 μg zoledronic acid (ZOL, s.c., Novartis) as a positive control. Briefly, ovariectomized (OVX) C57-BL6 mice (8-wk-old female, Charles River Lab., Wilmington, Mass.) will be divided into 5 groups, (i) sham group; (ii) OVX+vehicle; (iii) OVX+ZOL 25 μg; (iv) OVX+CB2 ligand (low dose, ip); and (v) OVX+CB2 ligand (high dose, ip for each test compound), with ten (10) mice per group. Dosing with exemplary Formulae I, I', II, III, III' and IV compounds will be commenced on day six (6) after ovariectomy or sham ovariectomy and dosing will be continued for four weeks. At the end of the four week study, tibial bone mineral density will be measured for each mouse in the test and sham groups by microcomputed tomography (micro-CT). Additionally, the osteoclast forming capacity will be evaluated using bone marrow from treated and untreated mice. Results from the in vivo study will be used to advance certain potent compounds to more advanced clinical trials.

f. Osteoclast Formation Bioactivity

Figure 5:
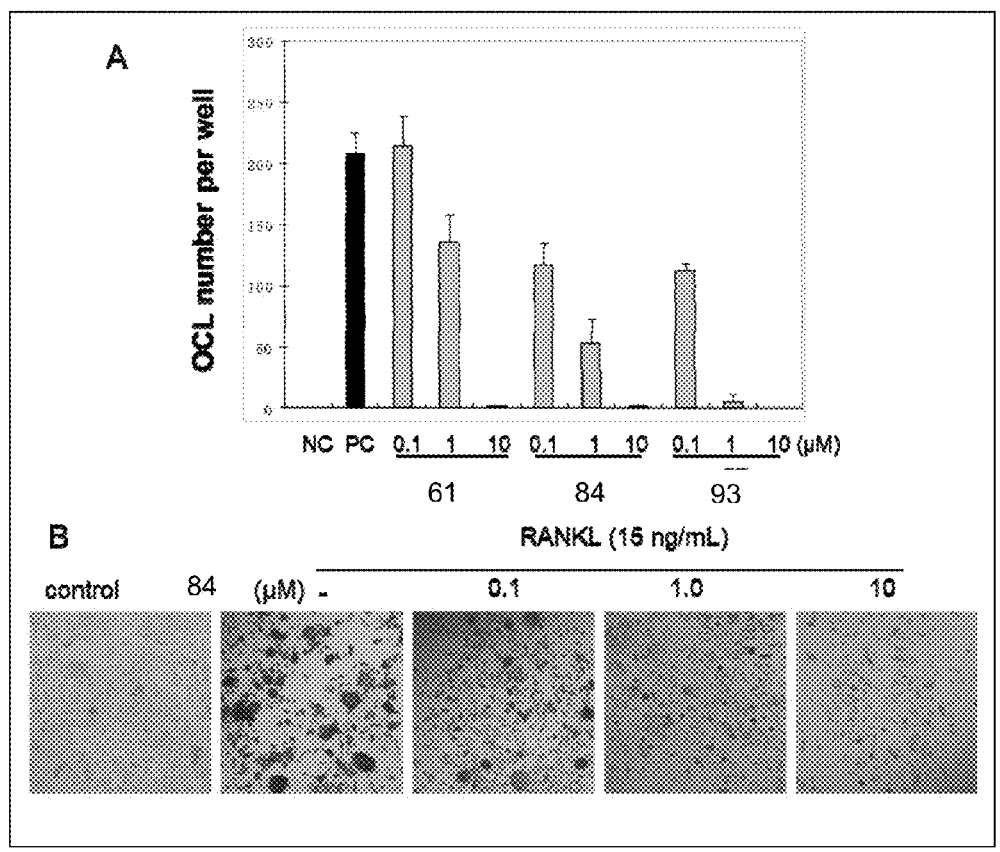
FIG. 5. Anti-osteoclastogenesis activity of exemplary compounds. (A) Compounds 61, 84 and 93 inhibit RANKL-induced osteoclastogenesis in a dose-dependent manner. RAW 264.7 cells ($3 \times 10^3$ cells/well) were treated with or without RANKL (15 ng/mL), followed by addition of the indicated concentrations of 61, 84 and 93 for 5 days and stained for TRAP expression. The data are the mean of three experiments carried out in triplicate. The bar indicates the SD. (B) Photographs of cells in the test of compound 93 (original magnification 100×).

A number of compounds according to the invention were selected as representative candidates to be evaluated against RANKL-induced osteoclast differentiation on RAW 264.7 cells. RAW 264.7 is a mouse monocytic cell line that is used as a standard osteoclast differentiation model. As shown in FIG. 5, the inventors tested the effect of these candidates on osteoclast (OCL) formation using RAW 264.7 cells. Each ligand that was tested induced a concentration-dependent inhibition of osteoclastogenesis and all of the tested compounds generally showed strong potency in suppressing OCL formation at 10 μM, with inhibition rates of >95%.

Compounds 84 and 93 also showed good inhibition activity at low dose of 1 μM (FIG. 5). Meanwhile, these results indicated that the inhibition activities are consistent with the $CB_2$ binding affinities. Especially, compound 93 showed the strongest inhibition activity, with inhibition rates of 46%, 97%, and 100% at 0.1, 1, and 10 μM, respectively.

The same techniques demonstrated that compound 17 showed strong inhibition activity, with inhibition rates of 72%, 79%, and 84% at 0.1, 1, and 10 μM, respectively.

Cytotoxicity Studies Using Normal Human Cells

The compounds of the invention showed promising inhibition activity with respect to osteoclastogenesis. To examine whether the impaired osteoclastogenesis in the presence of PAM compounds is due to their cell toxicity, the inventors investigated the cytotoxicity profile of PAM compounds on normal human cells.

Peripheral blood was drawn in a heparinized syringe from healthy fasting volunteers who had been without medication for at least 2 weeks. The peripheral blood mononuclear cell (PBMC) fraction was obtained by gradient centrifugation over Ficoll-Hypaque (Amersham), as described by Feng, R. et al. S. KD5170, a novel mercaptoketone-based histone deacetylase inhibitor, exerts antimyeloma effects by DNA damage and mitochondrial signaling, *Mol. Cancer Ther.* 2008, 7, 1494-1505. PBMC were washed three times with ice-cold PBS, followed by resuspension at $5 \times 10^5$/mL in the culture medium supplemented with 10% inactivated FBS, 2 mM glutamine, 100 U/mL penicillin, and 100 μg/mL streptomycin (Sigma). The compounds in a stock solution (50 mMin DMSO) were diluted with the culture medium to application conditions and further used for the treatment of PBMC for 3 days. The final DMSO concentrations are always 0.02%. After treatment for 72 h, cell viability was determined using trypan blue exclusion assay. These human cell studies conformed to the guidelines of the Institutional Review Board of the University of Pittsburgh, Pa.

After treatment of these normal cells with compounds 9, 12, 17, 84, and 93 for 3 days, the trypan blue exclusion assays indicated that the cell viability was not significantly affected in comparing with the vehicle control group. For instance, compound 17 did not show any cytotoxic effects at the concentration (1 µM) of 79% inhibition of osteoclastogenesis, and only slight effects on cell viability were observed at high concentration of 10 µM.

Similarly for compounds 84 and 93, cell viability was not significantly affected in comparing with the vehicle control group at 1.25 and 2.5 µM, and only some effects on cell viability were observed at high concentrations of 5 and 10 µM. Compound 84 did not show any cytotoxic effects at 1.25 µM (97% inhibition rate at 1 µM), and only slight effect on cell viability were observed at high concentration of 5 µM.

These results show that the compounds possess favorable therapeutic indexes and the inhibition of human osteoclastogenesis is not a result of their cytotoxicity.

Equivalents

While certain embodiments have been illustrated and described, it should be understood that changes and modifications can be made therein in accordance with ordinary skill in the art without departing from the technology in its broader aspects as defined in the following claims.

The present disclosure is not to be limited in terms of the particular embodiments described in this application. Many modifications and variations can be made without departing from its spirit and scope, as will be apparent to those skilled in the art. Functionally equivalent methods and compositions within the scope of the disclosure, in addition to those enumerated herein, will be apparent to those skilled in the art from the foregoing descriptions. Such modifications and variations are intended to fall within the scope of the appended claims. The present disclosure is to be limited only by the terms of the appended claims, along with the full scope of equivalents to which such claims are entitled. It is to be understood that this disclosure is not limited to particular methods, reagents, compounds compositions or biological systems, which can of course vary. It is also to be understood that the terminology used herein is for the purpose of describing particular embodiments only, and is not intended to be limiting.

In addition, where features or aspects of the disclosure are described in terms of Markush groups, those skilled in the art will recognize that the disclosure is also thereby described in terms of any individual member or subgroup of members of the Markush group.

As will be understood by one skilled in the art, for any and all purposes, particularly in terms of providing a written description, all ranges disclosed herein also encompass any and all possible subranges and combinations of subranges thereof. Any listed range can be easily recognized as sufficiently describing and enabling the same range being broken down into at least equal halves, thirds, quarters, fifths, tenths, etc. As a non-limiting example, each range discussed herein can be readily broken down into a lower third, middle third and upper third, etc. As will also be understood by one skilled in the art all language such as "up to," "at least," "greater than," "less than," and the like, include the number recited and refer to ranges which can be subsequently broken down into subranges as discussed above. Finally, as will be understood by one skilled in the art, a range includes each individual member.

All publications, patent applications, issued patents, and other documents referred to in this specification are herein incorporated by reference as if each individual publication, patent application, issued patent, or other document was specifically and individually indicated to be incorporated by reference in its entirety. Definitions that are contained in text incorporated by reference are excluded to the extent that they contradict definitions in this disclosure.

While several, non-limiting examples have been illustrated and described, it should be understood that changes and modifications can be made therein in accordance with ordinary skill in the art without departing from the invention in its broader aspects as defined in the following claims.

We claim:

1. A method for modulating the activity of a cannabinoid receptor-2(CB2) in a mammal in need thereof, comprising contacting the CB-2receptor with:

(a) a compound of Formula A'

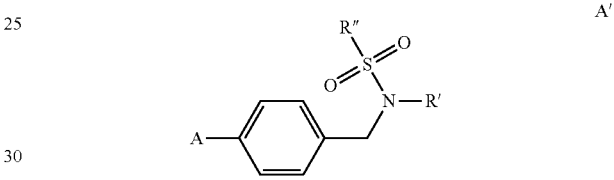

wherein:

A is selected from the group consisting of —NR$_2$, OR, (C$_1$-C$_6$)alkyl, and (C$_3$-C$_8$) heterocycloalkyl;

R is selected from the group consisting of (C$_1$-C$_6$)alkyl, (C$_1$-C$_6$)haloalkyl, and (C$_2$-C$_6$) alkenyl;

R' is selected from the group consisting of sub-formula X, (C$_3$-C$_{14}$)aryl(C$_1$-C$_6$)alkylene-, unsubstituted (C$_3$-C$_{14}$) heteroaryl-(C$_1$-C$_6$)alkylene-, (C$_1$-C$_6$)alkyl, (C$_2$-C$_6$)alkenyl, adamantyl and C$_6$H$_4$R'";

R" is

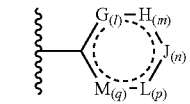

wherein (i) l, m, n, p and q are each an integer 1, (ii) four of G, H, J, L and M are —CH and (iii) the remaining one of G, H, J, L and M is CR$_a$'", or wherein (i) l, m and q are an integer 1, (ii) n is zero, (iii) p is an integer 2, and (iv) G, H and M are —CH and L is CR$_b$'"; and R$_a$'" is selected from the group consisting of H, substituted or unsubstituted (C$_1$-C$_6$)alkyl, —NH$_2$, —NH(C$_1$-C$_6$) alkyl, —N[(C$_1$-C$_6$)alkyl]$_2$, halogen, (C$_1$-C$_6$)haloalkoxy, and (C$_1$-C$_6$)alkoxy, wherein when substituted (C$_1$-C$_6$)alkyl is present, the (C$_1$-C$_6$)alkyl is substituted by one or more substituents selected from the group consisting of halogen, hydroxyl, alkoxy, alkenoxy, alkynoxy, aryloxy, aralkyloxy, heterocyclyloxy, heterocyclylalkoxy groups, carbonyl, ester, urethane, oxime, hydroxylamine, alkoxyamine, aralkoxyamine, thiol, sulfide, sulfoxide, sulfone, sulfonyl, sulfonamide, amine, N-oxide, hydrazine, hydrazide, hydrazine, azide, amide, urea, amidine, guanidine, enamine, imide, isocyanate, isothiocyanate, cyanate, thiocyanate, imine, nitro group, and nitrile;

$R_b'''$ is an unsubstituted aryl;

wherein sub-formula X is represented by:

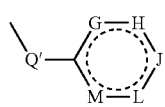

wherein Q' is a bond or a $(C_1-C_6)$alkyl,

G, H, J, L, and M are each independently selected from the group consisting of a bond, CR'''—, —N—, —O—, and —S—, and no two adjacent members of G, H, J, L, or M can simultaneously be —O—, —S—, or N, and

represents the option of having one or more double bonds, or a pharmaceutically acceptable salt thereof; or (b) a compound of Formula B

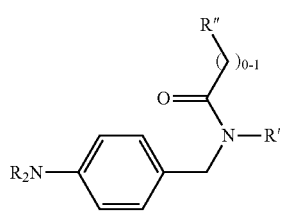

wherein:

R is a $(C_1-C_6)$alkyl;

R' is selected from the group consisting of $(C_1-C_7)$alkyl, adamantyl and $C_6H_4R''$;

R'' is $C_6H_4R'''$; R''' is selected from the group consisting of H, $(C_1-C_6)$alkyl, halogen, and $(C_1-C_6)$alkoxy, or a pharmaceutically acceptable salt thereof.

2. A method for modulating the activity of a cannabinoid receptor-2 (CB2) in a mammal in need thereof, comprising contacting the CB-2 receptor with a compound, or a pharmaceutically acceptable salt thereof, wherein the compound is shown in the following table:

1

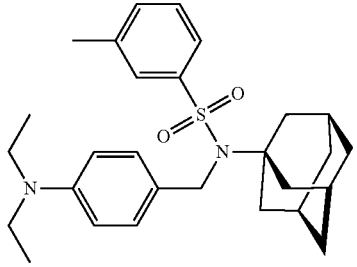 [SMILES: CCN(CC)c1ccc(CN([C@]23C[C@H]4C[C@@H](C[C@H](C4)C2)C3)S(=O)(=O)c2cccc(C)c2)cc1]

2

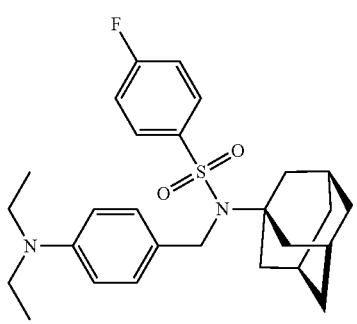

3

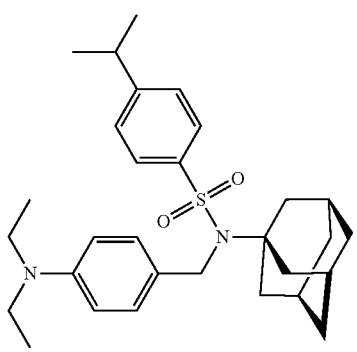

4

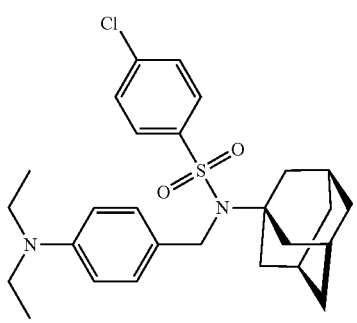 [SMILES: CCN(CC)c1ccc(CN([C@]23C[C@H]4C[C@@H](C[C@H](C4)C2)C3)S(=O)(=O)c2ccc(F)cc2)cc1]

5

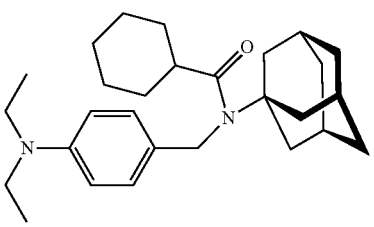

6

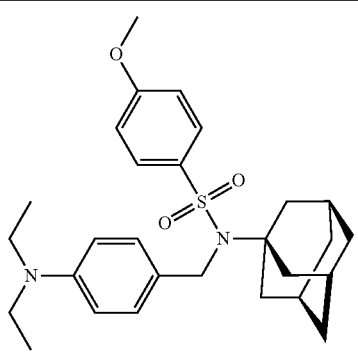
7
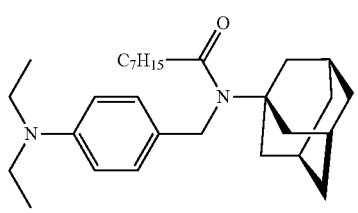
8
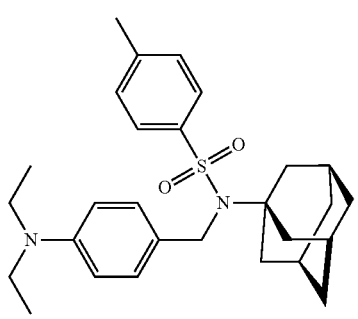 [SMILES: CCN(CC)c1ccc(CN([C@]23C[C@H]4C[C@@H](C[C@H](C4)C2)C3)S(=O)(=O)c2ccc(C)cc2)cc1]
9
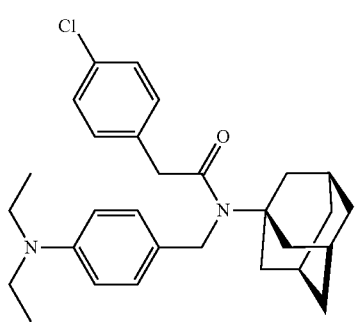 [SMILES: CCN(CC)c1ccc(CN(C(=O)Cc2ccc(Cl)cc2)[C@]23C[C@H]4C[C@@H](C[C@H](C4)C2)C3)cc1]
10
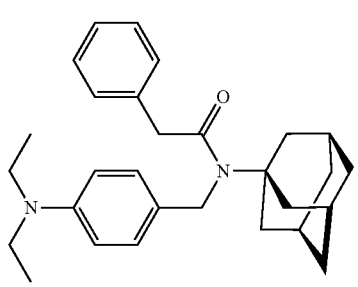 [SMILES: CCN(CC)c1ccc(CN(C(=O)Cc2ccccc2)[C@]23C[C@H]4C[C@@H](C[C@H](C4)C2)C3)cc1]
11
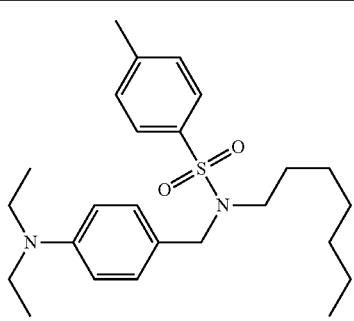
12
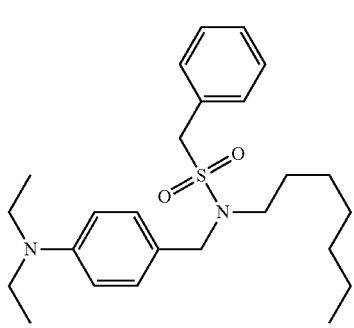 [SMILES: CCCCCCCN(Cc1ccc(N(CC)CC)cc1)S(=O)(=O)Cc1ccccc1]
13
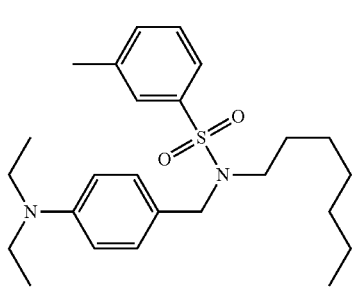 [SMILES: CCCCCCCN(Cc1ccc(N(CC)CC)cc1)S(=O)(=O)c1cccc(C)c1]
14
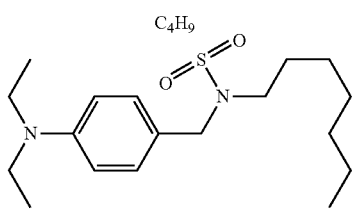
15
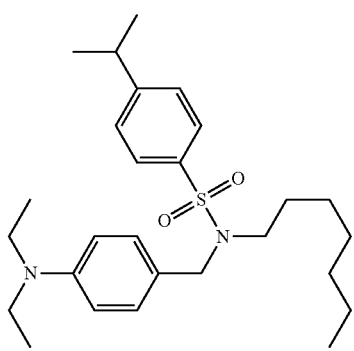 [SMILES: CCCCCCCN(Cc1ccc(N(CC)CC)cc1)S(=O)(=O)c1ccc(C(C)C)cc1]
16

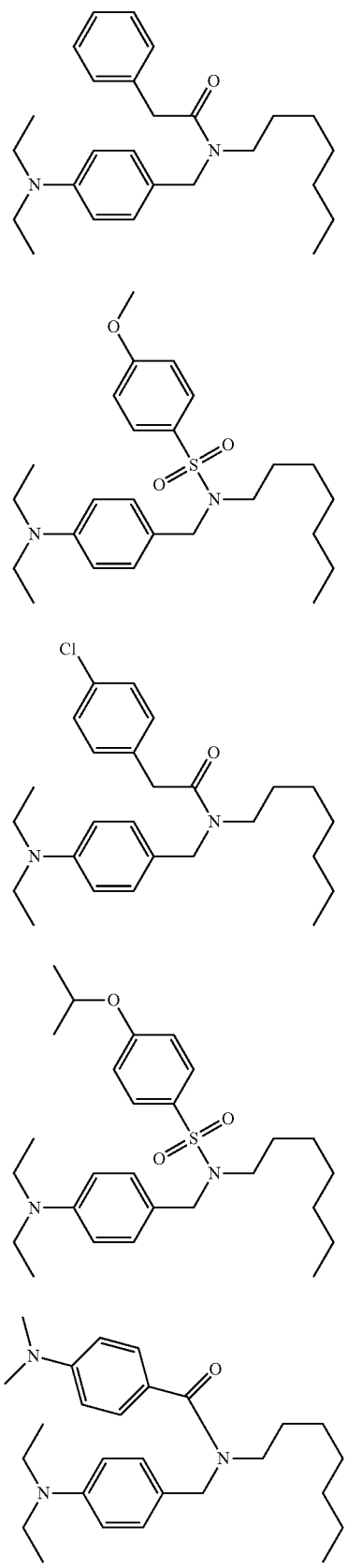
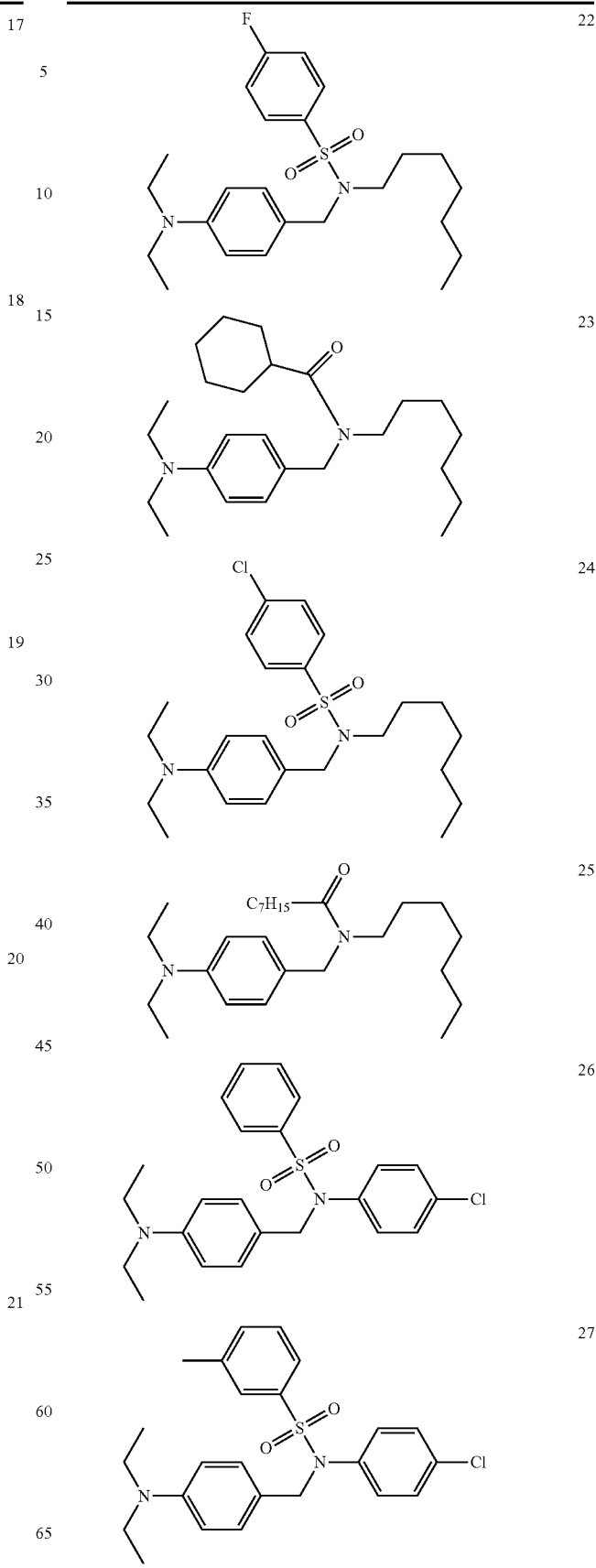

-continued
28
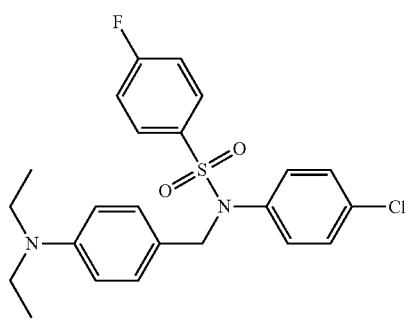 [SMILES: CCN(CC)c1ccc(CN(c2ccc(Cl)cc2)S(=O)(=O)c2ccc(F)cc2)cc1]
29
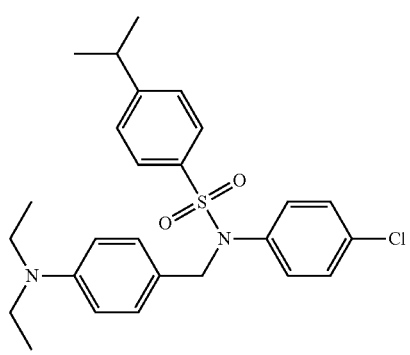 [SMILES: CCN(CC)c1ccc(CN(c2ccc(Cl)cc2)S(=O)(=O)c2ccc(C(C)C)cc2)cc1]
30
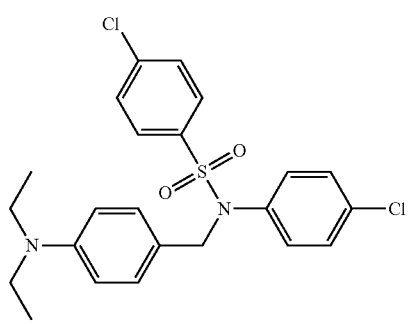 [SMILES: CCN(CC)c1ccc(CN(c2ccc(Cl)cc2)S(=O)(=O)c2ccc(Cl)cc2)cc1]
31
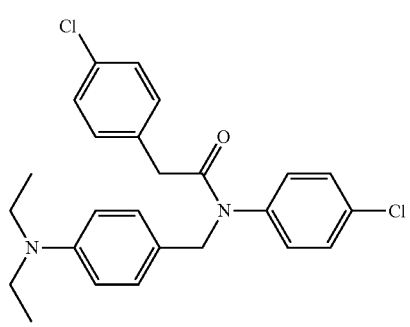 [SMILES: CCN(CC)c1ccc(CN(C(=O)Cc2ccc(Cl)cc2)c2ccc(Cl)cc2)cc1]
-continued
32
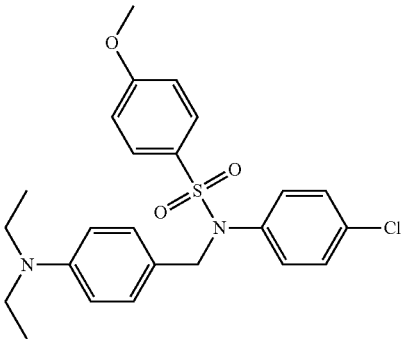 [SMILES: CCN(CC)c1ccc(CN(c2ccc(Cl)cc2)S(=O)(=O)c2ccc(OC)cc2)cc1]
33
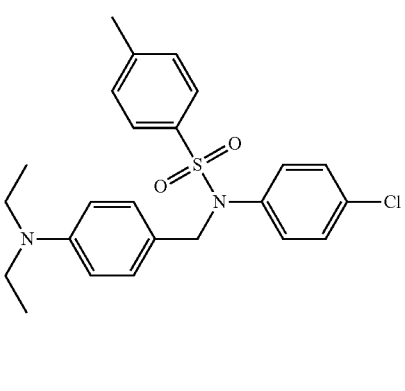 [SMILES: CCN(CC)c1ccc(CN(c2ccc(Cl)cc2)S(=O)(=O)c2ccc(C)cc2)cc1]
34
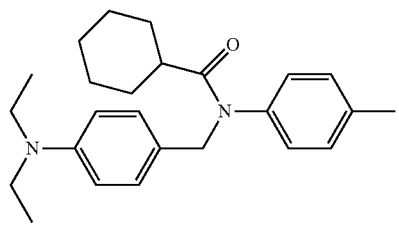 [SMILES: CCN(CC)c1ccc(CN(C(=O)C2CCCCC2)c2ccc(C)cc2)cc1]
35
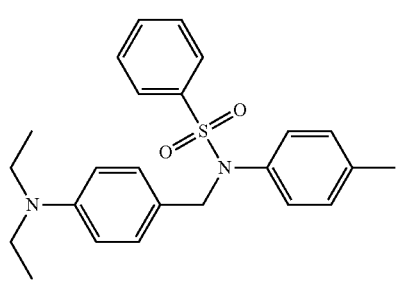 [SMILES: CCN(CC)c1ccc(CN(c2ccc(C)cc2)S(=O)(=O)c2ccccc2)cc1]
36
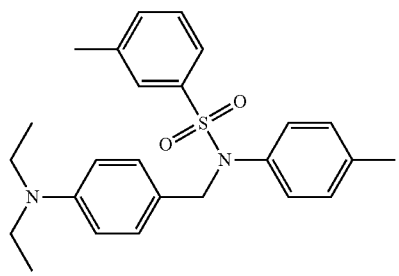 [SMILES: CCN(CC)c1ccc(CN(c2ccc(C)cc2)S(=O)(=O)c2cccc(C)c2)cc1]

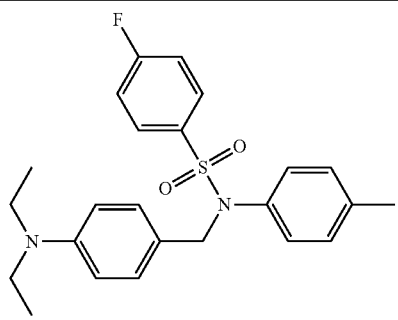

37

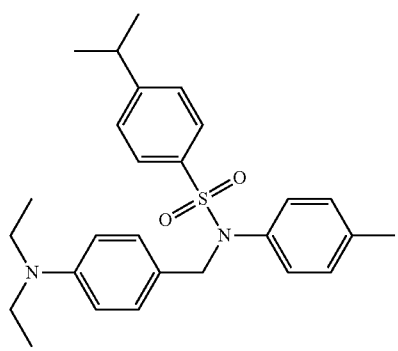 [SMILES: CCN(CC)c1ccc(CN(c2ccc(C)cc2)S(=O)(=O)c2ccc(C(C)C)cc2)cc1]

38

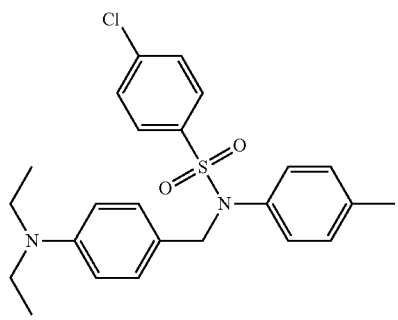 [SMILES: CCN(CC)c1ccc(CN(c2ccc(C)cc2)S(=O)(=O)c2ccc(Cl)cc2)cc1]

39

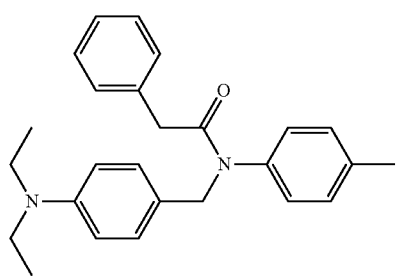 [SMILES: CCN(CC)c1ccc(CN(C(=O)Cc2ccccc2)c2ccc(C)cc2)cc1]

40

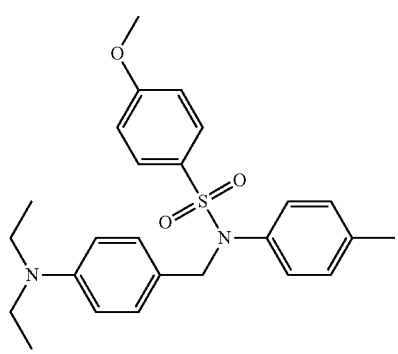 [SMILES: CCN(CC)c1ccc(CN(c2ccc(C)cc2)S(=O)(=O)c2ccc(OC)cc2)cc1]

41

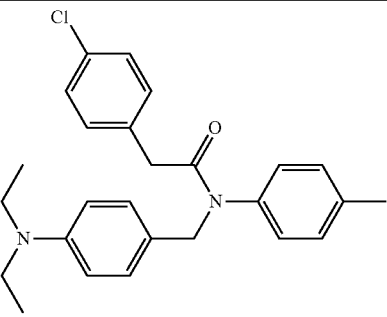

42

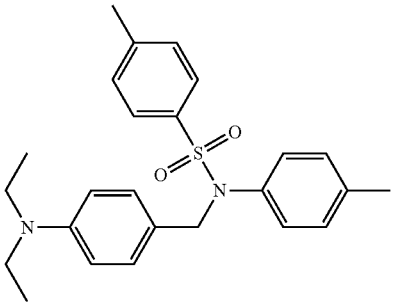 [SMILES: CCN(CC)c1ccc(CN(c2ccc(C)cc2)S(=O)(=O)c2ccc(C)cc2)cc1]

43

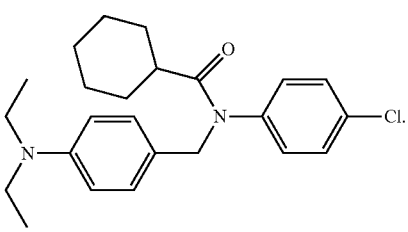 [SMILES: CCN(CC)c1ccc(CN(C(=O)C2CCCCC2)c2ccc(Cl)cc2)cc1]

44

3. The method according to claim 2, wherein the compound is selected from the group consisting of Compounds 26-44, or a pharmaceutically acceptable salt thereof.

4. The method according to claim 2, wherein the compound is selected from the group consisting of Compounds 14, 32 and 41, or a pharmaceutically acceptable salt thereof.

5. The method according to claim 3, wherein the compound is Compound 41, or a pharmaceutically acceptable salt thereof.

6. The method according to claim 1, wherein the mammal is a human.

7. The method according to claim 2, wherein the mammal is a human.

8. The method according to claim 1, wherein the compound is a compound of Formula A.

9. The method according to claim 1, wherein the compound is a compound of Formula B.

10. The method of claim 8, wherein A is —NR$_2$ and R is a (C$_1$-C$_6$)alkyl.

11. The method of claim 8, wherein R″ is

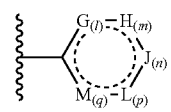

wherein (i) l, m, n, p and q are each an integer 1, (ii) four of G, H, J. L and M are —CH, and (iii) the remaining one of G, H, J, L and M is $CR_a'''$, and $R_a'''$ is selected from the group consisting of H, halogen, $(C_1-C_6)$haloalkoxy, and $(C_1-C_6)$alkoxy.

12. The method of claim 2, wherein the mammal suffers from multiple myeloma.

13. The method of claim 2, wherein the mammal suffers from osteoporosis.

14. The method of claim 8, wherein the mammal suffers from multiple myeloma.

15. The method of claim 8, wherein the mammal suffers from osteoporosis.

16. The method of claim 9, wherein the mammal suffers from multiple myeloma.

17. The method of claim 9, wherein the mammal suffers from osteoporosis.

* * * * *